US012721830B2

(12) United States Patent
Steiner et al.

(10) Patent No.: US 12,721,830 B2
(45) Date of Patent: *Sep. 1, 2026

(54) COMPOSITIONS COMPRISING SELECTIVE ANDROGEN RECEPTOR MODULATOR COMPOUNDS IN COMBINATION WITH WEIGHT LOSS DRUGS AND USES THEREOF FOR QUALITY WEIGHT LOSS

(71) Applicant: VERU INC., Miami, FL (US)

(72) Inventors: Mitchell S. Steiner, Germantown, TN (US); Kester Gary Barnette, Denver, NC (US)

(73) Assignee: VERU INC., Miami, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/319,108

(22) Filed: Sep. 4, 2025

(65) Prior Publication Data

US 2026/0007630 A1 Jan. 8, 2026

Related U.S. Application Data

(63) Continuation-in-part of application No. 19/248,412, filed on Jun. 24, 2025, which is a continuation-in-part of application No. 19/037,276, filed on Jan. 26, 2025, which is a continuation-in-part of application No. 18/905,976, filed on Oct. 3, 2024.

(60) Provisional application No. 63/660,989, filed on Jun. 17, 2024, provisional application No. 63/644,426, filed on May 8, 2024, provisional application No. 63/608,780, filed on Dec. 11, 2023, provisional application No. 63/587,708, filed on Oct. 3, 2023.

(51) Int. Cl.

*A61K 31/277* (2006.01)
*A61K 38/26* (2006.01)
*A61P 3/04* (2006.01)
*A61P 21/00* (2006.01)
*A61P 21/06* (2006.01)

(52) U.S. Cl.

CPC ............ *A61K 31/277* (2013.01); *A61K 38/26* (2013.01); *A61P 3/04* (2018.01); *A61P 21/00* (2018.01); *A61P 21/06* (2018.01)

(58) Field of Classification Search

CPC ......... A61K 31/277; A61K 38/26; A61P 3/04; A61P 21/00; A61P 21/06

See application file for complete search history.

(56) References Cited

U.S. PATENT DOCUMENTS

| | | | |
|---|---|---|---|
| 9,604,916 | B2 | 3/2017 | Dalton et al. |
| 2007/0066568 | A1 | 3/2007 | Dalton et al. |
| 2012/0115777 | A1 | 5/2012 | Richardson et al. |
| 2014/0134274 | A1 | 5/2014 | Steiner et al. |

FOREIGN PATENT DOCUMENTS

| | | |
|---|---|---|
| WO | WO 2008/008433 A2 | 1/2008 |

OTHER PUBLICATIONS

Aronne, L.J et al; "Continued Treatment With Tirzepatide for Maintenance of Weight Reduction in Adults With Obesity, The SURMOUNT-4 Randomized Clinical Trial", JAMA 2024, vol. 331, No. 1, pp. 38-48.

Baumgartner, R.N.; "Epidemiology of Sarcopenia among the Elderly in New Mexico", Am J Epidemiol 1998, vol. 147, No. 8, pp. 755-763.

Cruz-Jentoft, A.J.; "Sarcopenia: European consensus on definition and diagnosis", Age and Ageing 2010; 39: pp. 412-423.

Dullo, A.G.; "Passive and active roles of fat-free mass in the control of energy intake and body composition regulation", European Journal of Clinical Nutrition 2017, 71, pp. 353-357.

Dullo, A.G.; "Collateral Fattening: When a Deficit in Lean Body Mass Drives Overeating", Obesity 2017, vol. 25, No. 2, pp. 277-279.

Ida, Satoshi et al; "Effects of Antidiabetic Drugs on Muscle Mass in Type 2 Diabetes Mellitus", Current Diabetes Reviews 2021, vol. 17, Iss. 3, pp. 293-303.

Jastreboff, A.M. et al; "Tirzepatide Once Weekly for the Treatment of Obesity", N. Engl J Med 2022, vol. 387, No. 3, pp. 205-216.

Locatelli, J.C.; "Incretin-Based Weight Loss Pharmacotherapy: Can Resistance Exercise Optimize Changes in Body Composition?", Diabetes Care 2024, 47(10): pp. 1718-1730.

Omura, Takuya et al; "Skeletal muscle as a treatment target for older adults with diabetes mellitus: The importance of a multimodal intervention based on functional category", Geriatrics & Gerontology International 2022, 22 (2) pp. 110-120.

Rubino, D. et al; "Effect of Continued Weekly Subcutaneous Semaglutide vs Placebo on Weight Loss Maintenance in Adults With Overweight or Obesity, The STEP 4 Randomized Clinical Trial", JAMA 2021, 325(14): pp. 1414-1425.

Rosenberg, Irwin H.; "Summary comments", Am J Clin Nutr 1989, 50 (5), pp. 1231-1233.

Wilding, John P.H. et al; "Once-Weekly Semaglutide in Adults with Overweight or Obesity", N. Engl J Med 2021, vol. 384, No. 11, pp. 989-1002.

Wilding, John P.H. et al; "Weight regain and cardiometabolic effects after withdrawal of semaglutide: The STEP 1 trial extension", Diabetes Obes Metab. 2022; 24: pp. 1553-1564.

Invitation to Pay Additional Search Fees ( PCT Form 206) dated Mar. 16, 2026, in respect of PCT International Application No. PCT/US2026/010967.

*Primary Examiner* — Rayna Rodriguez

(74) *Attorney, Agent, or Firm* — Mark S. Cohen; PEARL COHEN LLP

(57) ABSTRACT

The present invention relates to the field of treatment for body composition changes in weight management. In some embodiments, the present invention provides compositions and methods for mitigating the adverse effects of treatment by weight loss drugs that suppress appetite including incretin agonist or antagonist containing drugs such as glucagon-like peptide-1 receptor agonists (GLP-1 RAs) or by sodium-glucose transport protein 2 (SGLT-2) inhibitors. In one embodiment, the present invention provides a composition of semaglutide and a selective androgen receptor modulator (SARM) compound of Formula IX.

30 Claims, 6 Drawing Sheets

Total lean mass
Up to week 12 visit

Placebo N=15, Treated N=14
Placebo corrected % change = +4.96%

Total body weight
Up to week 21 visit

Placebo N=12, Treated N=12
Placebo corrected % change = -4.51%

| Day | Screen[a] | Day 1 | Visit every 28 days[b] | Visits at Day Day 112, and Day 196[f] | End of study[f, g] | Follow up 30 days post-dose[c] |
|---|---|---|---|---|---|---|
| Informed Consent and HIPAA | X | | | | | |
| Medical History | X | | | | | |
| Demographics | X | | | | | |
| Assessment of Eligibility | X | X | | | | |
| Randomization (IRT) | | X | | | | |
| Physical Exam | X | X[i] | X | X[i] | X[i] | |
| Vital signs (including body weight) | X | X | X | X | X | |
| Waist circumference | | X | | X | X | |
| 12-lead ECG (single) | X | | | X | X | |
| DEXA total body composition scan[d, e] | | X | | X | X | |
| Physical function test (stair climb)[d] | | X | | X | X | |
| C-SSRS & PHQ-9 | X | X | X | X | X | |
| OSA assessment[j] | X | | | X | X | |
| Clinical Laboratory Tests | | | | | | |
| Hematology | X | X[k] | X | X | X | X |
| Urinalysis | X | X[k] | | X[g] | X | X |
| Serum Chemistry | X | X[k] | X | X | X | X |
| Hemoglobin A1c | X | | | X | X | |
| Serum hormones | X | | | X | X | |
| Lipid panel | X | | | X | X | |
| PT/INR, aPTT | X | | | | | |
| Distribute drug | | X | X | X[h] | X[h] | |
| Drug accountability | | | X | X | X | |
| Record concomitant medications | X | X | X | X | X | |
| Record non-medication therapies | X | X | X | X | X | |
| Assessment of AEs | | X | X | X | X | X |

FIGURE 3

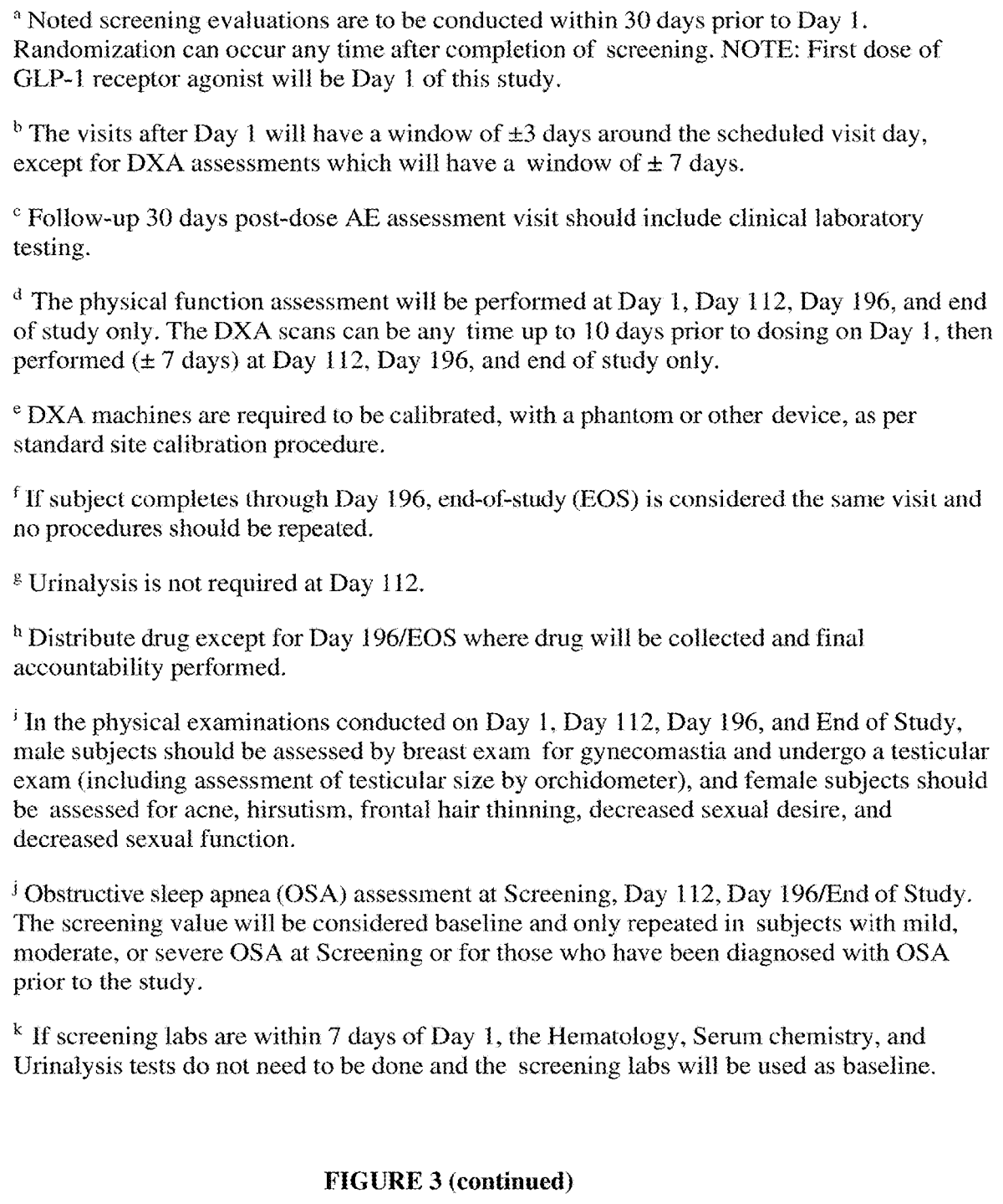

[a] Noted screening evaluations are to be conducted within 30 days prior to Day 1. Randomization can occur any time after completion of screening. NOTE: First dose of GLP-1 receptor agonist will be Day 1 of this study.

[b] The visits after Day 1 will have a window of ±3 days around the scheduled visit day, except for DXA assessments which will have a window of ± 7 days.

[c] Follow-up 30 days post-dose AE assessment visit should include clinical laboratory testing.

[d] The physical function assessment will be performed at Day 1, Day 112, Day 196, and end of study only. The DXA scans can be any time up to 10 days prior to dosing on Day 1, then performed (± 7 days) at Day 112, Day 196, and end of study only.

[e] DXA machines are required to be calibrated, with a phantom or other device, as per standard site calibration procedure.

[f] If subject completes through Day 196, end-of-study (EOS) is considered the same visit and no procedures should be repeated.

[g] Urinalysis is not required at Day 112.

[h] Distribute drug except for Day 196/EOS where drug will be collected and final accountability performed.

[i] In the physical examinations conducted on Day 1, Day 112, Day 196, and End of Study, male subjects should be assessed by breast exam for gynecomastia and undergo a testicular exam (including assessment of testicular size by orchidometer), and female subjects should be assessed for acne, hirsutism, frontal hair thinning, decreased sexual desire, and decreased sexual function.

[j] Obstructive sleep apnea (OSA) assessment at Screening, Day 112, Day 196/End of Study. The screening value will be considered baseline and only repeated in subjects with mild, moderate, or severe OSA at Screening or for those who have been diagnosed with OSA prior to the study.

[k] If screening labs are within 7 days of Day 1, the Hematology, Serum chemistry, and Urinalysis tests do not need to be done and the screening labs will be used as baseline.

FIGURE 3 (continued)

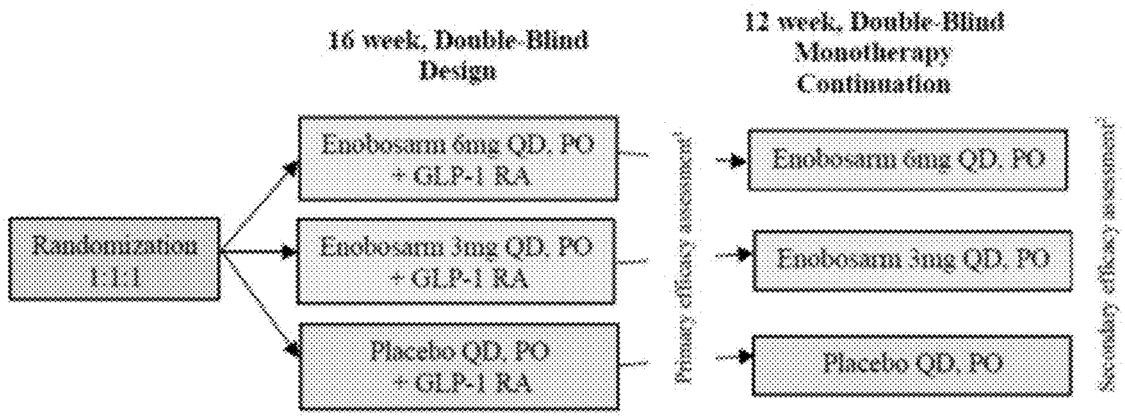

[1] The primary efficacy assessment will be conducted by the IDMC for the study. The focus of this analysis will be change in total lean mass (percent and absolute), total fat mass (percent and absolute), total body weight (percent and absolute), and physical function (percent and absolute) from Day 1 to Day 112.

[2] The secondary efficacy assessment will focus on the effect of Formula IX in maintenance of body weight, total lean body mass, total fat mass, and physical function (Day 112 to Day 196) in the absence of GLP-1 RA dosing.

FIGURE 4

COMPOSITIONS COMPRISING SELECTIVE ANDROGEN RECEPTOR MODULATOR COMPOUNDS IN COMBINATION WITH WEIGHT LOSS DRUGS AND USES THEREOF FOR QUALITY WEIGHT LOSS

CROSS REFERENCE TO RELATED APPLICATIONS

This application is a continuation-in-part of U.S. patent application Ser. No. 19/248,412, filed on Jun. 24, 2025, which is a continuation-in-part of U.S. patent application Ser. No. 19/037,276, filed on Jan. 26, 2025, which is a continuation-in-part of U.S. patent application Ser. No. 18/905,976, filed on Oct. 3, 2024, which claims the benefit of U.S. Provisional Patent Application No. 63/660,989, filed on Jun. 17, 2024, U.S. Provisional Patent Application No. 63/644,426, filed on May 8, 2024, U.S. Provisional Patent Application No. 63/608,780, filed on Dec. 11, 2023, and U.S. Provisional Patent Application No. 63/587,708, filed on Oct. 3, 2023, all of which are incorporated herein by reference in their entirety.

FIELD OF THE INVENTION

The present invention relates to the field of treatment to improve body composition changes in weight management. In some embodiments, the present invention provides compositions and methods for mitigating the adverse effects of treatment by weight loss drugs that suppress appetite including incretin agonist or antagonist containing drugs such as glucagon-like peptide-1 receptor agonists (GLP-1 RAs) or by sodium-glucose transport protein 2 (SGLT-2) inhibitors. In one embodiment, the present invention provides a composition of semaglutide and a selective androgen receptor modulator (SARM) compound of Formula IX.

BACKGROUND OF THE INVENTION

Obesity is a common disease with 41.9% of the population of the United States being obese (NHANES 2021). Obesity can lead to heart disease, stroke, type 2 diabetes or diabetes mellitus, and some types of cancers.

The glucagon-like peptide 1 receptor agonists (GLP-1 RAs) are attractive options for the treatment of obesity and type II diabetes because they effectively lower hemoglobin A1C (HbA1C) and weight while having a low risk of hypoglycemia. Some GLP-1 RAs also have documented cardiovascular benefits. GLP-1 RAs increase glucose-dependent insulin secretion and decrease inappropriate glucagon secretion, delay gastric emptying, and increase satiety. The GLP-1 RA class alone, together with other incretins, or other incretin agonist or antagonist containing drugs have grown in number in the last decade with several agents available for use in the United States and Europe for treatment of weight loss or diabetes. The impact of these agents in terms of their ability to induce weight loss in obese or overweight patients, as well as in terms financial profit for pharmaceutical companies, has been extreme; stimulating tremendous ongoing R&D efforts to discover and develop more such agents or fine-tune existing agents.

SGLT-2 inhibitors are another class of prescription medicines that are FDA-approved for use with diet and exercise to lower blood sugar in adults with type 2 diabetes and may reduce weight (though not approved for weight loss as of 2025). Medicines in the SGLT-2 inhibitor class include bexagliflozin, canagliflozin, dapagliflozin, ertugliflozin, and empagliflozin. SGLT-2 inhibitors, which are also called gliflozins, are a class of drugs that lower blood sugar levels by preventing the kidneys from reabsorbing glucose (and other sugars) that is created by the body and the extra glucose exits the body in the urine. SGLT-2 inhibitors have been shown to improve glycemic control in conjunction with diet and exercise in type 2 diabetes and to reduce major cardiovascular events in type 2 diabetes with pre-existing cardiovascular disease.

Glucagon-like peptide-1 (GLP-1) receptor agonists have been used as an adjunct to diet and exercise to improve glycemic control in adults and pediatric patients 10 years of age and older with type 2 diabetes mellitus. GLP-1 receptor agonists are also used to reduce the risk of major adverse cardiovascular events in adults with type 2 diabetes (aka diabetes mellitus) who have established cardiovascular disease or multiple cardiovascular risk factors since first approved by the United States Food and Drug Administration in 2005 (BYDUREON® Prescribing Information, AstraZeneca group of companies, VICTOZA® Prescribing Information, Novo Nordisk A/S). In 2021, select GLP-1 receptor agonists were approved as an adjunct to a reduced calorie diet and increased physical activity for chronic weight management in adult patients with an initial body mass index (BMI) of 30 kg/m$^2$ or greater (obesity), or 27 kg/m$^2$ or greater (overweight) in the presence of at least one weight-related comorbid condition (e.g., hypertension, type 2 diabetes, or dyslipidemia) (WEGOVY® Prescribing Information, Novo Nordisk Inc.). In the pivotal studies, body weight was reduced by 9.6-16.0% with 25.1-53.4% of the patients losing at least 15% of their total body weight.

GLP-1 RAs improve glycemic control and cause weight loss by suppressing appetite and slowing gastric emptying. Unfortunately, this weight loss is nonselective for the type of tissue as there is significant loss of fat body mass (FBM; also referred to as fat mass herein, e.g., in Example 7) and lean body mass (LBM; 20-50%) which includes muscle mass and bone. Thus, there are safety concerns associated with the loss of LBM (also referred to as lean mass herein, e.g., in Example 7), which plays a role in maintaining glucose and fat metabolism as well as strength and physical function. Consequently, there is a major medical need to mitigate this adverse effect of lean body mass loss caused by treatment with weight loss drugs such as incretin agonist or antagonist containing drugs as a class including GLP-1 RA and agents that mimic GLP-1, GLP-2, GIP, glucagon, amylin, and/or oxyntomodulin as is discussed in greater detail herein below; and other FDA approved and investigational weight loss drugs that decrease appetite such as CB1 receptor modulators; or SGLT-2 inhibitors. As discussed herein, these drugs cause weight loss due to negative calorie balance such that both lean mass and fat mass are lost. Associated with the loss of lean mass is loss of muscle mass and muscle strength, leading to compromised physical function.

It has been reported that while patients lose total body weight, the loss of body weight is from loss of total body fat mass and total body lean mass (muscle or fat-free mass) (Ida S, Kaneko R, Imataka K, Okubo K, Shirakua Y, Azuma K, Fujiwara R, and Murata K. Curr Diabetes Rev. 2021; 17(3): 293-303). In a meta-analysis of 18 randomized controlled trials that included 1363 subjects, a GLP-1 receptor agonist (semaglutide) resulted in a 2.84 kg reduction in fat-free mass compared to placebo. Semaglutide treatment in the STEP 1 study showed a 6.92 kg loss of LBM at 68 weeks which was 40% of the total weight lost (Wilding J P H et al. NEJM 384:989-1002, 2021). Tirzepatide, a GLP-1 RA plus GIP agonist, treatment resulted in 6 kg loss of LBM by 72 weeks (Jastreboff A M et al. N Engl J Med 387:205-216, 2022). While SGLT-2 inhibitors (dapagliflozin and canagliflozin) resulted in 0.53-0.90 kg reduction in fat-free mass.

The importance of muscle mass and maintaining muscle mass for healthy aging is well known (Janssen et al. 2000). Sarcopenia is a progressive loss of skeletal muscle mass that can result in physical disability, poor quality of life and death (Baumgartner et al. Am J Epidemiol. 1998; 147:755-763, Cruz-Jentoft et al. Age Ageing. 2010; 39:412-423, Rosenberg. Am J Clin Nutr. 1989; 50:1231-1233). The process of muscle loss appears to be accelerated by the use of weight loss drugs like GLP-1 receptor agonists, incretins, and SGLT-2 inhibitors whether these products are used for the treatment of type 2 diabetes or for management of weight. The magnitude of LBM loss associated with some incretin therapies exceeds that seen during 10 years of aging, which may be particularly clinically relevant following longer-term therapy and/or in patients who are older and have sarcopenia (Omura T et al. Geriatr Gerontol Int 22:110-120, 2022). The loss of muscle mass with weight loss drugs like GLP-1 receptor agonists or SGLT-2 inhibitors may result in muscle weakness, decreased gait, loss of physical function, loss of balance, increased risk of falls and fractures, high hospitalization rates, and increased mortality. For example, in a cardiovascular outcomes trial (NCT03574597), patients reported more fractures of the hip and pelvis on WEGOVY® than on placebo. This was true in female patients: 1.0% (24/2448) vs. 0.2% (5/2424); and in patients ages 75 years and older: 2.4% (17/703) vs. 0.6% (4/663), respectively. Obese patients that have sarcopenic obesity, a common subgroup, have both obesity and age-related low muscle mass at the same time and are potentially at the greatest risk for developing critically low muscle mass and muscle weakness when taking weight loss drugs like GLP-1 or SGLT-2 drugs for weight-loss or diabetes mellitus.

Thus, there is a need to mitigate this adverse effect on lean body mass loss due to treatment by incretin agonist or antagonist containing drugs (e.g., GLP-1 RAs, GLP-2 receptor agonists or antagonists, gastric intestinal peptide receptor (GIPR; also known as glucose-dependent insulinotropic polypeptide receptor) agonists or antagonists, etc.) or SGLT-2 inhibitors.

Another adverse effect of weight loss drugs, especially incretins including orforglipron, semaglutide and tirzepatide, is that they adversely affect body composition as they deplete muscle reserves which stimulates appetite after the weight loss drug is discontinued. The overeating that occurs with removal of energy restriction by the weight loss drug and appetite stimulatory signals from depleted muscle leads to rebound, rapid weight regain consisting mostly of fat (Wilding J P H et al. Diabetes Obs Metab 24:1553-1564, 2022; Rubino D et al. JAMA 325:1414-1425, 2021; Aronne L et al. JAMA 331:38-48, 2024; Locatelli J C et al. Diabetes Care 47:1718-1730, 2024; Dulloo A Obesity 25:277-279, 2017; Dulloo A G et al. Eur J Clin Nutrition 71:353-357, 2017). Consequently, the patient with obesity who discontinues the weight loss drug is unable to maintain the weight they lost, and unfortunately, the patient's body composition is now further enriched with higher fat mass with greater depletion of LBM (Locatelli J C et al. Diabetes Care 47:1718-1730, 2024). Avoidance of muscle loss may allow maintenance of the weight loss caused by the weight loss drug, whether used for weight loss, diabetes, or heart or kidney diseases.

SUMMARY OF THE INVENTION

In one aspect, the present invention provides a composition comprising a pharmaceutical composition of Formula IX, or an optical isomer, a racemic mixture, a pharmaceutically acceptable salt, a pharmaceutical product, a hydrate, an N-oxide, or a crystal thereof; and a pharmaceutical composition of semaglutide:

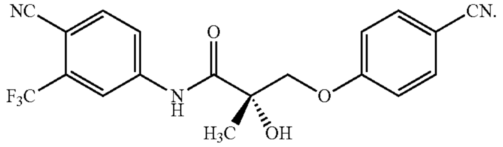

IX

In another aspect, the present invention provides a method for reducing or treating adverse effects caused by semaglutide monotherapy, comprising co-administering to the subject the pharmaceutical composition of Formula IX and the pharmaceutical composition of semaglutide of the composition of the invention as described herein.

In some embodiments, the adverse effects comprise one or more of loss in (i) lean body mass, fat-free mass, or muscle mass, (ii) muscle strength, or (iii) physical function. In certain embodiments, the loss in lean body mass is from about 3% to 20% of the total body weight in the subject.

In a further aspect, the present invention provides a method for maintenance or improvement of body composition compared to semaglutide monotherapy, comprising co-administering to the subject the pharmaceutical composition of Formula IX and the pharmaceutical composition of semaglutide of the composition of the invention as described herein.

In a further aspect, the present invention provides a method of reducing or treating rebound in a subject in need thereof, wherein the rebound is in one or more of (i) weight gain, (ii) fat mass gain, and (iii) lean mass loss when the semaglutide is discontinued in said subject but Formula IX treatment continues as monotherapy:

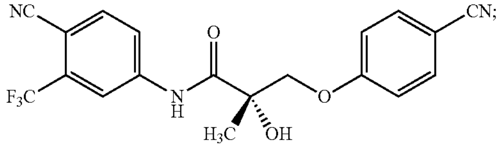

IX wherein the subject was previously co-administered the pharmaceutical composition of Formula IX and the pharmaceutical composition of semaglutide of the composition of the invention as described herein.

These and other aspects of the invention will be appreciated from the ensuing descriptions of the figures and detailed description of the invention.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

(FIG. 1A) total fat mass, (FIG. 1B) total lean mass, and (FIG. 1C) total body weight.

FIG. 3 depicts the schedule of study evaluations associated with the proof-of-concept Phase IIb clinical trial in Example 6.

FIG. 4 depicts the design of the phase IIb proof-of-concept clinical trial in Example 6.

Figure 1A:
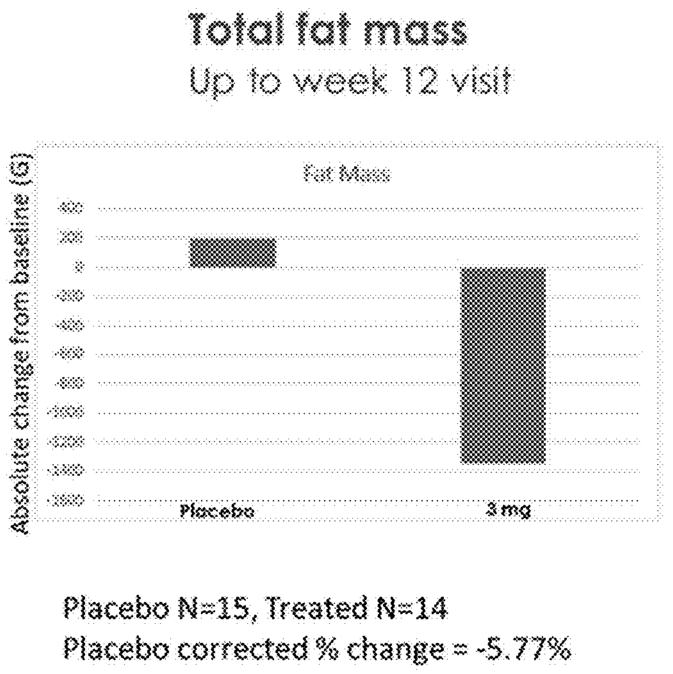
FIGS. 1A, 1B, and 1C depict a post-hoc analysis of a subpopulation of older subjects (≥60 years of age) with obesity (BMI≥30)

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

In one aspect, the present invention provides a method for preventing, reducing, or treating adverse effects, including body composition changes and/or physical function declines, caused by a weight loss drug in a subject who is under treatment or stops treatment with the weight loss drug, comprising administering to the subject a therapeutically effective amount of a selective androgen receptor modulator (SARM) compound represented by a structure of Formula I.

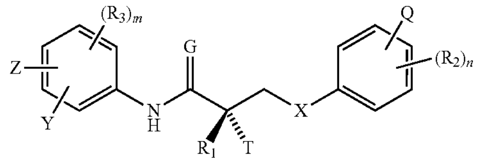

I wherein

X is a bond, O, $CH_2$, NH, S, Se, PR, NO, or NR;

G is O or S;

T is OH, OR, —$NHCOCH_3$, or NHCOR;

R is alkyl, haloalkyl, dihaloalkyl, trihaloalkyl, $CH_2F$, $CHF_2$, $CF_3$, $CF_2CF_3$, aryl, phenyl, halogen, alkenyl, or OH;

$R_1$ is $CH_3$, $CH_2F$, $CHF_2$, $CF_3$, $CH_2CH_3$, or $CF_2CF_3$;

$R_2$ is H, F, Cl, Br, I, $CH_3$, $CF_3$, OH, CN, $NO_2$, $NHCOCH_3$, $NHCOCF_3$, NHCOR, alkyl, arylalkyl, OR, $NH_2$, NHR, $N(R)_2$, or SR;

$R_3$ is H, F, Cl, Br, I, CN, $NO_2$, COR, COOH, CONHR, $CF_3$, or $Sn(R)_3$, or $R_3$ together with the benzene ring to which it is attached forms a fused ring system represented by the structure:

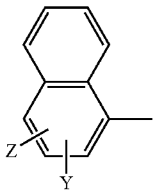

or

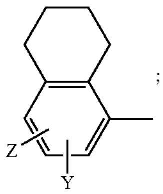

;

Z is $NO_2$, CN, COR, COOH, or CONHR;

Y is $CF_3$, F, Br, Cl, I, CN, or $Sn(R)_3$;

Q is CN, alkyl, halogen, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, or SR;

or Q together with the benzene ring to which it is attached is a fused ring system represented by structure A, B, or C:

A

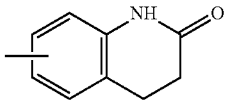

B

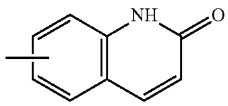

C

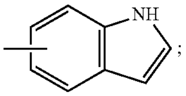

;

n is an integer of 1-4; and m is an integer of 1-3, or an optical isomer, a racemic mixture, a pharmaceutically acceptable salt, a pharmaceutical product, a hydrate, an N-oxide, or a crystal thereof.

In another embodiment, the SARM compound used in the above method is represented by a structure of Formula II:

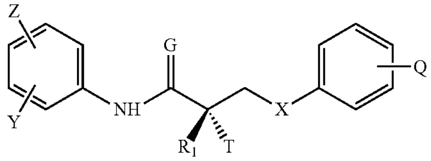

II wherein

X is a bond, O, $CH_2$, NH, Se, PR, or NR;

G is O or S;

T is OH, OR, —$NHCOCH_3$, or NHCOR;

Z is $NO_2$, CN, COR, COOH, or CONHR;

Y is I, $CF_3$, Br, Cl, or $Sn(R)_3$;

Q is CN, alkyl, halogen, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, or SR;

or Q together with the benzene ring to which it is attached is a fused ring system represented by structure A, B, or C:

A

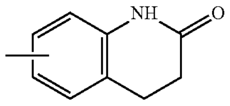

B

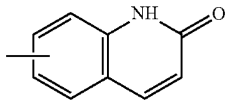

C

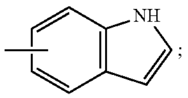

R is a $C_1$-$C_4$ alkyl, aryl, phenyl, alkenyl, hydroxyl, a $C_1$-$C_4$ haloalkyl, halogen, or haloalkenyl; and $R_1$ is $CH_3$, $CF_3$, $CH_2CH_3$, or $CF_2CF_3$.

In one embodiment, the SARM compound is represented by a structure of Formulas VIII, IX, X, XI, XII, XIII, and XIV:

VIII

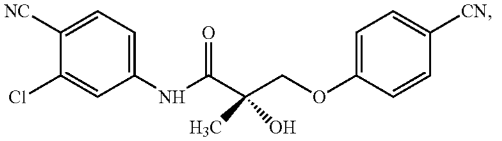

IX

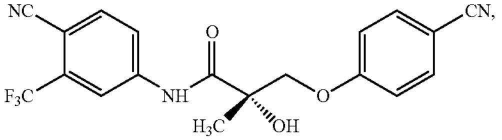

X

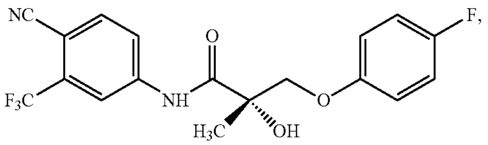

XI

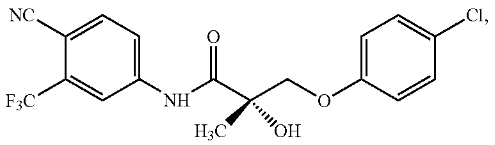

XII

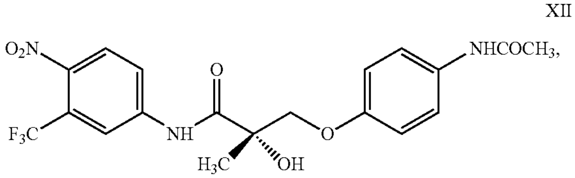

XIII

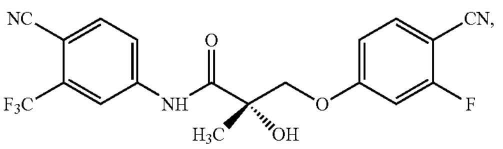

or

-continued

XIV

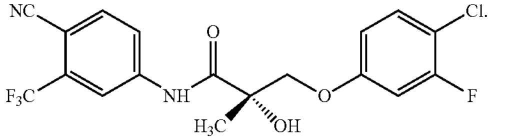

In one embodiment, the SARM compound is represented by a structure of Formula IX,

IX

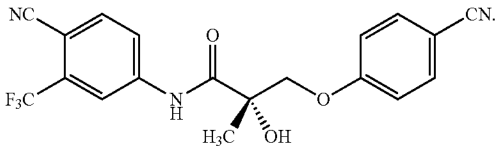

In some embodiments of the method of the invention, the subject has sarcopenic obesity. In other embodiments, the subject is 60 years old or older. In certain embodiments, the subject has sarcopenic obesity and is 60 years old or older. In some embodiments, the subject has pre-diabetes or diabetes mellitus.

In some embodiments, the weight loss drug is an incretin agonist or antagonist containing drug, wherein the incretin agonist or antagonist is a glucagon-like peptide-1 (GLP-1) receptor agonist, and/or a glucagon-like peptide-2 (GLP-2) receptor agonist, and/or a glucose-dependent insulinotropic polypeptide (GIP) antagonist or a GIP agonist, and/or a glucagon agonist, and/or an amylin agonist, and/or an oxyntomodulin agonist, or any combination thereof.

In some embodiments, the incretin agonist or antagonist containing drug is a GLP-1 receptor agonist. In some embodiments, the incretin agonist or antagonist containing drug is a GLP-2 receptor agonist. In some embodiments, the incretin agonist or antagonist containing drug is a GLP-1 RA and a GIP agonist. In some embodiments, the incretin agonist or antagonist containing drug is a GLP-1 RA and a GIP antagonist. In some embodiments, the incretin agonist or antagonist containing drug is a GLP-1 RA and a GIP agonist and a glucagon agonist. In some embodiments, the incretin agonist or antagonist containing drug is a GLP-1 RA and an amylin agonist. In some cases, a single molecule possesses more than one type of incretin activity. In some cases, multiple molecules are used to achieve multiple types of weight loss and/or incretin activity including antagonism.

In some embodiments, the incretin agonist or antagonist containing drug further contains an amylin mimetic. In some embodiments, the incretin agonist or antagonist containing drug further contains a GLP-2 receptor agonist.

In some embodiments, the incretin agonist or antagonist containing drug is any one of orforglipron, exenatide, exenatide LAR, liraglutide, taspoglutide, semaglutide, albiglutide, lixisenatide, tirzepatide, retatrutide, maritide, aleniglipron, efsubaglutide alfa, utreglutide, bofanglutide, dapiglutide, teduglutide, glepaglutide, apraglutide, MET-097i, MET-224o, MET-002o, MET-815i, VK2735, or dulaglutide.

In some embodiments of the method of the invention, the adverse effects comprise one or more of loss in (i) lean body mass, fat free mass, or muscle mass, (ii) muscle strength, (iii) physical function, (iv) bone strength, or (v) bone mass or density. In some embodiments, the loss in lean body mass is from about 3% to 60% of the total body weight in the subject. In some embodiments, the loss in lean body mass is from about 3% to 20% of the total body weight in the subject.

In some embodiments, the method of the invention prevents, reduces, or treats rebound of one or more of weight gain, fat mass gain, lean mass loss, or muscle strength or physical function loss when the weight loss drug is discontinued.

In some embodiments, the method of the invention results in one or more of (i) reducing the loss of lean body mass or gaining lean body mass (muscle mass) in the subject, (ii) preventing or reversing bone loss or gaining bone in the subject, (iii) overcoming or improving insulin resistance in the subject, and (iv) improving HbA1c in the subject.

In some embodiments, the method of the invention results in one or more of reducing abdominal, subcutaneous, or intramuscular fat accumulation, improving body composition, lowering body fat content, lowering fat mass, improving blood lipid profile, increasing or preserving muscle mass or muscle strength or muscle physical function, increasing bone mass or bone mineral density (BMD) or bone strength or bone function, and lowering HbA1c in the subject.

In some embodiments, the method of the invention results in preservation or restoration of lean body mass (LBM) or muscle in the subject. In some embodiments, the method maintains fat loss or prevents fat regain. In some embodiments, the subject may or may not have pre-diabetes or diabetes.

In some embodiments, the method of the invention prevents, reduces, or treats muscle weakness, poor balance, decreased gait speed, mobility disability, loss of independence, increased risk of falls, bone fractures, loss of physical function, physical disability, poor quality of life, high hospitalization rates, and/or increased mortality in the subject.

In some embodiments, the bone fractures are fractures of the hip or pelvis in the subject.

In some embodiments of the method of the invention, the SARM compound is administered to the subject concurrently with, or prior to, or after the treatment with the weight loss drug.

In some embodiments, the SARM compound is administered at a dose of from 0.1 mg to 50 mg per day, or wherein the SARM compound is administered at a dose of 0.1 mg per day, 0.3 mg per day, 1 mg per day, 3 mg per day, 6 mg per day, 9 mg per day, or 18 mg per day, and/or intermediate doses.

In some embodiments, the method of the invention prevents, reduces, or treats lean mass loss in a subject who is under treatment or stops treatment with the weight loss drug. In some embodiments, the method further improves physical function. In some embodiments, the method of the invention decreases fat mass while preserving or increasing lean mass in the subject. In some embodiments, the method of the invention further prevents, reduces, and treats muscle weakness, poor balance, decreased gait speed, mobility disability, loss of independence, increased risk of falls, bone fractures, loss of physical function, physical disability, poor quality of life, high hospitalization rates, and/or increased mortality in the subject. In some embodiments, the bone fractures are fractures of the hip or pelvis in the subject. In some embodiments, (1) the subject has sarcopenic obesity, and/or (2) the subject is 60 years old or older. In some embodiments, the subject has pre-diabetes or diabetes, and is other embodiments, the subject does not have pre-diabetes or diabetes. In some embodiments, the weight loss drug is an incretin agonist or antagonist containing drug. In some embodiments, the incretin agonist or antagonist containing drug is a GLP-1 receptor agonist. In some embodiments, the incretin agonist or antagonist containing drug is orforglipron, exenatide, exenatide LAR, liraglutide, taspoglutide, semaglutide, albiglutide, lixisenatide, tirzepatide, retatrutide, aleniglipron, efsubaglutide alfa, utreglutide, bofanglutide, dapiglutide, teduglutide, glepaglutide, apraglutide, MET-097i, MET-224o, MET-002o, MET-815i, or dulaglutide. In some embodiments, the incretin agonist or antagonist containing drug is semaglutide, tirzepatide, or orforglipron. In some embodiments, semaglutide, tirzepatide, or orforglipron is a GLP-1 RA.

In another aspect, the present invention provides a method for decreasing fat mass while preserving or increasing lean mass in a subject who is under treatment or stops treatment with the weight loss drug, comprising administering to the subject a therapeutically effective amount of a selective androgen receptor modulator (SARM) compound represented by a structure of Formula I:

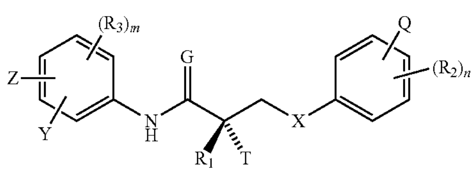

I wherein

X is a bond, O, $CH_2$, NH, S, Se, PR, NO, or NR;

G is O or S;

T is OH, OR, —$NHCOCH_3$, or NHCOR;

R is alkyl, haloalkyl, dihaloalkyl, trihaloalkyl, $CH_2F$, $CHF_2$, $CF_3$, $CF_2CF_3$, aryl, phenyl, halogen, alkenyl, or OH;

$R_1$ is $CH_3$, $CH_2F$, $CHF_2$, $CF_3$, $CH_2CH_3$, or $CF_2CF_3$;

$R_2$ is H, F, Cl, Br, I, $CH_3$, $CF_3$, OH, CN, $NO_2$, $NHCOCH_3$, $NHCOCF_3$, NHCOR, alkyl, arylalkyl, OR, $NH_2$, NHR, $N(R)_2$, or SR;

$R_3$ is H, F, Cl, Br, I, CN, $NO_2$, COR, COOH, CONHR, $CF_3$, or $Sn(R)_3$, or $R_3$ together with the benzene ring to which it is attached forms a fused ring system represented by the structure:

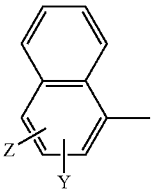

or

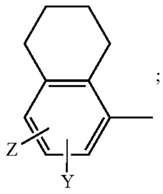

;

Z is $NO_2$, CN, COR, COOH, or CONHR;

Y is $CF_3$, F, Br, Cl, I, CN, or $Sn(R)_3$;

Q is CN, alkyl, halogen, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, or SR;

or Q together with the benzene ring to which it is attached is a fused ring system represented by structure A, B, or C:

A

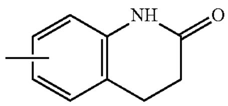

B

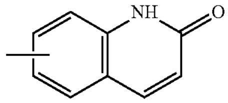

C

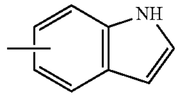

;

n is an integer of 1-4; and m is an integer of 1-3, or an optical isomer, a racemic mixture, a pharmaceutically acceptable salt, a pharmaceutical product, a hydrate, an N-oxide, or a crystal thereof.

In another embodiment, the SARM compound used in the above method is represented by a structure of Formula II:

II

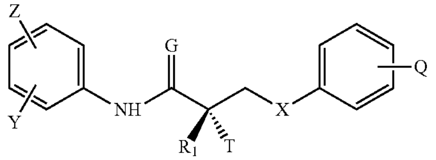

wherein

X is a bond, O, $CH_2$, NH, Se, PR, or NR;

G is O or S;

T is OH, OR, —$NHCOCH_3$, or NHCOR;

Z is $NO_2$, CN, COR, COOH, or CONHR;

Y is I, $CF_3$, Br, Cl, or $Sn(R)_3$;

Q is CN, alkyl, halogen, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, or SR;

or Q together with the benzene ring to which it is attached is a fused ring system represented by structure A, B, or C:

A

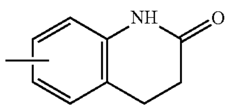

B

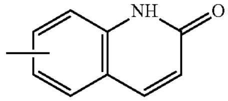

C

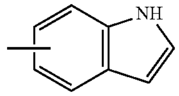

;

R is a $C_1$-$C_4$ alkyl, aryl, phenyl, alkenyl, hydroxyl, a $C_1$-$C_4$ haloalkyl, halogen, or haloalkenyl; and $R_1$ is $CH_3$, $CF_3$, $CH_2CH_3$, or $CF_2CF_3$.

In one embodiment, the SARM compound is represented by a structure of Formulas VIII, IX, X, XI, XII, XIII, and XIV:

VIII

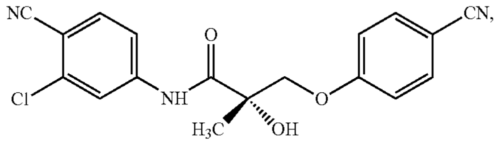

IX

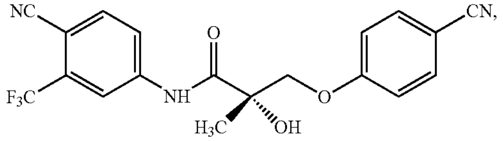

X

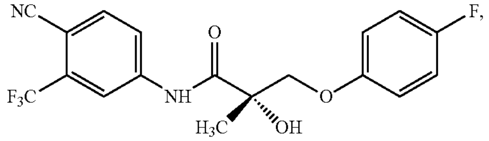

XI

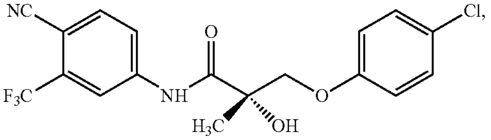

XII

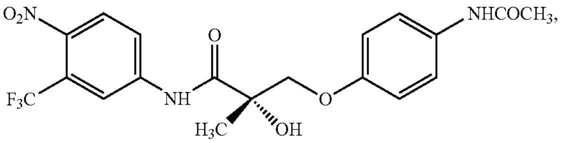

XIII

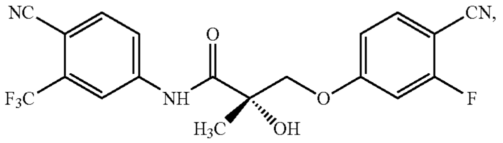

or

XIV

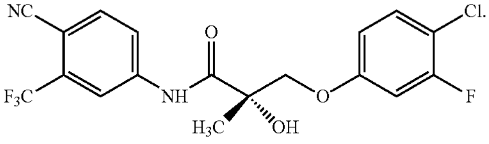

In one embodiment, the SARM compound is represented by a structure of Formula IX,

IX

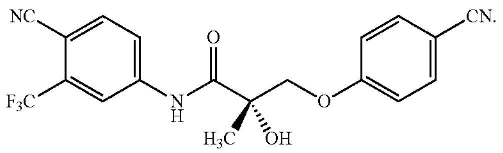

In some embodiments of the method of the invention, the subject has sarcopenic obesity. In other embodiments, the subject is 60 years old or older. In certain embodiments, the subject has sarcopenic obesity and is 60 years old or older.

In some embodiments, the weight loss drug is an incretin agonist or antagonist containing drug, wherein the incretin agonist or antagonist is a glucagon-like peptide-1 (GLP-1) receptor agonist, and/or a glucagon-like peptide-2 (GLP-2) receptor agonist, and/or a glucose-dependent insulinotropic polypeptide (GIP) antagonist or a GIP agonist, and/or a glucagon agonist, and/or an amylin agonist, and/or an oxyntomodulin agonist, or any combination thereof.

In some embodiments, the incretin agonist or antagonist containing drug is a GLP-1 receptor agonist. In some embodiments, the incretin agonist or antagonist containing drug is a GLP-2 receptor agonist (GLP-2 RA). In some embodiments, the incretin agonist or antagonist containing drug is a GLP-1 RA and a GIP agonist. In some embodiments, the incretin agonist or antagonist containing drug is a GLP-1 RA and a GIP antagonist. In some embodiments, the incretin agonist or antagonist containing drug is a GLP-1 RA and a GIP agonist and a glucagon agonist. In some embodiments, the incretin agonist or antagonist containing drug is a GLP-1 RA and an amylin agonist. In some cases, a single molecule possesses more than one type of incretin activity. In some cases, multiple molecules are used to achieve multiple types of weight loss and/or incretin activity including antagonism.

In some embodiments, the incretin agonist or antagonist containing drug further contains an amylin mimetic. In some embodiments, the incretin agonist or antagonist containing drug further contains a GLP-2 RA.

In some embodiments, the incretin agonist or antagonist containing drug is any one of orforglipron, exenatide, exenatide LAR, liraglutide, taspoglutide, semaglutide, albiglutide, lixisenatide, tirzepatide, retatrutide, maritide, aleniglipron, efsubaglutide alfa, utreglutide, bofanglutide, dapiglutide, teduglutide, glepaglutide, apraglutide, MET-097i, MET-224o, MET-002o, MET-815i, VK2735, or dulaglutide. In some embodiments, the incretin agonist or antagonist containing drug is semaglutide. In some embodiments, semaglutide is a GLP-1 RA. In certain embodiments, the GLP-1 receptor agonist is semaglutide. In certain embodiments, the incretin agonist or antagonist containing drug is tirzepatide. In certain embodiments, the incretin agonist or antagonist containing drug is orforglipron.

In some embodiments, the incretin agonist or antagonist containing drug is semaglutide and the SARM is Formula IX.

In some embodiments of the method of the invention, the SARM compound is administered to the subject concurrently with, or prior to, or after the treatment with the weight loss drug.

In some embodiments, the SARM compound is administered at a dose of from 0.1 mg to 50 mg per day, or wherein the SARM compound is administered at a dose of 0.1 mg per day, 0.3 mg per day, 1 mg per day, 3 mg per day, 6 mg per day, 9 mg per day, or 18 mg per day, and/or intermediate doses.

In another aspect, the present invention provides a method for decreasing fat mass while preserving or increasing lean mass in a subject who is under treatment or stops treatment with an incretin agonist or antagonist containing drug, comprising administering to the subject a therapeutically effective amount of a selective androgen receptor modulator (SARM) compound represented by a structure of Formula IX,

IX

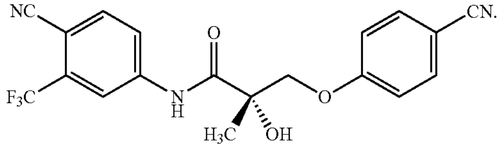

In some embodiments of the method of the invention, the subject has sarcopenic obesity, and/or the subject is 60 years old or older. In some embodiments, the incretin agonist or antagonist containing drug is a GLP-1 receptor agonist. In some embodiments, the incretin agonist or antagonist containing drug is a GLP-2 receptor agonist. In some embodiments, the incretin agonist or antagonist containing drug is orforglipron, exenatide, exenatide LAR, liraglutide, taspoglutide, semaglutide, albiglutide, lixisenatide, tirzepatide, retatrutide, aleniglipron, efsubaglutide alfa, utreglutide, bofanglutide, dapiglutide, teduglutide, glepaglutide, apraglutide, MET-097i, MET-224o, MET-002o, MET-815i, or dulaglutide. In certain embodiments, the incretin agonist or antagonist containing drug is semaglutide. In some embodiments, semaglutide is a GLP-1 RA.

In a further aspect, the present invention provides a method of preventing, reducing, or treating lean mass loss in a subject who has discontinued treatment with an incretin agonist or antagonist containing drug, comprising administering to the subject a therapeutically effective amount of a selective androgen receptor modulator (SARM) compound represented by a structure of Formula I:

I

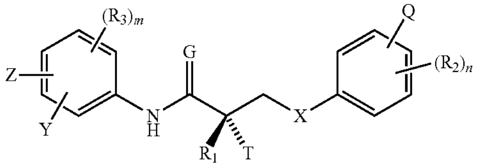

wherein

X is a bond, O, $CH_2$, NH, S, Se, PR, NO, or NR;

G is O or S;

T is OH, OR, —$NHCOCH_3$, or NHCOR;

R is alkyl, haloalkyl, dihaloalkyl, trihaloalkyl, $CH_2F$, $CHF_2$, $CF_3$, $CF_2CF_3$, aryl, phenyl, halogen, alkenyl, or OH;

$R_1$ is $CH_3$, $CH_2F$, $CHF_2$, $CF_3$, $CH_2CH_3$, or $CF_2CF_3$;

$R_2$ is H, F, Cl, Br, I, $CH_3$, $CF_3$, OH, CN, $NO_2$, $NHCOCH_3$, $NHCOCF_3$, NHCOR, alkyl, arylalkyl, OR, $NH_2$, NHR, $N(R)_2$, or SR;

$R_3$ is H, F, Cl, Br, I, CN, $NO_2$, COR, COOH, CONHR, $CF_3$, or $Sn(R)_3$, or $R_3$ together with the benzene ring to which it is attached forms a fused ring system represented by the structure:

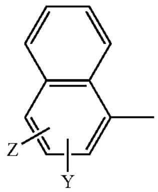

or

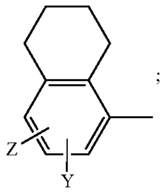

;

Z is $NO_2$, CN, COR, COOH, or CONHR;

Y is $CF_3$, F, Br, Cl, I, CN, or $Sn(R)_3$;

Q is CN, alkyl, halogen, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, or SR;

or Q together with the benzene ring to which it is attached is a fused ring system represented by structure A, B, or C:

A

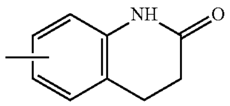

B

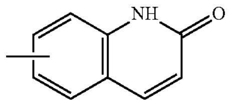

C

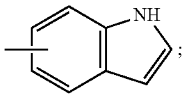

n is an integer of 1-4; and m is an integer of 1-3, or an optical isomer, a racemic mixture, a pharmaceutically acceptable salt, a pharmaceutical product, a hydrate, an N-oxide, or a crystal thereof.

In another embodiment, the SARM compound used in the above method is represented by a structure of Formula II:

II

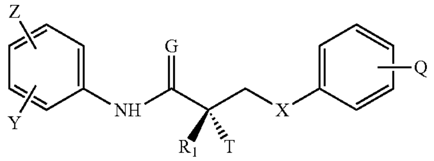

wherein

X is a bond, O, $CH_2$, NH, Se, PR, or NR;

G is O or S;

T is OH, OR, —$NHCOCH_3$, or NHCOR;

Z is $NO_2$, CN, COR, COOH, or CONHR;

Y is I, $CF_3$, Br, Cl, or $Sn(R)_3$;

Q is CN, alkyl, halogen, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, or SR;

or Q together with the benzene ring to which it is attached is a fused ring system represented by structure A, B, or C:

A

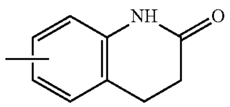

-continued

B

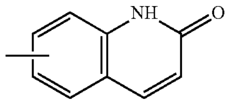

C

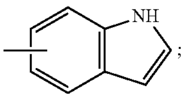

R is a $C_1$-$C_4$ alkyl, aryl, phenyl, alkenyl, hydroxyl, a $C_1$-$C_4$ haloalkyl, halogen, or haloalkenyl; and $R_1$ is $CH_3$, $CF_3$, $CH_2CH_3$, or $CF_2CF_3$.

In one embodiment, the SARM compound is represented by a structure of Formulas VIII, IX, X, XI, XII, XIII, and XIV:

VIII

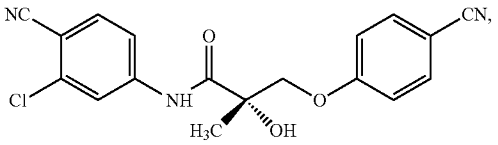

IX

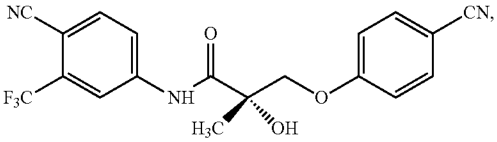

X

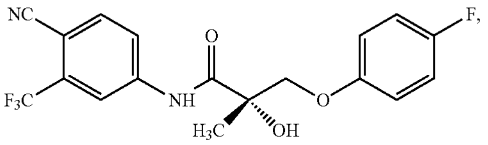

XI

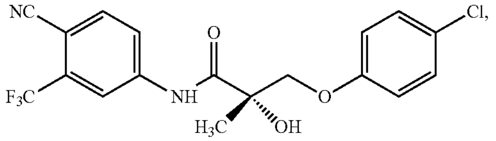

XII

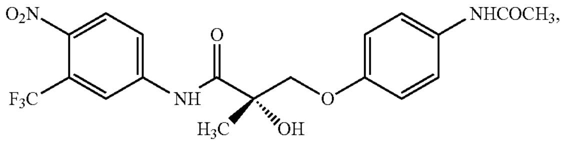

XIII

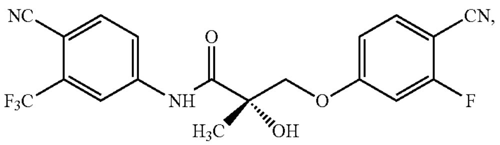

or

XIV

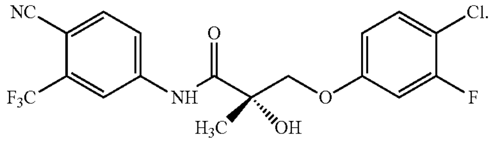

In one embodiment, the SARM compound is represented by a structure of Formula IX,

IX

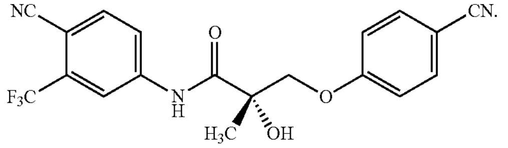

In some embodiments of the method of the invention, the SARM compound is administered to the subject concurrently with, prior to, or after the treatment with the incretin agonist or antagonist containing drug. In some embodiments, the incretin agonist or antagonist containing drug is a GLP-1 receptor agonist. In some embodiments, the incretin agonist or antagonist containing drug is a GLP-2 receptor agonist. In certain embodiments, the GLP-1 receptor agonist is semaglutide. In certain embodiments, the GLP-1 receptor agonist is tirzepatide. In certain embodiments, the GLP-1 receptor agonist is orforglipron. In some embodiments, the subject is administered a therapeutically effective amount of the incretin agonist or antagonist containing drug as monotherapy before the SARM is administered. In some embodiments, fat mass gain is further prevented, reduced, or treated in the subject. In other embodiments, total body weight gain is further prevented, reduced, or treated in the subject. In some embodiments, muscle weakness or physical function decline is further prevented, reduced or treated in the subject.

In some embodiments, the SARM compound is administered at a dose of from 0.1 mg to 50 mg per day, or wherein the SARM compound is administered at a dose of 0.1 mg per day, 0.3 mg per day, 1 mg per day, 3 mg per day, 6 mg per day, 9 mg per day, or 18 mg per day.

In a further aspect, the present invention provides a method for preventing, reducing, or treating lean mass loss and muscle weakness or physical function decline in a subject who has discontinued treatment with an incretin agonist or antagonist containing drug, comprising administering to the subject a therapeutically effective amount of a selective androgen receptor modulator (SARM) compound represented by a structure of Formula I.

I

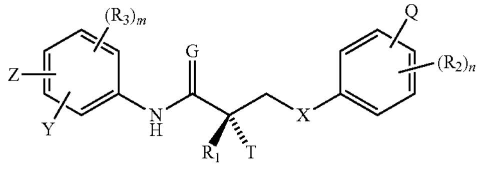

wherein

X is a bond, O, $CH_2$, NH, S, Se, PR, NO, or NR;

G is O or S;

T is OH, OR, —$NHCOCH_3$, or NHCOR;

R is alkyl, haloalkyl, dihaloalkyl, trihaloalkyl, $CH_2F$, $CHF_2$, $CF_3$, $CF_2CF_3$, aryl, phenyl, halogen, alkenyl, or OH;

$R_1$ is $CH_3$, $CH_2F$, $CHF_2$, $CF_3$, $CH_2CH_3$, or $CF_2CF_3$;

$R_2$ is H, F, Cl, Br, I, $CH_3$, $CF_3$, OH, CN, $NO_2$, $NHCOCH_3$, $NHCOCF_3$, NHCOR, alkyl, arylalkyl, OR, $NH_2$, NHR, $N(R)_2$, or SR;

$R_3$ is H, F, Cl, Br, I, CN, $NO_2$, COR, COOH, CONHR, $CF_3$, or $Sn(R)_3$, or $R_3$ together with the benzene ring to which it is attached forms a fused ring system represented by the structure:

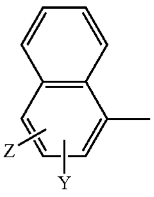
or
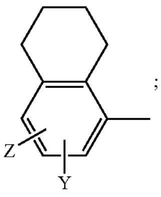
;

Z is $NO_2$, CN, COR, COOH, or CONHR;

Y is $CF_3$, F, Br, Cl, I, CN, or $Sn(R)_3$;

Q is CN, alkyl, halogen, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, or SR;

or Q together with the benzene ring to which it is attached is a fused ring system represented by structure A, B, or C:

A

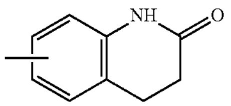

B

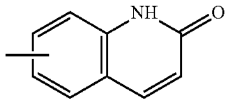

C

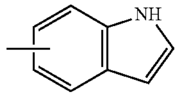
;

n is an integer of 1-4; and m is an integer of 1-3, or an optical isomer, a racemic mixture, a pharmaceutically acceptable salt, a pharmaceutical product, a hydrate, an N-oxide, or a crystal thereof.

In another embodiment, the SARM compound used in the above method is represented by a structure of Formula II:

II

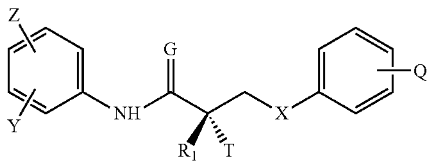

wherein

X is a bond, O, $CH_2$, NH, Se, PR, or NR;

G is O or S;

T is OH, OR, —$NHCOCH_3$, or NHCOR;

Z is $NO_2$, CN, COR, COOH, or CONHR;

Y is I, $CF_3$, Br, Cl, or $Sn(R)_3$;

Q is CN, alkyl, halogen, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, or SR;

or Q together with the benzene ring to which it is attached is a fused ring system represented by structure A, B, or C:

A

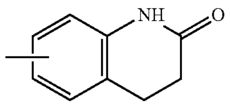

B

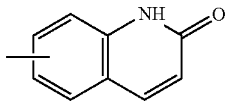

C

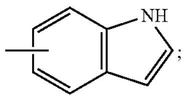

R is a $C_1$-$C_4$ alkyl, aryl, phenyl, alkenyl, hydroxyl, a $C_1$-$C_4$ haloalkyl, halogen, or haloalkenyl; and $R_1$ is $CH_3$, $CF_3$, $CH_2CH_3$, or $CF_2CF_3$.

In one embodiment, the SARM compound is represented by a structure of Formulas VIII, IX, X, XI, XII, XIII, and XIV:

VIII

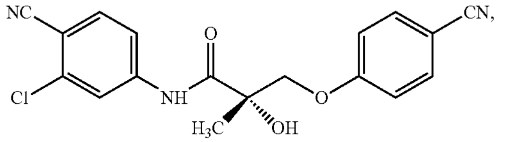

IX

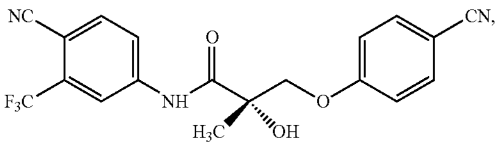

X

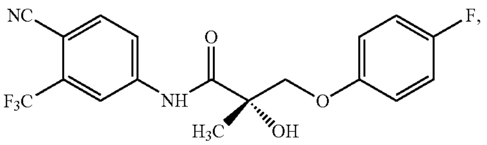

XI

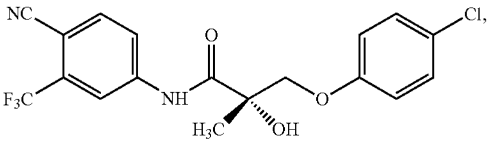

XII

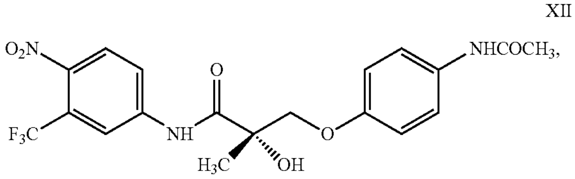

XIII

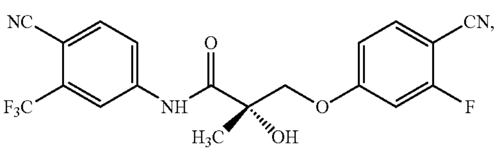

or

-continued

XIV

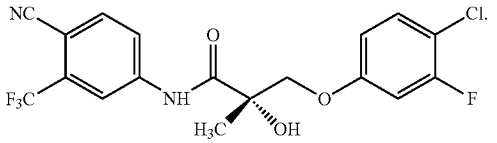

In one embodiment, the SARM compound is represented by a structure of Formula IX,

IX

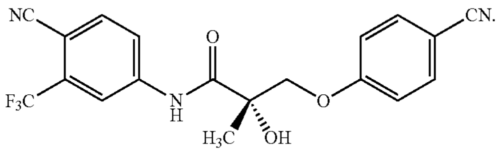

In some embodiments, the SARM compound is administered to the subject concurrently with, prior to, or after the treatment with the incretin agonist or antagonist containing drug. In some embodiments, the incretin agonist or antagonist containing drug is a GLP-1 receptor agonist. In some embodiments, the GLP-1 receptor agonist is semaglutide. In some embodiments, the subject is administered a therapeutically effective amount of the incretin agonist or antagonist containing drug as monotherapy before the SARM is administered. In some embodiments, fat mass gain is further prevented, reduced, or treated in the subject. In some embodiments, total body weight gain is further prevented, reduced, or treated in the subject.

In some embodiments, the SARM compound is administered at a dose of from 0.1 mg to 50 mg per day, or wherein the SARM compound is administered at a dose of 0.1 mg per day, 0.3 mg per day, 1 mg per day, 3 mg per day, 6 mg per day, 9 mg per day, or 18 mg per day.

In a further aspect, the present invention provides a method for maintenance or improvement of body composition in a subject who is under treatment or stops treatment with a weight loss drug, comprising administering to the subject a therapeutically effective amount of a selective androgen receptor modulator (SARM) compound, or an optical isomer, a racemic mixture, a pharmaceutically acceptable salt, a pharmaceutical product, a hydrate, an N-oxide, or a crystal thereof, wherein the selective androgen receptor modulator (SARM) compound is represented by a structure of Formula I:

I

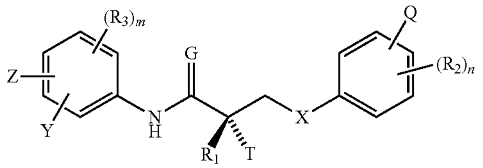

wherein

X is a bond, O, $CH_2$, NH, S, Se, PR, NO, or NR;

G is O or S;

T is OH, OR, —$NHCOCH_3$, or NHCOR;

R is alkyl, haloalkyl, dihaloalkyl, trihaloalkyl, $CH_2F$, $CHF_2$, $CF_3$, $CF_2CF_3$, aryl, phenyl, halogen, alkenyl, or OH;

$R_1$ is $CH_3$, $CH_2F$, $CHF_2$, $CF_3$, $CH_2CH_3$, or $CF_2CF_3$;

$R_2$ is H, F, Cl, Br, I, $CH_3$, $CF_3$, OH, CN, $NO_2$, $NHCOCH_3$, $NHCOCF_3$, NHCOR, alkyl, arylalkyl, OR, $NH_2$, NHR, $N(R)_2$, or SR;

$R_3$ is H, F, Cl, Br, I, CN, $NO_2$, COR, COOH, CONHR, $CF_3$, or $Sn(R)_3$, or $R_3$ together with the benzene ring to which it is attached forms a fused ring system represented by the structure:

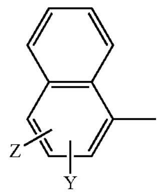

or

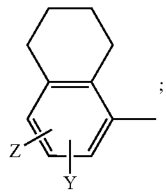

;

Z is $NO_2$, CN, COR, COOH, or CONHR;

Y is $CF_3$, F, Br, Cl, I, CN, or $Sn(R)_3$;

Q is CN, alkyl, halogen, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, or SR;

or Q together with the benzene ring to which it is attached is a fused ring system represented by structure A, B, or C:

A

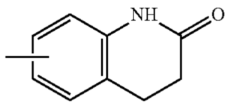

B

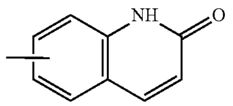

C

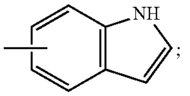

;

n is an integer of 1-4; and m is an integer of 1-3, or an optical isomer, a racemic mixture, a pharmaceutically acceptable salt, a pharmaceutical product, a hydrate, an N-oxide, or a crystal thereof.

In another embodiment, the SARM compound used in the above method is represented by a structure of Formula II:

II

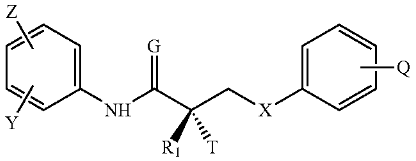

wherein

X is a bond, O, $CH_2$, NH, Se, PR, or NR;

G is O or S;

T is OH, OR, —$NHCOCH_3$, or NHCOR;

Z is $NO_2$, CN, COR, COOH, or CONHR;

Y is I, $CF_3$, Br, Cl, or $Sn(R)_3$;

Q is CN, alkyl, halogen, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, or SR;

or Q together with the benzene ring to which it is attached is a fused ring system represented by structure A, B, or C:

A

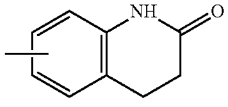

B

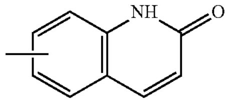

C

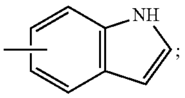

;

R is a $C_1$-$C_4$ alkyl, aryl, phenyl, alkenyl, hydroxyl, a $C_1$-$C_4$ haloalkyl, halogen, or haloalkenyl; and $R_1$ is $CH_3$, $CF_3$, $CH_2CH_3$, or $CF_2CF_3$.

In one embodiment, the SARM compound is represented by a structure of Formulas VIII, IX, X, XI, XII, XIII, and XIV:

VIII

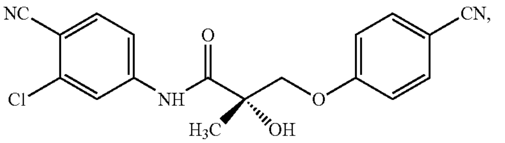

,

IX

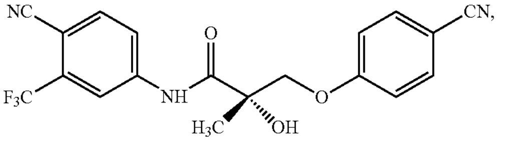

,

X

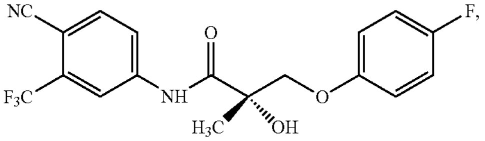

,

XI

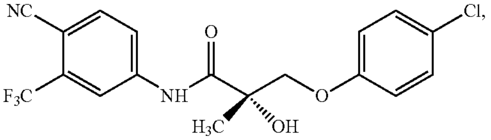

,

XII

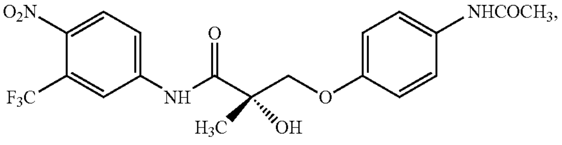

,

-continued

XIII

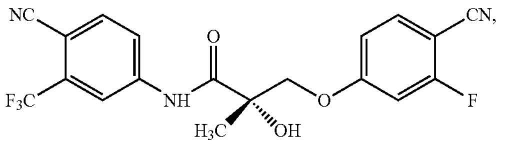

or

XIV

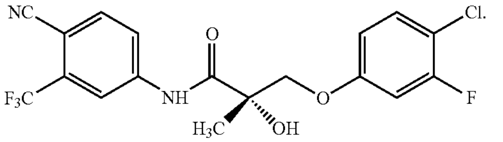

In one embodiment, the SARM compound is represented by a structure of Formula IX,

IX

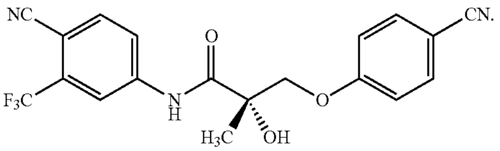

In some embodiments of the method of the invention, the weight loss drug is an incretin agonist or antagonist containing drug. In some embodiments, the incretin agonist or antagonist containing drug is a glucagon-like peptide-1 (GLP-1) receptor agonist, a glucose-dependent insulinotropic polypeptide (GIP) antagonist, a GIP agonist, and/or a glucagon agonist, and/or a glucagon-like peptide-2 (GLP-2) receptor agonist, and/or an amylin agonist, and/or oxyntomodulin agonist, or any combination thereof. In some embodiments, the incretin agonist or antagonist containing drug is a GLP-1 receptor agonist. In some embodiments, the incretin agonist or antagonist containing drug is a GLP-1 RA and a GIP agonist.

In some embodiments, the incretin agonist or antagonist containing drug is a GLP-1 RA and a GIP antagonist. In some embodiments, the incretin agonist or antagonist containing drug is a GLP-1 RA and a GIP agonist and a glucagon agonist. In some embodiments, the incretin agonist or antagonist containing drug is a GLP-1 RA and an amylin agonist. In some cases, a single molecule possesses more than one type of incretin activity. In some cases, multiple molecules are used to achieve multiple types of incretin activity including antagonism. In some cases, a single molecule is used to achieve any one of the activities above. In some embodiments, the incretin agonist or antagonist containing drug further contains an amylin mimetic. In some embodiments, the incretin agonist or antagonist containing drug is any one of orforglipron, exenatide, exenatide LAR, liraglutide, taspoglutide, semaglutide, albiglutide, lixisenatide, tirzepatide, retatrutide, maritide, aleniglipron, efsubaglutide alfa, utreglutide, bofanglutide, dapiglutide, teduglutide, glepaglutide, apraglutide, MET-097i, MET-224o, MET-002o, MET-815i, VK2735, or dulaglutide, or wherein the incretin agonist or antagonist containing drug is semaglutide.

In some embodiments, the SARM compound is administered to the subject concurrently with, prior to, or after the treatment with the incretin agonist or antagonist containing drug. In some embodiments, the incretin agonist or antagonist containing drug is a GLP-1 receptor agonist. In some embodiments, the GLP-1 receptor agonist is semaglutide. In some embodiments, the subject is administered a therapeutically effective amount of the incretin agonist or antagonist containing drug as monotherapy before the SARM is administered. In some embodiments, fat mass gain is further prevented, reduced, or treated in the subject. In some embodiments, total body weight gain is further prevented, reduced, or treated in the subject. In some embodiments, physical function is further maintained or improved. In some embodiments, the method prevents, reduces, or treats rebound of one or more of weight gain, fat mass gain, lean mass loss, and muscle strength or physical function loss when the GLP-1 receptor agonist is discontinued. In some embodiments, the method results in preservation or restoration of lean body mass (LBM) or muscle in the subject. In some embodiments, the method maintains fat loss or prevents fat regain.

In some embodiments of the method of the invention, the incretin agonist or antagonist containing drug is semaglutide and the SARM is Formula IX.

In some embodiments of the method of the invention, the improved body composition is represented by further decreasing fat mass while preserving or increasing lean mass in a subject who is under treatment with the co-administered weight loss drug and the SARM compound, relative to a subject who is under treatment with the weight loss drug alone. In some embodiments, the physical function or muscle strength is maintained or improved. In some embodiments, the weight loss drug is semaglutide and the SARM is Formula IX.

In some embodiments of the method of the invention, the subject has sarcopenic obesity. In some embodiments, the subject is 60 years old or older. In other embodiments, the subject has sarcopenic obesity and is 60 years old or older.

In some embodiments, the SARM compound is administered at a dose of from 0.1 mg to 50 mg per day, or wherein the SARM compound is administered at a dose of 0.1 mg per day, 0.3 mg per day, 1 mg per day, 3 mg per day, 6 mg per day, 9 mg per day, or 18 mg per day.

In a further aspect, the present invention provides a method for maintenance or improvement of body composition in a subject who has discontinued treatment with a weight loss drug, comprising administering to the subject a therapeutically effective amount of a selective androgen receptor modulator (SARM), or an optical isomer, a racemic mixture, a pharmaceutically acceptable salt, a pharmaceutical product, a hydrate, an N-oxide, or a crystal thereof, wherein the selective androgen receptor modulator (SARM) compound is represented by a structure of Formula I:

I

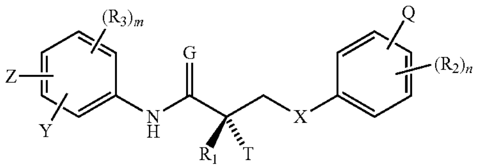

wherein

X is a bond, O, $CH_2$, NH, S, Se, PR, NO, or NR;

G is O or S;

T is OH, OR, —$NHCOCH_3$, or NHCOR;

R is alkyl, haloalkyl, dihaloalkyl, trihaloalkyl, $CH_2F$, $CHF_2$, $CF_3$, $CF_2CF_3$, aryl, phenyl, halogen, alkenyl, or OH;

$R_1$ is $CH_3$, $CH_2F$, $CHF_2$, $CF_3$, $CH_2CH_3$, or $CF_2CF_3$;

$R_2$ is H, F, Cl, Br, I, $CH_3$, $CF_3$, OH, CN, $NO_2$, $NHCOCH_3$, $NHCOCF_3$, NHCOR, alkyl, arylalkyl, OR, $NH_2$, NHR, $N(R)_2$, or SR;

$R_3$ is H, F, Cl, Br, I, CN, $NO_2$, COR, COOH, CONHR, $CF_3$, or $Sn(R)_3$, or $R_3$ together with the benzene ring to which it is attached forms a fused ring system represented by the structure:

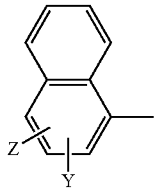
or
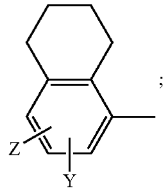
;

Z is $NO_2$, CN, COR, COOH, or CONHR;

Y is $CF_3$, F, Br, Cl, I, CN, or $Sn(R)_3$;

Q is CN, alkyl, halogen, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, or SR;

or Q together with the benzene ring to which it is attached is a fused ring system represented by structure A, B, or C:

A

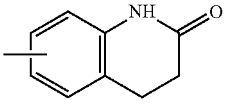

B

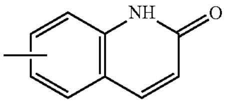

C

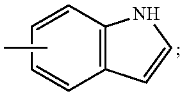

n is an integer of 1-4; and m is an integer of 1-3, or an optical isomer, a racemic mixture, a pharmaceutically acceptable salt, a pharmaceutical product, a hydrate, an N-oxide, or a crystal thereof.

In another embodiment, the SARM compound used in the above method is represented by a structure of Formula II:

II

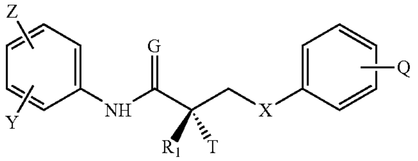

wherein

X is a bond, O, $CH_2$, NH, Se, PR, or NR;

G is O or S;

T is OH, OR, —$NHCOCH_3$, or NHCOR;

Z is $NO_2$, CN, COR, COOH, or CONHR;

Y is I, $CF_3$, Br, Cl, or $Sn(R)_3$;

Q is CN, alkyl, halogen, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, or SR;

or Q together with the benzene ring to which it is attached is a fused ring system represented by structure A, B, or C:

A

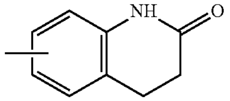

B

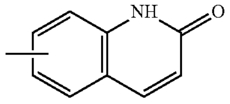

C

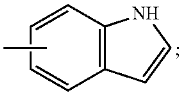

R is a $C_1$-$C_4$ alkyl, aryl, phenyl, alkenyl, hydroxyl, a $C_1$-$C_4$ haloalkyl, halogen, or haloalkenyl; and $R_1$ is $CH_3$, $CF_3$, $CH_2CH_3$, or $CF_2CF_3$.

In one embodiment, the SARM compound is represented by a structure of Formulas VIII, IX, X, XI, XII, XIII, and XIV:

VIII

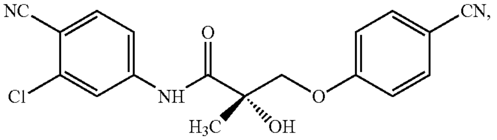

IX

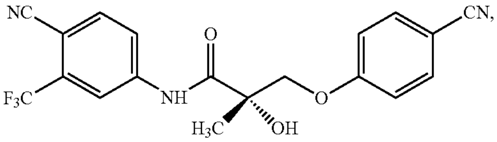

X

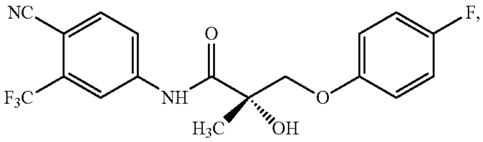

XI

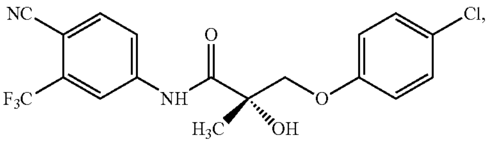

-continued

XII

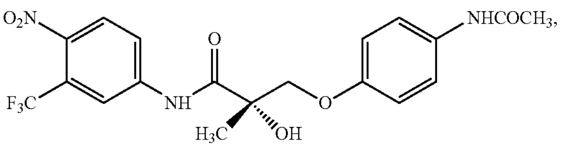

XIII

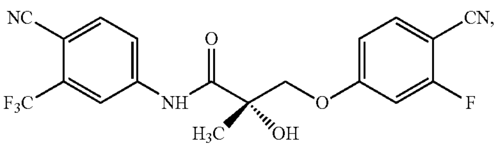

or

XIV

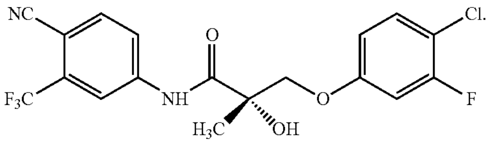

In one embodiment, the SARM compound is represented by a structure of Formula IX,

IX

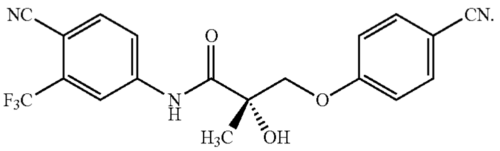

In some embodiments of the method of the invention, the weight loss drug is an incretin agonist or antagonist containing drug. In some embodiments, the incretin agonist or antagonist containing drug is a glucagon-like peptide-1 (GLP-1) receptor agonist, a glucose-dependent insulinotropic polypeptide (GIP) antagonist, a GIP agonist, and/or a glucagon agonist, and/or an amylin agonist, and/or oxyntomodulin agonist, or any combination thereof. In some embodiments, the incretin agonist or antagonist containing drug is a GLP-1 receptor agonist. In some embodiments, the incretin agonist or antagonist containing drug is a GLP-1 RA and a GIP agonist. In some embodiments, the incretin agonist or antagonist containing drug is a GLP-1 RA and a GIP antagonist. In some embodiments, the incretin agonist or antagonist containing drug is a GLP-1 RA and a GIP agonist and a glucagon agonist. In some embodiments, the incretin agonist or antagonist containing drug is a GLP-1 RA and an amylin agonist. In some cases, a single molecule possesses more than one type of incretin activity. In some cases, multiple molecules are used to achieve multiple types of incretin activity including antagonism.

In some embodiments, the SARM compound is administered to the subject concurrently with, prior to, or after the treatment with the incretin agonist or antagonist containing drug. In some embodiments, the incretin agonist or antagonist containing drug is a GLP-1 receptor agonist. In some embodiments, the GLP-1 receptor agonist is semaglutide. In some embodiments, the subject is administered a therapeutically effective amount of the incretin agonist or antagonist containing drug as monotherapy before the SARM is administered. In some embodiments, fat mass gain upon discontinuation of the incretin agonist or antagonist containing drug is further prevented, reduced, or treated in the subject. In some embodiments, total body weight gain upon discontinuation of the incretin agonist or antagonist containing drug is further prevented, reduced, or treated in the subject. In some embodiments, physical function is further maintained or improved. In some embodiments, loss of physical function is prevented, reduced or treated.

In some embodiments, the incretin agonist or antagonist containing drug is semaglutide and the SARM is Formula IX.

In some embodiments of the method of the invention, the improved body composition is represented by further decreasing fat mass while preserving or increasing lean mass in a subject who is under treatment with the co-administered weight loss drug and the SARM compound, relative to a subject who is under treatment with the weight loss drug alone. In some embodiments, the physical function or muscle strength is maintained or improved. In some embodiments, the weight loss drug is semaglutide and the SARM is Formula IX.

In some embodiments of the method of the invention, the subject has sarcopenic obesity. In some embodiments, the subject is 60 years old or older. In other embodiments, the subject has sarcopenic obesity and 60 years old or older.

In some embodiments, the SARM compound is administered at a dose of from 0.1 mg to 50 mg per day, or wherein the SARM compound is administered at a dose of 0.1 mg per day, 0.3 mg per day, 1 mg per day, 3 mg per day, 6 mg per day, 9 mg per day, or 18 mg per day.

In some embodiments of the method of the invention, the incretin agonist or antagonist containing drug is a glucagon-like peptide-1 (GLP-1) receptor agonist, a glucose-dependent insulinotropic polypeptide (GIP) antagonist, a GIP agonist, and/or a glucagon agonist, and/or an amylin agonist, and/or oxyntomodulin agonist, or any combination thereof. In some embodiments, the incretin agonist or antagonist containing drug is a GLP-1 receptor agonist. In some embodiments, the incretin agonist or antagonist containing drug is a GLP-1 RA and a GIP agonist. In some embodiments, the incretin agonist or antagonist containing drug is a GLP-1 RA and a GIP antagonist. In some embodiments, the incretin agonist or antagonist containing drug is a GLP-1 RA and a GIP agonist and a glucagon agonist. In some embodiments, the incretin agonist or antagonist containing drug is a GLP-1 RA and an amylin agonist. In some cases, a single molecule possesses more than one type of incretin activity. In some cases, multiple molecules are used to achieve multiple types of incretin activity including antagonism.

In another embodiment, the present invention provides a pharmaceutical composition having a synergistic effect, comprising an incretin agonist or antagonist containing drug and a selective androgen receptor modulator (SARM) compound, wherein the weight ratio of the incretin agonist or antagonist containing drug and the SARM compound is from 1:50 to 50:1, and wherein the SARM compound is represented by a structure of Formula I, or an optical isomer, a racemic mixture, a pharmaceutically acceptable salt, a pharmaceutical product, a hydrate, an N-oxide, or a crystal thereof, as disclosed herein. In some embodiments, the incretin agonist or antagonist containing drug is a GLP-1 receptor agonist. In some embodiments, the GLP-1 receptor agonist is semaglutide. In one embodiment, the SARM compound in the above pharmaceutical composition is represented by a structure of Formula II as disclosed herein. In other embodiments, the SARM compound in the above pharmaceutical composition is represented by one of the structures of Formulas VIII, IX, X, XI, XII, XIII, and XIV as disclosed herein.

In one embodiment, the present invention provides a method for preventing, reducing, or treating adverse effects caused by a sodium-glucose transport protein 2 (SGLT-2) inhibitor in a subject who is under treatment or stops treatment with the SGLT-2 inhibitor, comprising administering to the subject a therapeutically effective amount of a selective androgen receptor modulator (SARM) compound represented by a structure of Formula I, or an optical isomer, a racemic mixture, a pharmaceutically acceptable salt, a pharmaceutical product, a hydrate, an N-oxide, or a crystal thereof, as disclosed herein. In another embodiment, the SARM compound used in the above method is represented by a structure of Formula II as disclosed herein. In another embodiment, the SARM compound is represented by one of the structures of Formulas VIII, IX, X, XI, XII, XIII, and XIV as disclosed herein.

In another embodiment, the present invention provides a pharmaceutical composition having a synergistic effect, comprising a sodium-glucose transport protein 2 (SGLT-2) inhibitor and a selective androgen receptor modulator (SARM) compound, wherein the weight ratio of the SGLT-2 inhibitor and the SARM compound is from 1:50 to 50:1, and wherein the SARM compound is represented by a structure of Formula I, or an optical isomer, a racemic mixture, a pharmaceutically acceptable salt, a pharmaceutical product, a hydrate, an N-oxide, or a crystal thereof, as disclosed herein. In one embodiment, the SARM compound in the above pharmaceutical composition is represented by a structure of Formula II as disclosed herein. In other embodiments, the SARM compound in the above pharmaceutical composition is represented by one of the structures of Formulas VIII, IX, X, XI, XII, XIII, and XIV as disclosed herein.

In another embodiment, the present invention provides a pharmaceutical composition comprising a selective androgen receptor modulator (SARM) compound, wherein the SARM compound is represented by a structure of Formula I, or an optical isomer, a racemic mixture, a pharmaceutically acceptable salt, a pharmaceutical product, a hydrate, an N-oxide, or a crystal thereof, as disclosed herein. In one embodiment, the SARM compound in the above pharmaceutical composition is represented by a structure of Formula II as disclosed herein. In other embodiments, the SARM compound in the above pharmaceutical composition is represented by one of the structures of Formulas VIII, IX, X, XI, XII, XIII, and XIV as disclosed herein. In other embodiments, the SARM compound in the above pharmaceutical composition is represented by the structure of Formula IX as disclosed herein. In some embodiments, the selective androgen receptor modulator (SARM) compound as disclosed herein can be prepared by methods as known in the art, e.g., U.S. Pat. No. 9,604,916.

As used herein, the terms "comprise", "comprises", "comprising", "includes", "including", "having" and their conjugates mean "including but not limited to". The term "consisting of" means "including and limited to". The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a GLP-1 receptor agonist" or "at least one GLP-1 RAs" may include a plurality of GLP-1 RAs, including mixtures thereof.

Throughout this application, various embodiments of the present invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicated number and a second indicated number and "ranging/ranges from" a first indicated number "to" a second indicated number are used herein interchangeably and are meant to include the first and second indicated numbers and all the fractional and integral numerals there between.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting. Each literature reference or other citation referred to herein is incorporated herein by reference in its entirety.

In the description presented herein, each of the steps of the invention and variations thereof are described. This description is not intended to be limiting and changes in the components, sequence of steps, and other variations would be understood to be within the scope of the present invention.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

As used herein, the terms "treating" or "treatment" includes preventative as well as disorder remittive treatment. The terms "reducing", "suppressing" and "inhibiting" have their commonly understood meaning of lessening or decreasing, or delaying, or reducing, the incidence, severity or pathogenesis of a disease, disorder or condition. In one embodiment, the term treatment refers to delayed progression of, prolonged remission of, reduced incidence of, or amelioration of symptoms associated with the disease, disorder or condition. In one embodiment, the terms "treating"

"reducing", "suppressing" or "inhibiting" refer to a reduction in morbidity, mortality, or a combination thereof, in association with the indicated disease, disorder or condition. In one embodiment, the methods of treatment disclosed herein reduce the severity of the disease, or in another embodiment, symptoms associated with the disease, or in another embodiment, reduces the number of biomarkers expressed during disease.

In one embodiment, the term "treating" and its included aspects, refers to the administration to a subject with the indicated disease, disorder or condition, or in some embodiments, to a subject predisposed to the indicated disease, disorder or condition. The term "predisposed to" is to be considered to refer to, inter alia, a genetic profile or familial relationship which is associated with a trend or statistical increase in incidence, severity, etc. of the indicated disease. In some embodiments, the term "predisposed to" is to be considered to refer to a lifestyle which is associated with increased risk of the indicated disease. In some embodiments, the term "predisposed to" is to be considered to refer to the presence of biomarkers which are associated with the indicated disease.

In one embodiment, the term "administering" refers to bringing a subject in contact with a compound of the present disclosure. Administration can be accomplished in vitro, e.g. in a test tube, or in vivo, e.g. in cells or tissues of living organisms, for example humans. In some embodiments, the methods disclosed herein encompass administering the compounds of the present disclosure to a subject. In some embodiments, the present disclosure provides for the use of a SARM compound or its prodrug, analog, isomer, metabolite, derivative, pharmaceutically acceptable salt, pharmaceutical product, polymorph, crystal, impurity, N-oxide, hydrate or any combination thereof, represented by one of the structures disclosed herein.

Effective doses of the compositions of the present invention, for treating adverse effects caused by a weight loss drug, e.g., an incretin agonist or antagonist containing drug (such as a GLP-1 receptor agonist) or by a SGLT-2 inhibitor vary depending upon many different factors, including means of administration, target site, physiological state of the patient, whether the patient is human or an animal, other medications administered, and whether treatment is prophylactic or therapeutic. Usually, the patient is a human, but non-human mammals including transgenic mammals can also be treated. Treatment dosages may be titrated using routine methods known to those of skill in the art to optimize safety and efficacy. The pharmaceutical compositions of the present invention thus may include a "therapeutically effective amount." A "therapeutically effective amount" refers to an amount effective, at dosages and for periods of time necessary, to achieve the desired therapeutic result. A therapeutically effective amount of a molecule may vary according to factors such as the disease state, age, sex, and weight of the individual, and the ability of the molecule to elicit a desired response in the individual. A therapeutically effective amount is also one in which any toxic or detrimental effects of the molecule are outweighed by the therapeutically beneficial effects.

Furthermore, a skilled artisan would appreciate that the term "therapeutically effective amount" may encompass total amount of each active component of the pharmaceutical composition or method that is sufficient to show a meaningful patient benefit, i.e., treatment, healing, prevention or amelioration of the relevant medical condition, or an increase in rate of treatment, healing, prevention or amelioration of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously.

The amount of a compound of the present disclosure that will be effective in the treatment of a particular disorder or condition will depend on the nature of the disorder or condition and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test bioassays or systems generally known in the art.

In some embodiments, the compositions and methods provided herein comprise use of selective androgen receptor modulator (SARM) to prevent side effects of treatment by a weight loss drug, e.g., an incretin agonist or antagonist containing drug. In some embodiments, the compositions and methods provided herein comprise use of selective androgen receptor modulator (SARM) to prevent side effects of treatment by a GLP-1 receptor agonist (GLP-1 RA). In one embodiment, the methods and compositions disclosed herein exert beneficial effects on body composition in patients taking an incretin agonist or antagonist containing drug. In another embodiment, the methods and compositions disclosed herein allow healthy weight loss in patients taking an incretin agonist or antagonist containing drug. In another embodiment, the methods and compositions disclosed herein prevent or reduce losses of lean body mass (LBM) in patients taking an incretin agonist or antagonist containing drug. In another embodiment, the methods and compositions disclosed herein maintain or improve losses of fat body mass (FBM) in patients taking an incretin agonist or antagonist containing drug. In another embodiment, the methods and compositions disclosed herein maintain or improve losses of any fat (total body, intramuscular, visceral, or subcutaneous fat) in patients taking an incretin agonist or antagonist containing drug. In another embodiment, the methods and compositions disclosed herein prevent or reduce losses of physical function in patients taking an incretin agonist or antagonist containing drug. In another embodiment, the methods and compositions disclosed herein maintain or improve decreases in waist circumference in patients taking an incretin agonist or antagonist containing drug. In another embodiment, the methods and compositions disclosed herein prevent the loss of lean body mass (LBM) or lead to gaining lean body mass (muscle mass) in patients taking an incretin agonist or antagonist containing drug. In another embodiment, the methods and compositions disclosed herein result in a gain of lean body mass (LBM) in patients taking an incretin agonist or antagonist containing drug. In another embodiment, the methods and compositions disclosed herein result in preserving lean body mass (LBM) in patients taking incretin agonist or antagonist containing drug to prevent or reduce rebound weight gain when the incretin agonist or antagonist containing drug is discontinued. In another embodiment, the methods and compositions disclosed herein result in restoring lean body mass (LBM) in patients discontinuing an incretin agonist or antagonist containing drug to prevent or reduce the rebound regain of body weight and to maintain the weight loss by an incretin agonist or antagonist containing drug treatment. In another embodiment, the methods and compositions disclosed herein prevent the loss of strength or physical function in patients taking an incretin agonist or antagonist containing drug. In another embodiment, the methods and compositions disclosed herein prevent the reduction of muscle mass to sarcopenic, or critically low, amounts. In another embodiment, the methods and compositions disclosed herein reduce body mass index while increasing LBM in patients taking an incretin agonist or antagonist containing drug. In another embodiment, the methods and compositions disclosed herein prevent or mitigate the tendency toward sarcopenic obesity in patients taking an incretin agonist or antagonist containing drug. In some embodiments, the compositions and methods provided herein further result in a gain of lean body mass (LBM) in the subject. In some embodiments, the compositions and methods provided herein prevent, reduce, or treat muscle weakness, poor balance, decreased gait speed, mobility disability, loss of independence, increased risk of falls, bone fractures, high hospitalization rates, and increased mortality, loss of physical function, physical disability, and/or poor quality of life in the subject. In some embodiments, the compositions and methods provided herein prevent, reduce or treat bone loss and fractures in patients taking an incretin agonist or antagonist containing drug. In some embodiments, the bone fractures are fractures of the hip or pelvis in the subject. In some embodiments, the compositions and methods provided herein prevent, reduce, or treat hip or pelvic fractures in patients taking an incretin agonist or antagonist containing drug. In another embodiment, the methods and compositions disclosed herein treat or reduce obstructive sleep apnea in patients taking an incretin agonist or antagonist containing drug. In some embodiments, the compositions and methods provided herein prevent, reduce, or treat bone loss or hip or pelvic fractures in patients taking semaglutide. In some embodiments, the incretin agonist or antagonist containing drug is a GLP-1 receptor agonist. In some embodiments, the methods above employ a weight loss drug that is not an incretin agonist or antagonist containing drug. In some embodiments, methods herein comprise use of selective androgen receptor modulator (SARM) to prevent side effects of treatment by the weight loss drug.

Methods of Use in Combination with a Weight Loss Drug (e.g., an Incretin Agonist or Antagonist Containing Drug)

In one embodiment, the present invention provides a method for preventing, reducing, or treating adverse effects caused by a weight loss drug in a subject who is under treatment or stops treatment with the weight loss drug, comprising administering to the subject a therapeutically effective amount of a selective androgen receptor modulator (SARM). In some embodiments, the present invention provides a method for preventing, reducing, or treating adverse effects caused by an incretin agonist or antagonist containing drug in a subject who is under treatment or stops treatment with the incretin agonist or antagonist containing drug, comprising administering to the subject a therapeutically effective amount of a selective androgen receptor modulator (SARM). In some embodiments, the incretin agonist or antagonist containing drug is a GLP-1 receptor agonist. Examples of GLP-1 and/or GLP-2 receptor agonists include, but are not limited to, orforglipron, exenatide, exenatide LAR, liraglutide, taspoglutide, semaglutide, albiglutide, lixisenatide, tirzepatide, aleniglipron, efsubaglutide alfa, utreglutide, bofanglutide, dapiglutide, teduglutide, glepaglutide, apraglutide, MET-097i, MET-224o, MET-002o, MET-815i, or dulaglutide. In some embodiments, the GLP-1 receptor agonist is orforglipron. In some embodiments, the GLP-1 receptor agonist is exenatide. In some embodiments, the GLP-1 receptor agonist is exenatide LAR. In some embodiments, the GLP-1 receptor agonist is liraglutide. In some embodiments, the GLP-1 receptor agonist is taspoglutide. In some embodiments, the GLP-1 receptor agonist is semaglutide. In some embodiments, the GLP-1 receptor agonist is albiglutide. In some embodiments, the GLP-1 receptor agonist is lixisenatide. In some embodiments, the GLP-1 receptor agonist is tirzepatide. In some embodiments, the GLP-1 receptor agonist is aleniglipron. In some embodiments, the GLP-1 receptor agonist is efsubaglutide alfa. In some embodiments, the GLP-1 receptor agonist is utreglutide. In some embodiments, the GLP-1 receptor agonist is bofanglutide. In some embodiments, the GLP-1 receptor agonist is dapiglutide. In some embodiments, the GLP-1 receptor agonist is MET-097i. In some embodiments, the GLP-1 receptor agonist is MET-224o. In some embodiments, the GLP-1 receptor agonist is MET-002o. In some embodiments, the GLP-1 receptor agonist is MET-815i. In some embodiments, the GLP-1 receptor agonist is dulaglutide. In some embodiments, the GLP-2 receptor agonist is dapiglutide. In some embodiments, the GLP-2 receptor agonist is teduglutide. In some embodiments, the GLP-2 receptor agonist is glepaglutide. In some embodiments, the GLP-2 receptor agonist is apraglutide.

In another embodiment, the present method encompasses the use of any incretin agonist or antagonist containing drug and/or GLP-1 receptor agonists that are currently under development or those to be developed in the future; examples of GLP-1 receptor agonists include, but are not limited to, ecnoglutide (SciWind), survodutide (BI/Zealand), mazdutide (Innovent), pemvidutide (Altimmune), cotadutide (AZ), retatrutide (Eli Lilly), orforglipron (Eli Lilly), maritide (Amgen), VK2735 (Viking), CT-388 (Carmot), CT-996, GL0034 (Sun Pharma), GMA 106 (GMAX Bio.), danuglipron (Pfizer), GSBR-1290 (Structure Therapeutics), ARD-101 (Aardvark Therapeutics), ECC5004 (AstraZeneca/Eccogene), MET-097i (MetSera), ASC30 (Ascletis), HRS9531 (Hengrui), HDM1005 (Huandong Medicine), DA-1726 (MetaVia Pharma), MET-097o (MetSera), MET-224o (MetSera), NN-9662 (NovoNordisk), PF-07976016 (Pfizer), TERN-601 (Terns Pharmaceuticals), CT-868 (Roche), HS-10501 (Hansoh), KAI-9531 (Kailera), HS-10535 (Merck), HRS-7535, RGT-075, MD001, HDM1002, BGM0504, NA-931, HM15275, MWN109, MET-002o, MET-815i, and amycretin. In some embodiments, the GLP-1 receptor agonist is ecnoglutide. In some embodiments, the GLP-1 receptor agonist is survodutide. In some embodiments, the GLP-1 receptor agonist is mazdutide. In some embodiments, the GLP-1 receptor agonist is pemvidutide. In some embodiments, the GLP-1 receptor agonist is cotadutide. In some embodiments, the GLP-1 receptor agonist is retatrutide. In some embodiments, the GLP-1 receptor agonist is orforglipron. In some embodiments, the GLP-1 receptor agonist is maritide. In some embodiments, the GLP-1 receptor agonist is VK2735. In some embodiments, the GLP-1 receptor agonist is CT-388. In some embodiments, the GLP-1 receptor agonist is CT-996. In some embodiments, the GLP-1 receptor agonist is GL0034. In some embodiments, the GLP-1 receptor agonist is GMA 106. In some embodiments, the GLP-1 receptor agonist is danuglipron. In some embodiments, the GLP-1 receptor agonist is GSBR-1290. In some embodiments, the GLP-1 receptor agonist is ARD-101. In some embodiments, the GLP-1 receptor agonist is ECC5004. In some embodiments, the GLP-1 receptor agonist is MET-097i (MetSera). In some embodiments, the GLP-1 receptor agonist is ASC30 (Ascletis). In some embodiments, the GLP-1 receptor agonist is HRS9531 (Hengrui). In some embodiments, the GLP-1 receptor agonist is HDM1005 (Huandong Medicine). In some embodiments, the GLP-1 receptor agonist is DA-1726 (MetaVia Pharma). In some embodiments, the GLP-1 receptor agonist is MET-097o (MetSera). In some embodiments, the GLP-1 receptor agonist is MET-224o (MetSera). In some embodiments, the GLP-1 receptor agonist is NN-9662 (NovoNordisk). In some embodiments, the GLP-1 receptor agonist is PF-07976016 (Pfizer). In some embodiments, the GLP-1 receptor agonist is TERN-601 (Terns Pharmaceuticals). In some embodiments, the GLP-1 receptor agonist is CT-868 (Roche). In some embodiments, the GLP-1 receptor agonist is HS-10501 (Hansoh). In some embodiments, the GLP-1 receptor agonist is KAI-9531 (Kailera). In some embodiments, the GLP-1 receptor agonist is HS-10535 (Merck). In some embodiments, the GLP-1 receptor agonist is HRS-7535. In some embodiments, the GLP-1 receptor agonist is RGT-075. In some embodiments, the GLP-1 receptor agonist is MD001. In some embodiments, the GLP-1 receptor agonist is HDM1002. In some embodiments, the GLP-1 receptor agonist is BGM0504. In some embodiments, the GLP-1 receptor agonist is NA-931. In some embodiments, the GLP-1 receptor agonist is HM15275. In some embodiments, the GLP-1 receptor agonist is MWN109. In some embodiments, the GLP-1 receptor agonist is MET-002o. In some embodiments, the GLP-1 receptor agonist is MET-815i. In some embodiments, the GLP-1 receptor agonist is amycretin.

In some embodiments, the methods and compositions disclosed herein exert beneficial effects on body composition in patients taking a weight loss drug. In some embodiments, the methods and compositions disclosed herein exert beneficial effects on body composition in patients taking a weight loss drug, wherein the drug is an incretin agonist or antagonist containing drug. In some embodiments, the methods and compositions disclosed herein exert beneficial effects on body composition in patients taking an incretin agonist or antagonist containing drug, wherein the drug is a GLP-1 receptor agonist. In another embodiment, the methods and compositions disclosed herein allow healthy weight loss in patients taking a weight loss drug or incretin agonist or antagonist containing drug or a GLP-1 receptor agonist. In some embodiments, the decrease in total body weight is ≥5%, or ≥10%, or ≥15% or ≥20%. In another embodiment, the methods and compositions disclosed herein maintain or improve losses of any fat body mass (FBM) in patients taking a weight loss drug or incretin agonist or antagonist containing drug or a GLP-1 receptor agonist. In some embodiments, the decrease in FBM is ≥10%, or ≥15%, or ≥20%. In another embodiment, the methods and compositions disclosed herein maintain or improve losses of any fat (total body, intramuscular, visceral, or subcutaneous fat) in patients taking a weight loss drug or incretin agonist or antagonist containing drug or a GLP-1 RA. In another embodiment, the methods and compositions disclosed herein prevent the loss of lean body mass (LBM) or lead to gaining lean body mass (muscle mass) in patients taking a weight loss drug or incretin agonist or antagonist containing drug or a GLP-1 receptor agonist. In another embodiment, the methods and compositions disclosed herein result in a gain of lean body mass (LBM) in patients taking a weight loss drug or incretin agonist or antagonist containing drug or a GLP-1 RA. In some embodiments, the increase in LBM is ≥0%, or ≥10%, or ≥15%, or ≥20%. In another embodiment, the methods and compositions disclosed herein prevent the loss of strength or physical function in patients taking a weight loss drug or incretin agonist or antagonist containing drug or a GLP-1 receptor agonist. In some embodiments, the increase in physical function is ≥10%, or ≥15%, or ≥20%. In another embodiment, the methods and compositions disclosed herein prevent the reduction of muscle mass to sarcopenic, or critically low, amounts. In another embodiment, the methods and compositions disclosed herein reduce body mass index while increasing LBM in patients taking a weight loss drug or incretin agonist or antagonist containing drug or a GLP-1 receptor agonist. In another embodiment, the methods and compositions disclosed herein prevent or mitigate the tendency toward sarcopenic obesity in patients taking a weight loss drug or incretin agonist or antagonist containing drug or a GLP-1 receptor agonist. In some embodiments, the compositions and methods provided herein further result in a gain of lean body mass (LBM) in the subject. In some embodiments, the compositions and methods provided herein further result in a decrease in waist circumference in the subject. In another embodiment, the methods and compositions disclosed herein result in preserving lean body mass (LBM) in patients taking a weight loss drug or incretin agonist or antagonist containing drug or a GLP-1 RA, and further prevent or reduce rebound weight gain when the weight loss drug or incretin agonist or antagonist containing drug or GLP-1 RA is discontinued. In some embodiments, the methods and compositions disclosed herein result in preserving lean body mass (LBM) in patients taking a weight loss drug or incretin agonist or antagonist containing drug or a GLP-1 RA, and further prevent or reduce rebound body weight gain, fat mass gain, lean body loss, and/or muscle strength and physical function loss when the weight loss drug or incretin agonist or antagonist containing drug or a GLP-1 RA is discontinued. In another embodiment, the methods and compositions disclosed herein result in restoring lean body mass (LBM) in patients discontinuing a weight loss drug or incretin agonist or antagonist containing drug or a GLP-1 RA to prevent or reduce the rebound regain of body weight and to maintain the weight lost by GLP-1 RA treatment. In some embodiments, the compositions and methods provided herein prevent, reduce, or treat muscle weakness, poor balance, decreased gait speed, mobility disability, loss of independence, increased risk of falls, bone fractures, high hospitalization rates, and increased mortality, loss of physical function, physical disability, and/or poor quality of life in the subject. In some embodiments, the compositions and methods provided herein prevent, reduce or treat bone loss and fractures in patients taking a weight loss drug or incretin agonist or antagonist containing drug or a GLP-1 RA. In some embodiments, the bone fractures are fractures of the hip or pelvis in the subject. In some embodiments, the compositions and methods provided herein prevent, reduce, or treat hip or pelvic fractures in patients taking a weight loss drug or incretin agonist or antagonist containing drug or a GLP-1 RA. In some embodiments, the weight loss drug or incretin agonist or antagonist containing drug or GLP-1 RA is semaglutide.

In one embodiment, the present invention provides a method for preventing, reducing, or treating adverse effects caused by a glucagon-like peptide-1 (GLP-1) receptor agonist in a subject who is under treatment or stops treatment with an agent that activates GLP-1 receptor and activates or inhibits glucose-dependent insulinotropic polypeptide (GIP) receptor, comprising administering to the subject a therapeutically effective amount of a selective androgen receptor modulator (SARM). In one embodiment, an agent that can activate (or inhibit) both GLP-1 receptor and GIP receptor is tirzepatide. In one embodiment, the method comprises use of any one of the SARM compounds represented by the structure of Formula I. In another embodiment, the method comprises use of any one of the SARM compounds represented by the structure of Formula II. In another embodiment, the method comprises use of the SARM compound represented by the structure of Formula VIII. In another embodiment, the method comprises use of the SARM compound represented by the structure of Formula IX. In another embodiment, the method comprises use of the SARM compound represented by the structure of Formula X. In another embodiment, the method comprises use of the SARM compound represented by the structure of Formula XI. In another embodiment, the method comprises use of the SARM compound represented by the structure of Formula XII. In another embodiment, the method comprises use of the SARM compound represented by the structure of Formula XIII. In another embodiment, the method comprises use of the SARM compound represented by the structure of Formula XIV.

In one embodiment, the present invention provides a method for preventing, reducing, or treating lean mass loss in a subject who is under treatment or stops treatment with an incretin agonist or antagonist containing drug, comprising administering to the subject a therapeutically effective amount of a selective androgen receptor modulator (SARM). In some embodiments, the incretin agonist or antagonist containing drug is a GLP-1 receptor agonist. In some embodiments of the method, fat mass is further decreased in the subject. In some embodiments, the method decreases fat mass while preserving or increasing lean mass in the subject. In some embodiments, the method further improves physical function. In some embodiments, the subject is an obese or overweight patient. In some embodiments, the subject has prediabetes, diabetes or does not have diabetes. In some embodiments, the subject is a sarcopenic obese or overweight patient. In other embodiments, the subject is a sarcopenic obese or overweight older patient, for example, that is 60 or older than 60 years of age. In some embodiments, the subject has sarcopenic obesity. In some embodiments, the subject is 60 years old or older. In some embodiments, the method comprises use of any one of the SARM compounds represented by the structure of Formula I. In some embodiments, the method comprises use of any one of the SARM compounds represented by the structure of Formula II. In some embodiments, the method comprises use of the SARM compound represented by the structure of Formula VIII. In some embodiments, the method comprises use of the SARM compound represented by the structure of Formula IX. In some embodiments, the method comprises use of the SARM compound represented by the structure of Formula X. In some embodiments, the method comprises use of the SARM compound represented by the structure of Formula XI. In some embodiments, the method comprises use of the SARM compound represented by the structure of Formula XII. In some embodiments, the method comprises use of the SARM compound represented by the structure of Formula XIII. In some embodiments, the method comprises use of the SARM compound represented by the structure of Formula XIV.

In some embodiments, incretins are hormones that are released in response to eating and help regulate blood sugar levels. In other embodiments, incretins are produced in the upper gastrointestinal tract and include glucagon-like peptide-1 (GLP-1) and glucose-dependent insulinotropic polypeptide (GIP). In some embodiments, incretins work by stimulating insulin release, e.g., incretins cause the pancreas to release insulin, which helps regulate blood sugar levels. In other embodiments, incretins work by inhibiting glucagon release from the pancreas. In some embodiments, incretins slow digestion by slowing down the movement of food through the digestive system. In some embodiments, incretins activate gut-brain signaling to activate neurons in the hindbrain which can produce satiety and reduce how much you eat and reduce caloric intake. In some embodiments, incretin agonist or antagonist containing drugs produce GLP-1 receptor agonist effects. In some embodiments, incretin agonist or antagonist containing drugs produce GLP-2 receptor agonist effects. In some embodiments, incretin agonist or antagonist containing drugs produce GIP receptor agonism or antagonism. In some embodiments, incretin agonist or antagonist containing drugs possess multiple pharmacologies related to modulation of the activities of the hormones GLP-1, GLP-2, GIP, glucagon, amylin, and/or oxyntomodulin. In some embodiments, incretin agonist or antagonist containing drugs possess a combination of GLP-1 RA and GIP agonism or antagonism and/or glucagon agonism, and/or amylin agonism and/or oxyntomodulin agonism. In some embodiments, incretin agonist or antagonist containing drugs possessing GIP agonism or antagonism include, but are not limited to, tirzepatide, VK2735, CT-388, MET-034i, and maritide. In some embodiments, incretin agonist or antagonist containing drugs possessing glucagon agonism include, but are not limited to, MET-067i, retatrutide, mazdutide, pemvidutide, or survodutide.

In some embodiments of the methods for preventing, reducing, or treating lean mass loss in a subject receiving a glucagon-like peptide-1 (GLP-1) and/or GLP-2 receptor agonist, the GLP-1 receptor agonist is orforglipron, exenatide, exenatide LAR, liraglutide, taspoglutide, semaglutide, albiglutide, lixisenatide, tirzepatide, aleniglipron, efsubaglutide alfa, utreglutide, bofanglutide, dapiglutide, teduglutide, glepaglutide, apraglutide, MET-097i, MET-224o, MET-002o, MET-815i, or dulaglutide. In some embodiments, the GLP-1 receptor agonist is semaglutide. In some embodiments, the GLP-1 receptor agonist is orforglipron. In some embodiments, the GLP-1 receptor agonist is exenatide. In some embodiments, the GLP-1 receptor agonist is exenatide LAR. In some embodiments, the GLP-1 receptor agonist is liraglutide. In some embodiments, the GLP-1 receptor agonist is taspoglutide. In some embodiments, the GLP-1 receptor agonist is semaglutide. In some embodiments, the GLP-1 receptor agonist is albiglutide. In some embodiments, the GLP-1 receptor agonist is lixisenatide. In some embodiments, the GLP-1 receptor agonist is tirzepatide. In some embodiments, the GLP-1 receptor agonist is aleniglipron. In some embodiments, the GLP-1 receptor agonist is efsubaglutide alfa. In some embodiments, the GLP-1 receptor agonist is utreglutide. In some embodiments, the GLP-1 receptor agonist is bofanglutide. In some embodiments, the GLP-1 receptor agonist is dapiglutide. In some embodiments, the GLP-1 receptor agonist is MET-097i. In some embodiments, the GLP-1 receptor agonist is MET-224o. In some embodiments, the GLP-1 receptor agonist is MET-002o. In some embodiments, the GLP-1 receptor agonist is MET-815i. In some embodiments, the GLP-1 receptor agonist is dulaglutide. In some embodiments, the GLP-2 receptor agonist is dapiglutide. In some embodiments, the GLP-2 receptor agonist is teduglutide. In some embodiments, the GLP-2 receptor agonist is glepaglutide. In some embodiments, the GLP-2 receptor agonist is apraglutide.

In another embodiment, the present method encompasses the use of any incretin agonist or antagonist containing drug and/or GLP-1 receptor agonists that are currently under development or those to be developed in the future; examples of GLP-1 receptor agonists include, but are not limited to, ecnoglutide (SciWind), survodutide (BI/Zealand), mazdutide (Innovent), pemvidutide (Altimmune), cotadutide (AZ), retatrutide (Eli Lilly), orforglipron (Eli Lilly), maritide (Amgen), VK2735 (Viking), CT-388 (Carmot), CT-996, GL0034 (Sun Pharma), GMA 106 (GMAX Bio.), danuglipron (Pfizer), GSBR-1290 (Structure Therapeutics), ARD-101 (Aardvark Therapeutics), ECC5004 (AstraZeneca/Eccogene), MET-097i (MetSera), ASC30 (Ascletis), HRS9531 (Hengrui), HDM1005 (Huandong Medicine), DA-1726 (MetaVia Pharma), MET-097o (MetSera), MET-224o (MetSera), NN-9662 (NovoNordisk), PF-07976016 (Pfizer), TERN-601 (Terns Pharmaceuticals), CT-868 (Roche), HS-10501 (Hansoh), KAI-9531 (Kailera), HS-10535 (Merck), HRS-7535, RGT-075, MD001, HDM1002, BGM0504, NA-931, HM15275, MWN109, MET-002o, MET-815i, and amycretin.

In some embodiments, GLP-2 is an intestinal hormone that plays a crucial role in regulating intestinal growth, function, and metabolism. In some embodiments, the incretin agonist or antagonist containing drug may contain a GLP-2 receptor agonist or antagonist, or possess GLP-2 mimetic properties. In one embodiment, an example of an GLP-2 mimetic drug is dapiglutide. In other embodiments, the incretin agonist or antagonist containing drug may be combined with a GLP-2 mimetic drug. In some embodiments, examples of amylin mimetic drugs include dapiglutide, teduglutide, glepaglutide, and apraglutide.

In some embodiments, amylin is a pancreatic hormone that helps regulate blood sugar and food intake. In some embodiments, the incretin agonist or antagonist containing drug may contain an amylin mimetic drug or possess amylin mimetic properties. In one embodiment, an example of an incretin/amylin mimetic drug is amycretin. In other embodiments, the incretin agonist or antagonist containing drug may be combined with an amylin mimetic drug. In some embodiments, examples of amylin mimetic drugs include petrelintide, pramlintide, cagrilintide, eloralintide, GUBamy, MET-233i, AZD6234, and NN1213.

In some embodiments, oxyntomodulin (OXM) is a naturally occurring incretin hormone that is secreted from the intestines after eating. In some embodiments, oxyntomodulin has antidiabetic and anti-obesity properties. In some embodiments, oxyntomodulin improves glucose tolerance, promotes energy expenditure, accelerates liver lipolysis, inhibits food intake, and delays gastric emptying. In other embodiments, oxyntomodulin analogues are being developed to treat obesity and diabetes. In one embodiment, a PEGylated analogue of OXM achieves sustained release and has the potential to be developed as a treatment for diabetes and obesity. In some embodiments, these OXM analogues include, OXM3, an injectable dual-agonist that targets both the glucagon and GLP-1 receptors that is expected to help with glucose lowering and weight loss. In some embodiments, these OXM analogues include, OX-SR, a sustained-release analogue that increases energy expenditure in rats. It activates the glucagon receptor, which is essential for its effects on energy expenditure. In some embodiments, these OXM analogues include, LY3305677, an analogue that improves glycemic control and weight loss in healthy volunteers and people with type 2 diabetes.

In some embodiments, the weight loss drug is monlunabant. In some embodiments, monlunabant is an inverse agonist of the CB1 receptor. In some embodiments, the CB1 receptor plays an important role in metabolism and appetite regulation in the central nervous. In some embodiments, the CB1 receptor modulator is nimacimab, CRB-913-CB1, or AGTX-2004.

Several non-incretin weight loss drugs are FDA approved, including phentermine (Adipex, Suprenza), phentermine-topiramate (Qsymia), naltrexone-bupropion (Contrave), setmelanotide (Imcivree), orlistat (Xenical and Alli), and hydrogel (Plenity). Similar to incretin agonist or antagonist containing drugs, these drugs can cause suppression of appetite and loss of lean mass and muscle mass, leading to decreased physical function.

In one embodiment, the present invention provides a method for decreasing fat mass while preserving or increasing lean mass in a subject who is under treatment or stops treatment with an incretin agonist or antagonist containing drug, comprising administering to the subject a therapeutically effective amount of a selective androgen receptor modulator (SARM). In some embodiments, the incretin agonist or antagonist containing drug is a GLP-1 receptor agonist. In some embodiments, the GLP-1 receptor agonist is semaglutide. In some embodiments, the subject has prediabetes, diabetes or does not have diabetes. In some embodiments, the subject is an obese or overweight patient. In some embodiments, the subject is a sarcopenic obese or overweight patient. In other embodiments, the subject is a sarcopenic obese or overweight older patient, for example, that is 60 or older than 60 years of age. In some embodiments, the subject has sarcopenic obesity. In some embodiments, the subject is 60 years old or older. In some embodiments, the method comprises use of any one of the SARM compounds represented by the structure of Formula I. In some embodiments, the method comprises use of any one of the SARM compounds represented by the structure of Formula II. In some embodiments, the method comprises use of the SARM compound represented by the structure of Formula VIII. In some embodiments, the method comprises use of the SARM compound represented by the structure of Formula IX. In some embodiments, the method comprises use of the SARM compound represented by the structure of Formula X. In some embodiments, the method comprises use of the SARM compound represented by the structure of Formula XI. In some embodiments, the method comprises use of the SARM compound represented by the structure of Formula XII. In some embodiments, the method comprises use of the SARM compound represented by the structure of Formula XIII. In some embodiments, the method comprises use of the SARM compound represented by the structure of Formula XIV.

In some embodiments of the methods for decreasing fat mass while preserving or increasing lean mass in a subject who is under treatment or stops treatment with an incretin agonist or antagonist containing drug. In some embodiments, the incretin agonist or antagonist containing drug is a glucagon-like peptide-1 (GLP-1) and/or GLP-2 receptor agonist, wherein the GLP-1 receptor agonist is orforglipron, exenatide, exenatide LAR, liraglutide, taspoglutide, semaglutide, albiglutide, lixisenatide, tirzepatide, aleniglipron, efsubaglutide alfa, utreglutide, bofanglutide, dapiglutide, teduglutide, glepaglutide, apraglutide, MET-097i, MET-224o, MET-002o, MET-815i, or dulaglutide. In some embodiments, the GLP-1 receptor agonist is semaglutide. In some embodiments, the GLP-1 receptor agonist is orforglipron. In some embodiments, the GLP-1 receptor agonist is exenatide. In some embodiments, the GLP-1 receptor agonist is exenatide LAR. In some embodiments, the GLP-1 receptor agonist is liraglutide. In some embodiments, the GLP-1 receptor agonist is taspoglutide. In some embodiments, the GLP-1 receptor agonist is semaglutide. In some embodiments, the GLP-1 receptor agonist is albiglutide. In some embodiments, the GLP-1 receptor agonist is lixisenatide. In some embodiments, the GLP-1 receptor agonist is tirzepatide. In some embodiments, the GLP-1 receptor agonist is aleniglipron. In some embodiments, the GLP-1 receptor agonist is efsubaglutide alfa. In some embodiments, the GLP-1 receptor agonist is utreglutide. In some embodiments, the GLP-1 receptor agonist is bofanglutide. In some embodiments, the GLP-1 receptor agonist is dapiglutide. In some embodiments, the GLP-1 receptor agonist is MET-097i. In some embodiments, the GLP-1 receptor agonist is MET-224o. In some embodiments, the GLP-1 receptor agonist is MET-002o. In some embodiments, the GLP-1 receptor agonist is MET-815i. In some embodiments, the GLP-1 receptor agonist is dulaglutide. In some embodiments, the GLP-2 receptor agonist is dapiglutide. In some embodiments, the GLP-2 receptor agonist is teduglutide. In some embodiments, the GLP-2 receptor agonist is glepaglutide. In some embodiments, the GLP-2 receptor agonist is apraglutide.

In another embodiment, the present method encompasses the use of any GLP-1 receptor agonists that are currently under development or those to be developed in the future; examples of GLP-1 receptor agonists include, but are not limited to, ecnoglutide (SciWind), survodutide (BI/Zealand), mazdutide (Innovent), pemvidutide (Altimmune), cotadutide (AZ), retatrutide (Eli Lilly), orforglipron (Eli Lilly), maritide (Amgen), VK2735 (Viking), CT-388 (Carmot), CT-996, GL0034 (Sun Pharma), GMA 106 (GMAX Bio.), danuglipron (Pfizer), GSBR-1290 (Structure Therapeutics), ARD-101 (Aardvark Therapeutics), ECC5004 (AstraZeneca/Eccogene), MET-097i (MetSera), ASC30 (Ascletis), HRS9531 (Hengrui), HDM1005 (Huandong Medicine), DA-1726 (MetaVia Pharma), MET-097o (MetSera), MET-224o (MetSera), NN-9662 (NovoNordisk), PF-07976016 (Pfizer), TERN-601 (Terns Pharmaceuticals), CT-868 (Roche), HS-10501 (Hansoh), KAI-9531 (Kailera), HS-10535 (Merck), HRS-7535, RGT-075, MD001, HDM1002, BGM0504, NA-931, HMI5275, MWN109, MET-002o, MET-815i, and amycretin.

In one embodiment, the present invention provides a method of reducing fat body mass while preserving and/or building lean body mass in a subject, comprising administering to the subject a therapeutically effective amount of a selective androgen receptor modulator (SARM) and an incretin agonist or antagonist containing drug. In one embodiment, the present invention further provides for a method of increasing physical function in the subject with reduced fat and preserved and/or increased lean body mass, comprising administering to the subject a therapeutically effective amount of a selective androgen receptor modulator (SARM) and an incretin agonist or antagonist containing drug. In some embodiments, the present invention further provides for a method of decreasing waist circumference in the subject with reduced fat and preserved and/or increased lean body mass, comprising administering to the subject a therapeutically effective amount of a selective androgen receptor modulator (SARM) and the incretin agonist or antagonist containing drug. In some embodiments, there is a concomitant improvement in body composition, total body weight, waist circumference, and physical function. In another embodiment, the methods and compositions disclosed herein result in preserving lean body mass (LBM) in patients taking an incretin agonist or antagonist containing drug, and further prevent or reduce rebound weight gain when the incretin agonist or antagonist containing drug is discontinued. In some embodiments, the methods and compositions disclosed herein result in preserving lean body mass (LBM) in patients taking an incretin agonist or antagonist containing drug, and further prevent or reduce rebound body weight gain, fat mass gain, lean body loss, and/or muscle strength and physical function loss when the incretin agonist or antagonist containing drug is discontinued. In another embodiment, the methods and compositions disclosed herein result in restoring lean body mass (LBM) in patients discontinuing an incretin agonist or antagonist containing drug to prevent or reduce the rebound regain of body weight and to maintain the weight lost by the incretin agonist or antagonist containing drug treatment. In some embodiments, the method comprises use of any one of the SARM compounds represented by the structure of Formula I, II, VIII, IX, X, XI, XII, XIII, and XIV. In some embodiments, the subject has prediabetes, diabetes or does not have diabetes. In some embodiments, the subject is an obese or overweight patient. In some embodiments, the subject is a sarcopenic obese or overweight patient. In other embodiments, the subject is a sarcopenic obese or overweight older patient, for example, that is 60 or older than 60 years of age. In some embodiments, the subject has sarcopenic obesity. In some embodiments, the subject is 60 years old or older. In some embodiments, the incretin agonist or antagonist containing drug is a GLP-1 receptor agonist. In some embodiments, the incretin agonist or antagonist containing drug is a GLP-2 receptor agonist. In some embodiments, the GLP-1 receptor agonist is orforglipron, exenatide, exenatide LAR, liraglutide, taspoglutide, semaglutide, albiglutide, lixisenatide, tirzepatide, aleniglipron, efsubaglutide alfa, utreglutide, bofanglutide, dapiglutide, teduglutide, glepaglutide, apraglutide, MET-097i, MET-224o, MET-002o, MET-815i, or dulaglutide. In some embodiments, the GLP-1 receptor agonist is semaglutide. In some embodiments, the GLP-1 receptor agonist is orforglipron. In some embodiments, the GLP-1 receptor agonist is exenatide. In some embodiments, the GLP-1 receptor agonist is exenatide LAR. In some embodiments, the GLP-1 receptor agonist is liraglutide. In some embodiments, the GLP-1 receptor agonist is taspoglutide. In some embodiments, the GLP-1 receptor agonist is semaglutide. In some embodiments, the GLP-1 receptor agonist is albiglutide. In some embodiments, the GLP-1 receptor agonist is lixisenatide. In some embodiments, the GLP-1 receptor agonist is tirzepatide. In some embodiments, the GLP-1 receptor agonist is aleniglipron. In some embodiments, the GLP-1 receptor agonist is efsubaglutide alfa. In some embodiments, the GLP-1 receptor agonist is utreglutide. In some embodiments, the GLP-1 receptor agonist is bofanglutide. In some embodiments, the GLP-1 receptor agonist is dapiglutide. In some embodiments, the GLP-2 receptor agonist is dapiglutide. In some embodiments, the GLP-2 receptor agonist is teduglutide. In some embodiments, the GLP-2 receptor agonist is glepaglutide. In some embodiments, the GLP-2 receptor agonist is apraglutide.

In some embodiments, the GLP-1 receptor agonist is MET-097i. In some embodiments, the GLP-1 receptor agonist is MET-224o. In some embodiments, the GLP-1 receptor agonist is MET-002o. In some embodiments, the GLP-1 receptor agonist is MET-815i. In some embodiments, the GLP-1 receptor agonist is dulaglutide. In another embodiment, the present method encompasses the use of any GLP-1 receptor agonists that are currently under development or those to be developed in the future; examples of GLP-1 receptor agonists include, but are not limited to, ecnoglutide (SciWind), survodutide (BI/Zealand), mazdutide (Innovent), pemvidutide (Altimmune), cotadutide (AZ), retatrutide (Eli Lilly), orforglipron (Eli Lilly), maritide (Amgen), VK2735 (Viking), CT-388 (Carmot), CT-996, GL0034 (Sun Pharma), GMA 106 (GMAX Bio.), danuglipron (Pfizer), GSBR-1290 (Structure Therapeutics), ARD-101 (Aardvark Therapeutics), ECC5004 (AstraZeneca/Eccogene), MET-097i (MetSera), ASC30 (Ascletis), HRS9531 (Hengrui), HDM1005 (Huandong Medicine), DA-1726 (MetaVia Pharma), MET-097o (MetSera), MET-224o (MetSera), NN-9662 (NovoNordisk), PF-07976016 (Pfizer), TERN-601 (Terns Pharmaceuticals), CT-868 (Roche), HS-10501 (Hansoh), KAI-9531 (Kailera), HS-10535 (Merck), HRS-7535, RGT-075, MD001, HDM1002, BGM0504, NA-931, HM15275, MWN109, MET-002o, MET-815i, and amycretin.

In another embodiment, the present invention provides a method of preventing, reducing, or treating adverse effects caused by an incretin agonist or antagonist containing drug in a subject who has been previously treated with the incretin agonist or antagonist containing drug, comprising administering to the subject a therapeutically effective amount of a SARM disclosed herein. In some embodiments, continued SARM therapy after discontinuation of coadministration of the incretin agonist or antagonist containing drug with the SARM allows for prevention, reduction, or treatment of rebound effects in the subject, wherein the subject does not experience reversal of benefit effects of administration of the incretin agonist or antagonist containing drug. In some embodiments, continued SARM monotherapy after discontinuation of the incretin agonist or antagonist containing drug monotherapy allows for prevention, reduction, or treatment of rebound effects in the subject, wherein the subject does not experience reversal of benefit effects of administration of the incretin agonist or antagonist containing drug.

In some embodiments, the rebound weight gain effects due to the discontinuation of the incretin agonist or antagonist containing drug may include total body weight gain, FBM gain, LBM loss, worsening of body composition values, decreased physical function, and/or increased waist circumference, or any combination of these rebound effects. In some embodiments, administration of SARMs of this invention allows for no or reduced rebound in total body weight following discontinuation of the incretin agonist or antagonist containing drug. In some embodiments, methods of this invention allow for no or reduced rebound in FBM following discontinuation of the incretin agonist or antagonist containing drug. In some embodiments, methods of this invention allow for no or reduced rebound in body composition values following discontinuation of the incretin agonist or antagonist containing drug. In some embodiments, methods of this invention allow for no or reduced rebound in physical function following discontinuation of the incretin agonist or antagonist containing drug. In some embodiments, methods of this invention allow for no or reduced rebound in waist circumference following discontinuation of the incretin agonist or antagonist containing drug. In some embodiments, the method comprises use of any one of the SARM compounds represented by the structure of Formula I, II, VIII, IX, X, XI, XII, XIII, and XIV. In some embodiments, the SARM compound is Formula IX. In some embodiments, the subject has prediabetes, diabetes or does not have diabetes. In some embodiments, the subject is an obese or overweight patient. In some embodiments, the subject is a sarcopenic obese or overweight patient. In other embodiments, the subject is a sarcopenic obese or overweight older patient, for example, that is 60 or older than 60 years of age. In some embodiments, the subject has sarcopenic obesity. In some embodiments, the subject is 60 years old or older. In some embodiments, the incretin agonist or antagonist containing drug is a GLP-1 receptor agonist. In some embodiments, the incretin agonist or antagonist containing drug is a GLP-2 receptor agonist. In some embodiments, the GLP-1 receptor agonist is orforglipron, exenatide, exenatide LAR, liraglutide, taspoglutide, semaglutide, albiglutide, lixisenatide, tirzepatide, aleniglipron, efsubaglutide alfa, utreglutide, bofanglutide, dapiglutide, teduglutide, glepaglutide, apraglutide, MET-097i, MET-224o, MET-002o, MET-815i, or dulaglutide. In some embodiments, the GLP-1 receptor agonist is semaglutide. In some embodiments, the GLP-1 receptor agonist is orforglipron. In some embodiments, the GLP-1 receptor agonist is exenatide. In some embodiments, the GLP-1 receptor agonist is exenatide LAR. In some embodiments, the GLP-1 receptor agonist is liraglutide. In some embodiments, the GLP-1 receptor agonist is taspoglutide. In some embodiments, the GLP-1 receptor agonist is semaglutide. In some embodiments, the GLP-1 receptor agonist is albiglutide. In some embodiments, the GLP-1 receptor agonist is lixisenatide. In some embodiments, the GLP-1 receptor agonist is tirzepatide. In some embodiments, the GLP-1 receptor agonist is aleniglipron. In some embodiments, the GLP-1 receptor agonist is efsubaglutide alfa. In some embodiments, the GLP-1 receptor agonist is utreglutide. In some embodiments, the GLP-1 receptor agonist is bofanglutide. In some embodiments, the GLP-1 receptor agonist is dapiglutide. In some embodiments, the GLP-1 receptor agonist is MET-097i. In some embodiments, the GLP-1 receptor agonist is MET-224o. In some embodiments, the GLP-1 receptor agonist is MET-002o. In some embodiments, the GLP-1 receptor agonist is MET-815i. In some embodiments, the GLP-1 receptor agonist is dulaglutide. In some embodiments, the GLP-2 receptor agonist is dapiglutide. In some embodiments, the GLP-2 receptor agonist is teduglutide. In some embodiments, the GLP-2 receptor agonist is glepaglutide. In some embodiments, the GLP-2 receptor agonist is apraglutide.

In another embodiment, the present method encompasses the use of any GLP-1 receptor agonists that are currently under development or those to be developed in the future; examples of GLP-1 receptor agonists include, but are not limited to, ecnoglutide (SciWind), survodutide (BI/Zealand), mazdutide (Innovent), pemvidutide (Altimmune), cotadutide (AZ), retatrutide (Eli Lilly), orforglipron (Eli Lilly), maritide (Amgen), VK2735 (Viking), CT-388 (Carmot), CT-996, GL0034 (Sun Pharma), GMA 106 (GMAX Bio.), danuglipron (Pfizer), GSBR-1290 (Structure Therapeutics), ARD-101 (Aardvark Therapeutics), ECC5004 (AstraZeneca/Eccogene), MET-097i (MetSera), ASC30 (Ascletis), HRS9531 (Hengrui), HDM1005 (Huandong Medicine), DA-1726 (MetaVia Pharma), MET-097o (MetSera), MET-224o (MetSera), NN-9662 (NovoNordisk), PF-07976016 (Pfizer), TERN-601 (Terns Pharmaceuticals), CT-868 (Roche), HS-10501 (Hansoh), KAI-9531 (Kailera), HS-10535 (Merck), HRS-7535, RGT-075, MD001, HDM1002, BGM0504, NA-931, HM15275, MWN109, MET-002o, MET-815i, and amycretin.

In one embodiment, the present invention provides a method for decreasing fat mass while preserving or increasing lean mass in a subject who is under treatment or stops treatment with an incretin agonist or antagonist containing drug, comprising administering to the subject a therapeutically effective amount of a selective androgen receptor modulator (SARM) compound represented by a structure of Formula IX. In some embodiments, the subject has prediabetes, diabetes or does not have diabetes. In some embodiments, the subject is obese or overweight. In some embodiments, the subject is a sarcopenic obese or overweight patient. In some embodiments, the subject has sarcopenic obesity. In some embodiments, the subject is 60 years old or older. In other embodiments, the subject has sarcopenic obesity who is 60 years old or older. In some embodiments, the incretin agonist or antagonist containing drug is a GLP-1 receptor agonist. In some embodiments, the incretin agonist or antagonist containing drug is a GLP-2 receptor agonist. In some embodiments, the GLP-1 receptor agonist is orforglipron, exenatide, exenatide LAR, liraglutide, taspoglutide, semaglutide, albiglutide, lixisenatide, tirzepatide, aleniglipron, efsubaglutide alfa, utreglutide, bofanglutide, dapiglutide, teduglutide, glepaglutide, apraglutide, MET-097i, MET-224o, MET-002o, MET-815i, or dulaglutide. In certain embodiments, the GLP-1 receptor agonist is semaglutide. In some embodiments, the GLP-1 receptor agonist is orforglipron. In some embodiments, the GLP-1 receptor agonist is tirzepatide. In some embodiments, the SARM compound of Formula IX is administered at a dose of from 0.1 mg to 50 mg per day. In some embodiments, the SARM compound of Formula IX is administered at a dose of 0.1 mg per day, 0.3 mg per day, 1 mg per day, 3 mg per day, 6 mg per day, 9 mg per day, or 18 mg per day. In some embodiments, the SARM compound of Formula IX is administered to the subject concurrently with, or prior to, or after the treatment with the incretin agonist or antagonist containing drug.

In one embodiment, the present invention provides a method of reducing fat while preserving and/or building muscle in a subject, comprising administering to the subject a therapeutically effective amount of a selective androgen receptor modulator (SARM) and a myostatin inhibitor. Examples of myostatin inhibitors are generally known in the art, for example, anti-myostatin antibodies, activin receptor type 2 antagonist, anti-latent myostatin antibody, and selective activin receptor ligand trap. In one embodiment, the method comprises use of any one of the SARM compounds represented by the structure of Formula I. In another embodiment, the method comprises use of any one of the SARM compounds represented by the structure of Formula II. In another embodiment, the method comprises use of the SARM compound represented by the structure of Formula VIII. In another embodiment, the method comprises use of the SARM compound represented by the structure of Formula IX. In another embodiment, the method comprises use of the SARM compound represented by the structure of Formula X. In another embodiment, the method comprises use of the SARM compound represented by the structure of Formula XI. In another embodiment, the method comprises use of the SARM compound represented by the structure of Formula XII. In another embodiment, the method comprises use of the SARM compound represented by the structure of Formula XIII. In another embodiment, the method comprises use of the SARM compound represented by the structure of Formula XIV.

In one embodiment, the present invention provides a method of reducing fat while preserving and/or building muscle in a subject, comprising administering to the subject a therapeutically effective amount of a selective androgen receptor modulator (SARM) and an anti-myostatin. Examples of anti-myostatins include, but are not limited to, bimagrumab, apitegromab, garetosmab, taldefgrobep, KER-065, RO7204239, and trevogrumab. In one embodiment, the method comprises use of any one of the SARM compounds represented by the structure of Formula I. In another embodiment, the method comprises use of any one of the SARM compounds represented by the structure of Formula II. In another embodiment, the method comprises use of the SARM compound represented by the structure of Formula VIII. In another embodiment, the method comprises use of the SARM compound represented by the structure of Formula IX. In another embodiment, the method comprises use of the SARM compound represented by the structure of Formula X. In another embodiment, the method comprises use of the SARM compound represented by the structure of Formula XI. In another embodiment, the method comprises use of the SARM compound represented by the structure of Formula XII. In another embodiment, the method comprises use of the SARM compound represented by the structure of Formula XIII. In another embodiment, the method comprises use of the SARM compound represented by the structure of Formula XIV.

In one embodiment, the present invention provides a method of reducing fat while preserving and/or building muscle in a subject, comprising administering to the subject a therapeutically effective amount of a selective androgen receptor modulator (SARM) and an apelin receptor agonist. Examples of apelin receptor agonists are generally known in the art, for example, Azelaprag (BGE-105). In one embodiment, the method comprises use of any one of the SARM compounds represented by the structure of Formula I. In another embodiment, the method comprises use of any one of the SARM compounds represented by the structure of Formula II. In another embodiment, the method comprises use of the SARM compound represented by the structure of Formula VIII. In another embodiment, the method comprises use of the SARM compound represented by the structure of Formula IX. In another embodiment, the method comprises use of the SARM compound represented by the structure of Formula X. In another embodiment, the method comprises use of the SARM compound represented by the structure of Formula XI. In another embodiment, the method comprises use of the SARM compound represented by the structure of Formula XII. In another embodiment, the method comprises use of the SARM compound represented by the structure of Formula XIII. In another embodiment, the method comprises use of the SARM compound represented by the structure of Formula XIV.

In one embodiment, the present invention provides a method of reducing fat while preserving and/or building muscle in a subject and further preserving or improving physical function, comprising administering to the subject a therapeutically effective amount of a selective androgen receptor modulator (SARM) and an apelin receptor agonist. Examples of apelin receptor agonists are generally known in the art, for example, Azelaprag (BGE-105). In one embodiment, the method comprises use of any one of the SARM compounds represented by the structure of Formula I. In another embodiment, the method comprises use of any one of the SARM compounds represented by the structure of Formula II. In another embodiment, the method comprises use of the SARM compound represented by the structure of Formula VIII. In another embodiment, the method comprises use of the SARM compound represented by the structure of Formula IX. In another embodiment, the method comprises use of the SARM compound represented by the structure of Formula X. In another embodiment, the method comprises use of the SARM compound represented by the structure of Formula XI. In another embodiment, the method comprises use of the SARM compound represented by the structure of Formula XII. In another embodiment, the method comprises use of the SARM compound represented by the structure of Formula XIII. In another embodiment, the method comprises use of the SARM compound represented by the structure of Formula XIV.

In one embodiment of the method of the invention as described herein, the SARM compound is represented by a structure of Formula I.

I

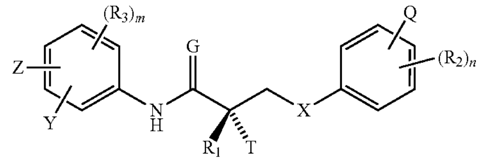

wherein

X is a bond, O, $CH_2$, NH, S, Se, PR, NO, or NR;

G is O or S;

T is OH, OR, —$NHCOCH_3$, or NHCOR;

R is alkyl, haloalkyl, dihaloalkyl, trihaloalkyl, $CH_2F$, $CHF_2$, $CF_3$, $CF_2CF_3$, aryl, phenyl, halogen, alkenyl, or OH;

$R_1$ is $CH_3$, $CH_2F$, $CHF_2$, $CF_3$, $CH_2CH_3$, or $CF_2CF_3$;

$R_2$ is H, F, Cl, Br, I, $CH_3$, $CF_3$, OH, CN, $NO_2$, $NHCOCH_3$, $NHCOCF_3$, NHCOR, alkyl, arylalkyl, OR, $NH_2$, NHR, $N(R)_2$, or SR;

$R_3$ is H, F, Cl, Br, I, CN, $NO_2$, COR, COOH, CONHR, $CF_3$, or $Sn(R)_3$, or $R_3$ together with the benzene ring to which it is attached forms a fused ring system represented by the structure:

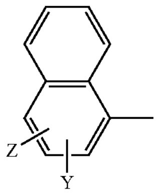

or

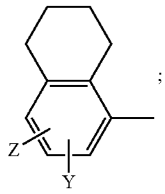

;

Z is $NO_2$, CN, COR, COOH, or CONHR;

Y is $CF_3$, F, Br, Cl, I, CN, or $Sn(R)_3$;

Q is CN, alkyl, halogen, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, or SR;

or Q together with the benzene ring to which it is attached is a fused ring system represented by structure A, B, or C:

A

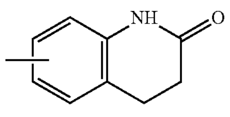

B

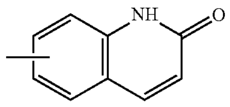

C

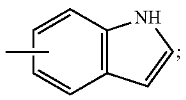

;

n is an integer of 1-4; and m is an integer of 1-3, or an optical isomer, a racemic mixture, a pharmaceutically acceptable salt, a pharmaceutical product, a hydrate, an N-oxide, or a crystal thereof.

In another embodiment, the SARM compound used in the above method is represented by a structure of Formula II:

II

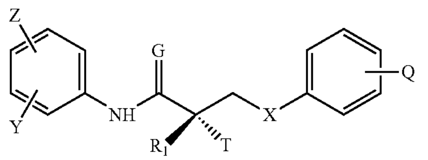

wherein

X is a bond, O, $CH_2$, NH, Se, PR, or NR;

G is O or S;

T is OH, OR, —$NHCOCH_3$, or NHCOR;

Z is $NO_2$, CN, COR, COOH, or CONHR;

Y is I, $CF_3$, Br, Cl, or $Sn(R)_3$;

Q is CN, alkyl, halogen, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, or SR;

or Q together with the benzene ring to which it is attached is a fused ring system represented by structure A, B, or C:

A

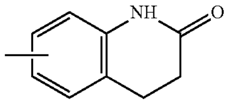

B

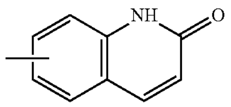

C

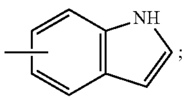

;

R is a $C_1$-$C_4$ alkyl, aryl, phenyl, alkenyl, hydroxyl, a $C_1$-$C_4$ haloalkyl, halogen, or haloalkenyl; and $R_1$ is $CH_3$, $CF_3$, $CH_2CH_3$, or $CF_2CF_3$.

In another embodiment, the SARM compound is represented by a structure of Formulas VIII, IX, X, XI, XII, XIII, and XIV:

VIII

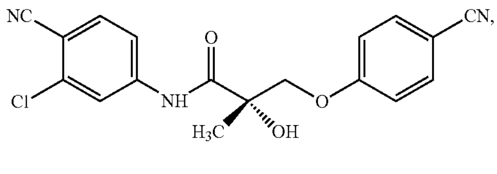

,

-continued

IX

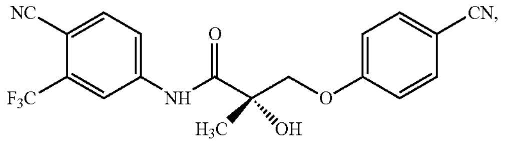

X

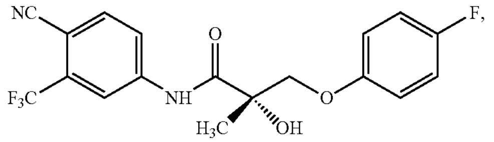

XI

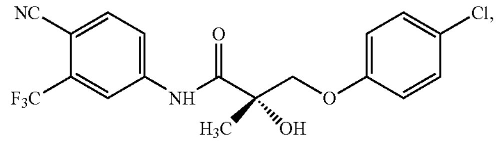

XII

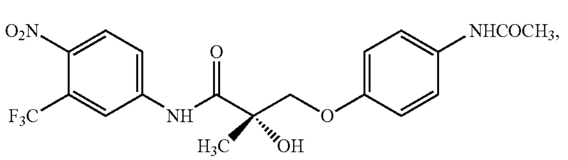

XIII

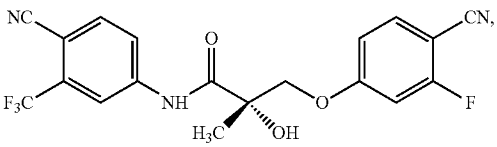

or

XIV

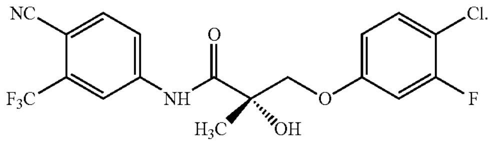

The methods disclosed herein encompass uses of any one of the SARM compounds disclosed herein in a subject who is under treatment or stops treatment with any one of the incretin agonist or antagonist containing drugs disclosed herein, or with any incretin agonist or antagonist containing drugs to be developed in the future. For example, the methods disclosed herein comprise use of any one of the SARM compounds represented by the structure of Formulas I, II, VIII, IX, X, XI, XII, XIII, and XIV in a subject who is under treatment or stops treatment with any one of the incretin agonist or antagonist containing drugs disclosed herein. In one embodiment, the methods disclosed herein comprise use of any one of the SARM compounds represented by the structure of Formula I in a subject who is under treatment or stops treatment with any one of the incretin agonist or antagonist containing drugs disclosed herein. In another embodiment, the methods disclosed herein comprise use of any one of the SARM compounds represented by the structure of Formula II in a subject who is under treatment or stops treatment with any one of the incretin agonist or antagonist containing drugs disclosed herein. In another embodiment, the methods disclosed herein comprise use of the SARM compound represented by the structure of Formula VIII in a subject who is under treatment or stops treatment with any one of the incretin agonist or antagonist containing drugs disclosed herein. In another embodiment, the methods disclosed herein comprise use of the SARM compound represented by the structure of Formula IX in a subject who is under treatment or stops treatment with any one of the incretin agonist or antagonist containing drugs disclosed herein. In another embodiment, the methods disclosed herein comprise use of the SARM compound represented by the structure of Formula X in a subject who is under treatment or stops treatment with any one of the incretin agonist or antagonist containing drugs disclosed herein. In another embodiment, the methods disclosed herein comprise use of the SARM compound represented by the structure of Formula XI in a subject who is under treatment or stops treatment with any one of the incretin agonist or antagonist containing drugs disclosed herein. In another embodiment, the methods disclosed herein comprise use of the SARM compound represented by the structure of Formula XII in a subject who is under treatment or stops treatment with any one of the incretin agonist or antagonist containing drugs disclosed herein. In another embodiment, the methods disclosed herein comprise use of the SARM compound represented by the structure of Formula XIII in a subject who is under treatment or stops treatment with any one of the incretin agonist or antagonist containing drugs disclosed herein. In another embodiment, the methods disclosed herein comprise use of the SARM compound represented by the structure of Formula XIV in a subject who is under treatment or stops treatment with any one of the incretin agonist or antagonist containing drugs disclosed herein. In some embodiments, the incretin agonist or antagonist containing drug is a GLP-1 receptor agonist. In some embodiments, the GLP-1 receptor agonist is orforglipron. In some embodiments, the GLP-1 receptor agonist is exenatide. In some embodiments, the GLP-1 receptor agonist is exenatide LAR. In some embodiments, the GLP-1 receptor agonist is liraglutide. In some embodiments, the GLP-1 receptor agonist is taspoglutide. In some embodiments, the GLP-1 receptor agonist is semaglutide. In some embodiments, the GLP-1 receptor agonist is albiglutide. In some embodiments, the GLP-1 receptor agonist is lixisenatide. In some embodiments, the GLP-1 receptor agonist is tirzepatide. In some embodiments, the GLP-1 receptor agonist is ecnoglutide. In some embodiments, the GLP-1 receptor agonist is survodutide. In some embodiments, the GLP-1 receptor agonist is mazdutide. In some embodiments, the GLP-1 receptor agonist is pemvidutide. In some embodiments, the GLP-1 receptor agonist is cotadutide. In some embodiments, the GLP-1 receptor agonist is retatrutide. In some embodiments, the GLP-1 receptor agonist is orforglipron. In some embodiments, the GLP-1 receptor agonist is maritide. In some embodiments, the GLP-1 receptor agonist is aleniglipron. In some embodiments, the GLP-1 receptor agonist is efsubaglutide alfa. In some embodiments, the GLP-1 receptor agonist is utreglutide. In some embodiments, the GLP-1 receptor agonist is bofanglutide. In some embodiments, the GLP-1 receptor agonist is dapiglutide. In some embodiments, the GLP-2 receptor agonist is dapiglutide. In some embodiments, the GLP-2 receptor agonist is teduglutide. In some embodiments, the GLP-2 receptor agonist is glepaglutide. In some embodiments, the GLP-2 receptor agonist is apraglutide.

In some embodiments, the GLP-1 receptor agonist is MET-097i. In some embodiments, the GLP-1 receptor agonist is MET-224o. In some embodiments, the GLP-1 receptor agonist is MET-002o. In some embodiments, the GLP-1 receptor agonist is MET-815i. In some embodiments, the GLP-1 receptor agonist is VK2735. In some embodiments, the GLP-1 receptor agonist is CT-388. In some embodiments, the GLP-1 receptor agonist is GL0034. In some embodiments, the GLP-1 receptor agonist is GMA 106. In some embodiments, the GLP-1 receptor agonist is danuglipron. In some embodiments, the GLP-1 receptor agonist is GSBR-1290. In some embodiments, the GLP-1 receptor agonist is ARD-101. In some embodiments, the GLP-1 receptor agonist is ECC5004. In some embodiments, the GLP-1 receptor agonist is MET-097i (MetSera). In some embodiments, the GLP-1 receptor agonist is ASC30 (Ascletis). In some embodiments, the GLP-1 receptor agonist is HRS9531 (Hengrui). In some embodiments, the GLP-1 receptor agonist is HDM1005 (Huandong Medicine). In some embodiments, the GLP-1 receptor agonist is DA-1726 (MetaVia Pharma). In some embodiments, the GLP-1 receptor agonist is MET-097o (MetSera). In some embodiments, the GLP-1 receptor agonist is MET-224o (MetSera). In some embodiments, the GLP-1 receptor agonist is NN-9662 (NovoNordisk). In some embodiments, the GLP-1 receptor agonist is PF-07976016 (Pfizer). In some embodiments, the GLP-1 receptor agonist is TERN-601 (Terns Pharmaceuticals). In some embodiments, the GLP-1 receptor agonist is CT-868 (Roche). In some embodiments, the GLP-1 receptor agonist is HS-10501 (Hansoh). In some embodiments, the GLP-1 receptor agonist is KAI-9531 (Kailera). In some embodiments, the GLP-1 receptor agonist is HS-10535 (Merck). In some embodiments, the GLP-1 receptor agonist is HRS-7535. In some embodiments, the GLP-1 receptor agonist is RGT-075. In some embodiments, the GLP-1 receptor agonist is MD001. In some embodiments, the GLP-1 receptor agonist is HDM1002. In some embodiments, the GLP-1 receptor agonist is BGM0504. In some embodiments, the GLP-1 receptor agonist is NA-931. In some embodiments, the GLP-1 receptor agonist is HM15275. In some embodiments, the GLP-1 receptor agonist is MWN109. In some embodiments, the GLP-1 receptor agonist is MET-002o. In some embodiments, the GLP-1 receptor agonist is MET-815i. In some embodiments, the GLP-1 receptor agonist is amycretin.

In another embodiment, the methods disclosed herein comprise use of the SARM compound represented by the structure of Formula IX in a subject who is under treatment or stops treatment with the GLP-1 receptor agonist exenatide. In another embodiment, the methods disclosed herein comprise use of the SARM compound represented by the structure of Formula IX in a subject who is under treatment or stops treatment with the GLP-1 receptor agonist exenatide LAR. In another embodiment, the methods disclosed herein comprise use of the SARM compound represented by the structure of Formula IX in a subject who is under treatment or stops treatment with the GLP-1 receptor agonist liraglutide. In another embodiment, the methods disclosed herein comprise use of the SARM compound represented by the structure of Formula IX in a subject who is under treatment or stops treatment with the GLP-1 receptor agonist taspoglutide. In another embodiment, the methods disclosed herein comprise use of the SARM compound represented by the structure of Formula IX in a subject who is under treatment or stops treatment with the GLP-1 receptor agonist semaglutide. In another embodiment, the methods disclosed herein comprise use of the SARM compound represented by the structure of Formula IX in a subject who is under treatment or stops treatment with the GLP-1 receptor agonist albiglutide. In another embodiment, the methods disclosed herein comprise use of the SARM compound represented by the structure of Formula IX in a subject who is under treatment or stops treatment with the GLP-1 receptor agonist lixisenatide. In another embodiment, the methods disclosed herein comprise use of the SARM compound represented by the structure of Formula IX in a subject who is under treatment or stops treatment with the GLP-1 receptor agonist tirzepatide. In another embodiment, the methods disclosed herein comprise use of the SARM compound represented by the structure of Formula IX in a subject who is under treatment or stops treatment with the GLP-1 receptor agonist aleniglipron. In another embodiment, the methods disclosed herein comprise use of the SARM compound represented by the structure of Formula IX in a subject who is under treatment or stops treatment with the GLP-1 receptor agonist efsubaglutide alfa. In another embodiment, the methods disclosed herein comprise use of the SARM compound represented by the structure of Formula IX in a subject who is under treatment or stops treatment with the GLP-1 receptor agonist utreglutide. In another embodiment, the methods disclosed herein comprise use of the SARM compound represented by the structure of Formula IX in a subject who is under treatment or stops treatment with the GLP-1 receptor agonist bofanglutide. In another embodiment, the methods disclosed herein comprise use of the SARM compound represented by the structure of Formula IX in a subject who is under treatment or stops treatment with the GLP-1 receptor agonist dapiglutide. In another embodiment, the methods disclosed herein comprise use of the SARM compound represented by the structure of Formula IX in a subject who is under treatment or stops treatment with the GLP-2 receptor agonist dapiglutide. In another embodiment, the methods disclosed herein comprise use of the SARM compound represented by the structure of Formula IX in a subject who is under treatment or stops treatment with the GLP-2 receptor agonist teduglutide. In another embodiment, the methods disclosed herein comprise use of the SARM compound represented by the structure of Formula IX in a subject who is under treatment or stops treatment with the GLP-2 receptor agonist glepaglutide. In another embodiment, the methods disclosed herein comprise use of the SARM compound represented by the structure of Formula IX in a subject who is under treatment or stops treatment with the GLP-2 receptor agonist apraglutide. In another embodiment, the methods disclosed herein comprise use of the SARM compound represented by the structure of Formula IX in a subject who is under treatment or stops treatment with the GLP-1 receptor agonist MET-097i. In another embodiment, the methods disclosed herein comprise use of the SARM compound represented by the structure of Formula IX in a subject who is under treatment or stops treatment with the GLP-1 receptor agonist MET-224o. In another embodiment, the methods disclosed herein comprise use of the SARM compound represented by the structure of Formula IX in a subject who is under treatment or stops treatment with the GLP-1 receptor agonist MET-002o. In another embodiment, the methods disclosed herein comprise use of the SARM compound represented by the structure of Formula IX in a subject who is under treatment or stops treatment with the GLP-1 receptor agonist MET-815i. In another embodiment, the methods disclosed herein comprise use of the SARM compound represented by the structure of Formula IX in a subject who is under treatment or stops treatment with the GLP-1 receptor agonist dulaglutide. In another embodiment, the methods disclosed herein comprise use of the SARM compound represented by the structure of Formula IX in a subject who is under treatment or stops treatment with the GLP-1 receptor agonist ecnoglutide. In another embodiment, the methods disclosed herein comprise use of the SARM compound represented by the structure of Formula IX in a subject who is under treatment or stops treatment with the GLP-1 receptor agonist survodutide. In another embodiment, the methods disclosed herein comprise use of the SARM compound represented by the structure of Formula IX in a subject who is under treatment or stops treatment with the GLP-1 receptor agonist mazdutide. In another embodiment, the methods disclosed herein comprise use of the SARM compound represented by the structure of Formula IX in a subject who is under treatment or stops treatment with the GLP-1 receptor agonist pemvidutide. In another embodiment, the methods disclosed herein comprise use of the SARM compound represented by the structure of Formula IX in a subject who is under treatment or stops treatment with the GLP-1 receptor agonist cotadutide. In another embodiment, the methods disclosed herein comprise use of the SARM compound represented by the structure of Formula IX in a subject who is under treatment or stops treatment with the GLP-1 receptor agonist retatrutide. In another embodiment, the methods disclosed herein comprise use of the SARM compound represented by the structure of Formula IX in a subject who is under treatment or stops treatment with the GLP-1 receptor agonist orforglipron. In another embodiment, the methods disclosed herein comprise use of the SARM compound represented by the structure of Formula IX in a subject who is under treatment or stops treatment with the GLP-1 receptor agonist maritide. In another embodiment, the methods disclosed herein comprise use of the SARM compound represented by the structure of Formula IX in a subject who is under treatment or stops treatment with the GLP-1 receptor agonist VK2735. In another embodiment, the methods disclosed herein comprise use of the SARM compound represented by the structure of Formula IX in a subject who is under treatment or stops treatment with the GLP-1 receptor agonist CT-388. In another embodiment, the methods disclosed herein comprise use of the SARM compound represented by the structure of Formula IX in a subject who is under treatment or stops treatment with the GLP-1 receptor agonist GL0034. In another embodiment, the methods disclosed herein comprise use of the SARM compound represented by the structure of Formula IX in a subject who is under treatment or stops treatment with the GLP-1 receptor agonist GMA 106. In another embodiment, the methods disclosed herein comprise use of the SARM compound represented by the structure of Formula IX in a subject who is under treatment or stops treatment with the GLP-1 receptor agonist danuglipron. In another embodiment, the methods disclosed herein comprise use of the SARM compound represented by the structure of Formula IX in a subject who is under treatment or stops treatment with the GLP-1 receptor agonist GSBR-1290. In another embodiment, the methods disclosed herein comprise use of the SARM compound represented by the structure of Formula IX in a subject who is under treatment or stops treatment with the GLP-1 receptor agonist ARD-101. In another embodiment, the methods disclosed herein comprise use of the SARM compound represented by the structure of Formula IX in a subject who is under treatment or stops treatment with the GLP-1 receptor agonist ECC5004. In another embodiment, the methods disclosed herein comprise use of the SARM compound represented by the structure of Formula IX in a subject who is under treatment or stops treatment with the GLP-1 receptor agonist MET-097i (MetSera). In another embodiment, the methods disclosed herein comprise use of the SARM compound represented by the structure of Formula IX in a subject who is under treatment or stops treatment with the GLP-1 receptor agonist ASC30 (Ascletis). In another embodiment, the methods disclosed herein comprise use of the SARM compound represented by the structure of Formula IX in a subject who is under treatment or stops treatment with the GLP-1 receptor agonist HRS9531 (Hengrui). In another embodiment, the methods disclosed herein comprise use of the SARM compound represented by the structure of Formula IX in a subject who is under treatment or stops treatment with the GLP-1 receptor agonist HDM1005 (Huandong Medicine). In another embodiment, the methods disclosed herein comprise use of the SARM compound represented by the structure of Formula IX in a subject who is under treatment or stops treatment with the GLP-1 receptor agonist DA-1726 (MetaVia Pharma). In another embodiment, the methods disclosed herein comprise use of the SARM compound represented by the structure of Formula IX in a subject who is under treatment or stops treatment with the GLP-1 receptor agonist MET-097o (MetSera). In another embodiment, the methods disclosed herein comprise use of the SARM compound represented by the structure of Formula IX in a subject who is under treatment or stops treatment with the GLP-1 receptor agonist MET-224o (MetSera). In another embodiment, the methods disclosed herein comprise use of the SARM compound represented by the structure of Formula IX in a subject who is under treatment or stops treatment with the GLP-1 receptor agonist NN-9662 (NovoNordisk). In another embodiment, the methods disclosed herein comprise use of the SARM compound represented by the structure of Formula IX in a subject who is under treatment or stops treatment with the GLP-1 receptor agonist PF-07976016 (Pfizer). In another embodiment, the methods disclosed herein comprise use of the SARM compound represented by the structure of Formula IX in a subject who is under treatment or stops treatment with the GLP-1 receptor agonist TERN-601 (Terns Pharmaceuticals). In another embodiment, the methods disclosed herein comprise use of the SARM compound represented by the structure of Formula IX in a subject who is under treatment or stops treatment with the GLP-1 receptor agonist CT-868 (Roche). In another embodiment, the methods disclosed herein comprise use of the SARM compound represented by the structure of Formula IX in a subject who is under treatment or stops treatment with the GLP-1 receptor agonist HS-10501 (Hansoh). In another embodiment, the methods disclosed herein comprise use of the SARM compound represented by the structure of Formula IX in a subject who is under treatment or stops treatment with the GLP-1 receptor agonist KAI-9531 (Kailera). In another embodiment, the methods disclosed herein comprise use of the SARM compound represented by the structure of Formula IX in a subject who is under treatment or stops treatment with the GLP-1 receptor agonist HS-10535 (Merck). In another embodiment, the methods disclosed herein comprise use of the SARM compound represented by the structure of Formula IX in a subject who is under treatment or stops treatment with the GLP-1 receptor agonist HRS-7535. In another embodiment, the methods disclosed herein comprise use of the SARM compound represented by the structure of Formula IX in a subject who is under treatment or stops treatment with the GLP-1 receptor agonist RGT-075. In another embodiment, the methods disclosed herein comprise use of the SARM compound represented by the structure of Formula IX in a subject who is under treatment or stops treatment with the GLP-1 receptor agonist MD001. In another embodiment, the methods disclosed herein comprise use of the SARM compound represented by the structure of Formula IX in a subject who is under treatment or stops treatment with the GLP-1 receptor agonist HDM1002. In another embodiment, the methods disclosed herein comprise use of the SARM compound represented by the structure of Formula IX in a subject who is under treatment or stops treatment with the GLP-1 receptor agonist BGM0504. In another embodiment, the methods disclosed herein comprise use of the SARM compound represented by the structure of Formula IX in a subject who is under treatment or stops treatment with the GLP-1 receptor agonist NA-931. In another embodiment, the methods disclosed herein comprise use of the SARM compound represented by the structure of Formula IX in a subject who is under treatment or stops treatment with the GLP-1 receptor agonist HM15275. In another embodiment, the methods disclosed herein comprise use of the SARM compound represented by the structure of Formula IX in a subject who is under treatment or stops treatment with the GLP-1 receptor agonist MWN109. In another embodiment, the methods disclosed herein comprise use of the SARM compound represented by the structure of Formula IX in a subject who is under treatment or stops treatment with the GLP-1 receptor agonist MET-002o. In another embodiment, the methods disclosed herein comprise use of the SARM compound represented by the structure of Formula IX in a subject who is under treatment or stops treatment with the GLP-1 receptor agonist MET-815i. In another embodiment, the methods disclosed herein comprise use of the SARM compound represented by the structure of Formula IX in a subject who is under treatment or stops treatment with the GLP-1 receptor agonist amycretin.

In another embodiment, the present invention provides a method of decreasing fat mass in a subject, comprising administering to the subject any one of the SARM compounds disclosed herein, together with any one of the incretin agonist or antagonist containing drugs disclosed herein, or with any incretin agonist or antagonist containing drugs to be developed in the future. In one embodiment, the method further comprises administering to the subject any other weight loss drugs used in the art. Accordingly, the method comprises use of any one of the SARM compounds represented by the structure of Formula I, II, VIII, IX, X, XI, XII, XIII, or XIV together with any one of the incretin agonist or antagonist containing drugs disclosed herein. The combined uses of various SARM compounds with the various incretin agonist or antagonist containing drugs disclosed herein have been described above. For example, the method comprises use of the SARM compound represented by the structure of Formula IX together with any one of the incretin agonist or antagonist containing drugs disclosed herein.

In another embodiment, the present invention provides a method of producing weight loss in a subject, comprising administering to the subject any one of the SARM compounds disclosed herein, together with any one of the incretin agonist or antagonist containing drugs disclosed herein, or with any incretin agonist or antagonist containing drugs to be developed in the future. In one embodiment, the method further comprises administering to the subject any other weight loss drugs used in the art. Accordingly, the method comprises use of any one of the SARM compounds represented by the structure of Formula I, II, VIII, IX, X, XI, XII, XIII, or XIV together with any one of the incretin agonist or antagonist containing drugs disclosed herein. The combined uses of various SARM compounds with the various incretin agonist or antagonist containing drugs disclosed herein have been described above. For example, the method comprises use of the SARM compound represented by the structure of Formula IX together with any one of the incretin agonist or antagonist containing drugs disclosed herein.

In another embodiment, the present invention provides a method of preserving muscle mass in a subject, comprising administering to the subject any one of the SARM compounds disclosed herein, together with any one of the incretin agonist or antagonist containing drugs disclosed herein, or with any incretin agonist or antagonist containing drugs to be developed in the future. In one embodiment, the method further comprises administering to the subject any other weight loss drugs used in the art. Accordingly, the method comprises use of any one of the SARM compounds represented by the structure of Formula I, II, VIII, IX, X, XI, XII, XIII, or XIV together with any one of the incretin agonist or antagonist containing drugs disclosed herein. The combined uses of various SARM compounds with the various incretin agonist or antagonist containing drugs disclosed herein have been described above. For example, the method comprises use of the SARM compound represented by the structure of Formula IX together with any one of the incretin agonist or antagonist containing drugs disclosed herein.

In another embodiment, the present invention provides a method of preventing, reducing, or treating adverse effects caused by an incretin agonist or antagonist containing drug in a subject who has been previously treated with the incretin agonist or antagonist containing drug, comprising administering to the subject a therapeutically effective amount of a SARM disclosed herein. Examples of the incretin agonist or antagonist containing drugs have been described above. Accordingly, the method comprises use of any one of the SARM compounds represented by the structure of Formula I, II, VIII, IX, X, XI, XII, XIII, or XIV. For example, the method comprises use of the SARM compound represented by the structure of Formula IX in a subject who has been previously treated with an incretin agonist or antagonist containing drug. In one embodiment, the method allows healthy weight loss in patients who have taken an incretin agonist or antagonist containing drug. In another embodiment, the method maintains or improves losses of fat body mass (FBM) in patients who have taken an incretin agonist or antagonist containing drug. In another embodiment, the method maintains or improves losses of visceral fat in patients who have taken an incretin agonist or antagonist containing drug. In another embodiment, the method prevents the loss of lean body mass (LBM) in patients who have taken an incretin agonist or antagonist containing drug. In another embodiment, the method prevents the loss of strength or physical function in patients who have taken an incretin agonist or antagonist containing drug. In another embodiment, the method reduces body mass index while increasing LBM in patients who have taken an incretin agonist or antagonist containing drug. In another embodiment, the method prevents or mitigates the tendency toward sarcopenic obesity in patients who have taken an incretin agonist or antagonist containing drug.

Methods of Uses in Combination with SGLT-2 Inhibitors

In some embodiments, the compositions and methods provided herein comprise use of selective androgen receptor modulator (SARM) to prevent side effects of treatment by sodium-glucose transport protein 2 (SGLT-2) inhibitors. In one embodiment, the methods and compositions disclosed herein exert beneficial effects on body composition in patients taking an SGLT-2 inhibitor. In another embodiment, the methods and compositions disclosed herein allow healthy weight loss in patients taking an SGLT-2 inhibitor. In some embodiments, the decrease in total body weight is ≥5%, or ≥10%, or ≥15% or ≥20%. In another embodiment, the methods and compositions disclosed herein maintain or improve losses of fat body mass (FBM) in patients taking an SGLT-2 inhibitor. In some embodiments, the decrease in FBM is ≥10%, or ≥15%, or ≥20%. In another embodiment, the methods and compositions disclosed herein maintain or improve losses of visceral fat in patients taking an SGLT-2 inhibitor. In another embodiment, the methods and compositions disclosed herein maintain or improve decreases in waist circumference in patients taking an SGLT-2 inhibitor. In another embodiment, the methods and compositions disclosed herein prevent the loss of lean body mass (LBM) or lead to gaining lean body mass (muscle mass) in patients taking an SGLT-2 inhibitor. In some embodiments, the increase in LBM is ≥0%, or ≥10%, or ≥15%, or ≥20%. In another embodiment, the methods and compositions disclosed herein prevent the loss of strength or physical function in patients taking an SGLT-2 inhibitor. In some embodiments, the increase in physical function is ≥10%, or ≥15%, or ≥20%. In another embodiment, the methods and compositions disclosed herein reduce body mass index while increasing LBM in patients taking an SGLT-2 inhibitor. In another embodiment, the methods and compositions disclosed herein prevent or mitigate the tendency toward sarcopenic obesity in patients taking an SGLT-2 inhibitor. In some embodiments, the compositions and methods provided herein further result in a gain of lean body mass (LBM) in the subject. In some embodiments, the compositions and methods provided herein further result in a decrease in waist circumference in the subject. In some embodiments, the compositions and methods provided herein prevent, reduce, or treat muscle weakness, poor balance, decreased gait speed, mobility disability, loss of independence, increased risk of falls, bone fractures, high hospitalization rates, and increased mortality, loss of physical function, physical disability, and/or poor quality of life in the subject. In some embodiments, the compositions and methods provided herein prevent, reduce or treat bone fractures in patients taking an SGLT-2 inhibitor. In some embodiments, the bone fractures are fractures of the hip or pelvis in the subject. In some embodiments, the compositions and methods provided herein prevent, reduce, or treat hip or pelvic in patients taking an SGLT-2 inhibitor.

In one embodiment, the present invention provides a method of reducing fat body mass while preserving and/or building lean body mass in a subject, comprising administering to the subject a therapeutically effective amount of a selective androgen receptor modulator (SARM) and an SGLT-2 inhibitor. In one embodiment, the present invention further provides for a method of increasing physical function in the subject with reduced fat and preserved and/or increased lean body mass, comprising administering to the subject a therapeutically effective amount of a selective androgen receptor modulator (SARM) and an SGLT-2 inhibitor. In some cases, the present invention further provides for a method of decreasing waist circumference in the subject with reduced fat and preserved and/or increased lean body mass, comprising administering to the subject a therapeutically effective amount of a selective androgen receptor modulator (SARM) and an SGLT-2 inhibitor. In some cases, there is a concomitant improvement in body composition, total body weight, waist circumference, and physical function.

In another embodiment, the present invention provides a method of preventing, reducing, or treating adverse effects caused by an SGLT-2 inhibitor in a subject who has been previously treated with the SGLT-2 inhibitor, comprising administering to the subject a therapeutically effective amount of a SARM disclosed herein. In some embodiments, continued SARM therapy after discontinuation of SGLT-2 inhibitor coadministration with SARM allows for prevention, reduction, or treatment of rebound effects in the subject, wherein the subject does not experience reversal of benefit effects of SGLT-2 inhibitor administration. In some embodiments, the rebound effects due to the discontinuation of the SGLT-2 inhibitor may include total body weight gain, FBM gain, LBM loss, worsening of body composition values, decreased physical function, and/or increased waist circumference, or any combination of these rebound effects. In some embodiments, administration of SARMs of this invention allow for no or reduced rebound in total body weight following discontinuation of the SGLT-2 inhibitor. In some embodiments, methods of this invention allow for no or reduced rebound in FBM following discontinuation of the SGLT-2 inhibitor. In some embodiments, methods of this invention allow for no or reduced rebound in body composition values following discontinuation of the SGLT-2 inhibitor. In some embodiments, methods of this invention allow for no or reduced rebound in physical function following discontinuation of the SGLT-2 inhibitor. In some embodiments, methods of this invention allow for no or reduced rebound in waist circumference following discontinuation of the SGLT-2 inhibitor.

In one embodiment, the present invention provides a method for preventing, reducing, or treating adverse effects caused by an SGLT-2 inhibitor in a subject who is under treatment or stops treatment with an SGLT-2 inhibitor, comprising administering to the subject a therapeutically effective amount of a selective androgen receptor modulator (SARM). Examples of SGLT-2 inhibitors include, but are not limited to, canagliflozin, dapagliflozin, empagliflozin, ertugliflozin or bexagliflozin. In some embodiments, the SGLT-2 inhibitor is canagliflozin. In some embodiments, the SGLT-2 inhibitor is dapagliflozin. In some embodiments, the SGLT-2 inhibitor is empagliflozin. In some embodiments, the SGLT-2 inhibitor is ertugliflozin. In some embodiments, the SGLT-2 inhibitor is bexagliflozin. In one embodiment, the SARM compound is represented by a structure of Formula I:

I

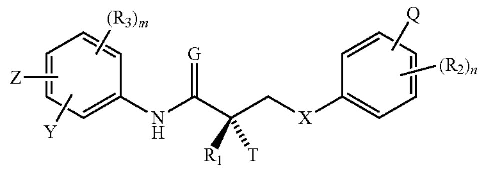

wherein

X is a bond, O, $CH_2$, NH, S, Se, PR, NO, or NR;

G is O or S;

T is OH, OR, —$NHCOCH_3$, or NHCOR;

R is alkyl, haloalkyl, dihaloalkyl, trihaloalkyl, $CH_2F$, $CHF_2$, $CF_3$, $CF_2CF_3$, aryl, phenyl, halogen, alkenyl, or OH;

$R_1$ is $CH_3$, $CH_2F$, $CHF_2$, $CF_3$, $CH_2CH_3$, or $CF_2CF_3$;

$R_2$ is H, F, Cl, Br, I, $CH_3$, $CF_3$, OH, CN, $NO_2$, $NHCOCH_3$, $NHCOCF_3$, NHCOR, alkyl, arylalkyl, OR, $NH_2$, NHR, $N(R)_2$, or SR;

$R_3$ is H, F, Cl, Br, I, CN, $NO_2$, COR, COOH, CONHR, $CF_3$, or $Sn(R)_3$, or $R_3$ together with the benzene ring to which it is attached forms a fused ring system represented by the structure:

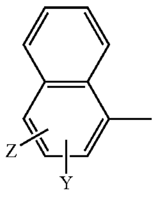 or 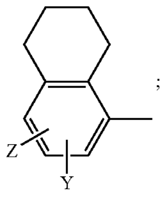 ;

Z is $NO_2$, CN, COR, COOH, or CONHR;

Y is $CF_3$, F, Br, Cl, I, CN, or $Sn(R)_3$;

Q is CN, alkyl, halogen, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, or SR;

or Q together with the benzene ring to which it is attached is a fused ring system represented by structure A, B, or C:

A

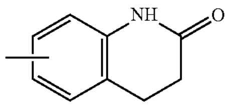

B

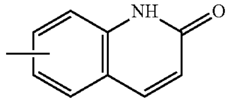

C

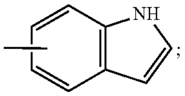

n is an integer of 1-4; and m is an integer of 1-3, or an optical isomer, a racemic mixture, a pharmaceutically acceptable salt, a pharmaceutical product, a hydrate, an N-oxide, or a crystal thereof.

In another embodiment, the SARM compound used in the above method is represented by a structure of Formula II:

II

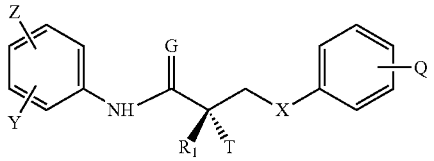

wherein

X is a bond, O, $CH_2$, NH, Se, PR, or NR;

G is O or S;

T is OH, OR, —$NHCOCH_3$, or NHCOR;

Z is $NO_2$, CN, COR, COOH, or CONHR;

Y is I, $CF_3$, Br, Cl, or $Sn(R)_3$;

Q is CN, alkyl, halogen, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, or SR;

or Q together with the benzene ring to which it is attached is a fused ring system represented by structure A, B, or C:

A

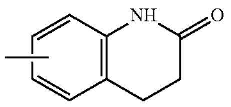

B

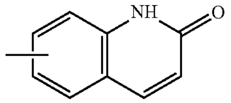

C

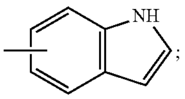

R is a $C_1$-$C_4$ alkyl, aryl, phenyl, alkenyl, hydroxyl, a $C_1$-$C_4$ haloalkyl, halogen, or haloalkenyl; and $R_1$ is $CH_3$, $CF_3$, $CH_2CH_3$, or $CF_2CF_3$.

In another embodiment, the SARM compound is represented by a structure of Formulas VIII, IX, X, XI, XII, XIII, and XIV:

VIII

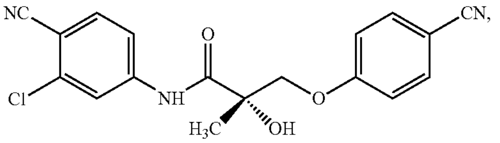

IX

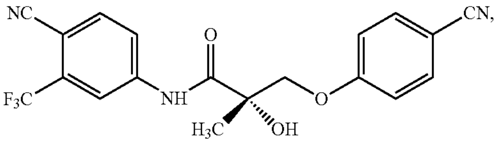

X

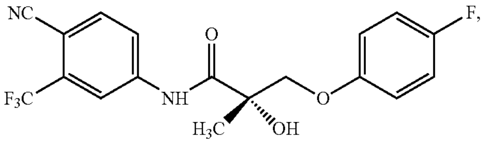

XI

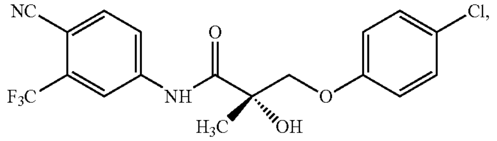

XII

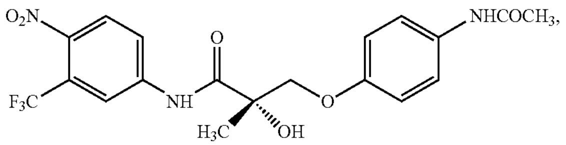

XIII

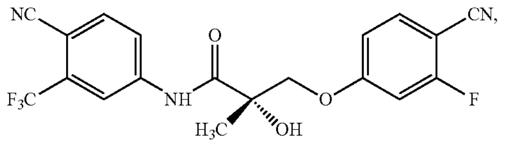 or

-continued

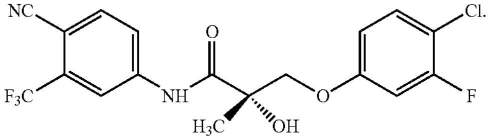

XIV

The methods disclosed herein encompass uses of any one of the SARM compounds disclosed herein in a subject who is under treatment or stops treatment with any one of the SGLT-2 inhibitors disclosed herein, or with any SGLT-2 inhibitor to be developed in the future. For example, the methods disclosed herein comprise use of any one of the SARM compounds represented by the structure of Formula I, II, VIII, IX, X, XI, XII, XIII, or XIV in a subject who is under treatment or stops treatment with any one of the SGLT-2 inhibitors disclosed herein. In one embodiment, the methods disclosed herein comprise use of any one of the SARM compounds represented by the structure of Formula I in a subject who is under treatment or stops treatment with any one of the SGLT-2 inhibitors disclosed herein. In another embodiment, the methods disclosed herein comprise use of any one of the SARM compounds represented by the structure of Formula II in a subject who is under treatment or stops treatment with any one of the SGLT-2 inhibitors disclosed herein. In another embodiment, the methods disclosed herein comprise use of the SARM compound represented by the structure of Formula VIII in a subject who is under treatment or stops treatment with any one of the SGLT-2 inhibitors disclosed herein. In another embodiment, the methods disclosed herein comprise use of the SARM compound represented by the structure of Formula IX in a subject who is under treatment or stops treatment with any one of the SGLT-2 inhibitors disclosed herein. In another embodiment, the methods disclosed herein comprise use of the SARM compound represented by the structure of Formula X in a subject who is under treatment or stops treatment with any one of the SGLT-2 inhibitors disclosed herein. In another embodiment, the methods disclosed herein comprise use of the SARM compound represented by the structure of Formula XI in a subject who is under treatment or stops treatment with any one of the SGLT-2 inhibitors disclosed herein. In another embodiment, the methods disclosed herein comprise use of the SARM compound represented by the structure of Formula XII in a subject who is under treatment or stops treatment with any one of the SGLT-2 inhibitors disclosed herein. In another embodiment, the methods disclosed herein comprise use of the SARM compound represented by the structure of Formula XIII in a subject who is under treatment or stops treatment with any one of the SGLT-2 inhibitors disclosed herein. In another embodiment, the methods disclosed herein comprise use of the SARM compound represented by the structure of Formula XIV in a subject who is under treatment or stops treatment with any one of the SGLT-2 inhibitors disclosed herein. In some embodiments, the SGLT-2 inhibitor is canagliflozin. In some embodiments, the SGLT-2 inhibitor is dapagliflozin. In some embodiments, the SGLT-2 inhibitor is empagliflozin. In some embodiments, the SGLT-2 inhibitor is ertugliflozin. In some embodiments, the SGLT-2 inhibitor is bexagliflozin.

In another embodiment, the methods disclosed herein comprise use of the SARM compound represented by the structure of Formula IX in a subject who is under treatment or stops treatment with the SGLT-2 inhibitor bexagliflozin. In another embodiment, the methods disclosed herein comprise use of the SARM compound represented by the structure of Formula IX in a subject who is under treatment or stops treatment with the SGLT-2 inhibitor canagliflozin. In another embodiment, the methods disclosed herein comprise use of the SARM compound represented by the structure of Formula IX in a subject who is under treatment or stops treatment with the SGLT-2 inhibitor dapagliflozin. In another embodiment, the methods disclosed herein comprise use of the SARM compound represented by the structure of Formula IX in a subject who is under treatment or stops treatment with the SGLT-2 inhibitor empagliflozin. In another embodiment, the methods disclosed herein comprise use of the SARM compound represented by the structure of Formula IX in a subject who is under treatment or stops treatment with the SGLT-2 inhibitor ertugliflozin.

In some embodiments of the methods of the invention as described herein, the subject treated by the methods disclosed herein is overweight or obese. In some embodiments, the subject has prediabetes, diabetes or does not have diabetes. In some embodiments, the subject is a type 2 diabetes patient being obese or overweight. In some embodiments, the subject has sarcopenic obesity. In some embodiments, the subject is 60 years old or older.

In some embodiments, the adverse effects caused by an incretin agonist or antagonist containing drug or a sodium-glucose transport protein 2 (SGLT-2) inhibitor comprise one or more of the following: loss in (i) lean body mass, (ii) muscle strength, (iii) muscle mass, (iv) bone strength, (v) bone mass, or (vi) physical function in the subject. In some embodiments, the loss in lean body mass is from about 5% to 60% of body weight in the subject.

In some embodiments, the methods disclosed herein further result in reducing loss in lean body mass in the subject due to use of an incretin agonist or antagonist containing drug or an SGLT-2 inhibitor, or preventing or reversing bone loss or leading to gaining bone in the subject due to use of an incretin agonist or antagonist containing drug or an SGLT-2 inhibitor. In some embodiments, the methods disclosed herein further result in overcoming insulin resistance in the subject. Insulin resistance (IR) is a characteristic of pre-diabetes and diabetes. Thus, if IR is reduced or overcome, then progression to diabetes in prediabetics can be delayed or prevented. In some embodiments, the IR is exerted in the muscles of pre-diabetes and diabetic subjects. In some embodiments, the IR exerted in the muscles can cause loss of at least one of muscle mass, muscle strength, lean body mass, or physical function. In some embodiments, the IR is exerted in the muscles of pre-diabetes and diabetic subjects can be treated, reduced, or inhibited with a SARM of the invention in combination with a weight loss drug, an SGLT-2 inhibitor, an incretin agonist or antagonist containing drug, a GLP-1 RA and/or a GLP-2 RA.

In some embodiments, the methods disclosed herein further result in one or more of reducing abdominal fat accumulation, improving body composition, lowering body fat content, lowering fat mass, improving blood lipid profile, increasing muscle mass or muscle strength or muscle function, increasing bone mass or BMD or bone strength or bone function, and lowering body fat in the subject. Starvation weight loss, such as with low calorie diets in the absence of exercise, occurs with significant loss both fat body mass (FBM) and lean body mass (LBM). Loss of LBM is detrimental as LBM is composed of tissue that exerts healthy influence on glucose and fat metabolism such as muscle mass, and also tissues required for physical performance such as muscle and bone. Such losses of LBM can be detrimental, especially in the elderly individual and/or an individual which is pre-diabetic and/or an individual which is sarcopenic and/or an individual who is obese. Prevention of such losses in LBM can result in an improvement in quality of life.

Abdominal fat accumulation is a sign of pre-diabetes. It reflects a maldistribution of fat due to metabolic disorders. Thus, if abdominal fat accumulation is reduced, it reflects healthy loss of FBM and/or healthy weight loss. Improving body composition refers to healthy changes in the relative amounts of FBM (obesity and pre-diabetes tend to have excessive FBM; so decreases in FBM is favorable to health in these patients) and LBM (as explained above, LBM promotes glucose uptake and metabolism, fat metabolism, healthy fat distribution, and promotes/supports vigorous physical activity; so increases in LBM are favorable to health). Concomitant decrease in FBM and increase in LBM would be optimal improvement in body composition. Lowering fat mass is synonymous with lowering FBM. Improved blood lipid profiles indicate how well the body is absorbing the dietary fat or fat generated by body metabolism, and whether such fat is being stored as adipose tissue or eliminated from the body. High levels of LDL in the blood are considered unhealthy, correlated with increasing deposition of fat into adipose possibly leading to obesity, and over time cause to deposition of fat in blood vessels, leading to forming plaques, atherosclerosis and/or heart disease; whereas high levels of HDL in the blood are considered healthy, believed correlated with the ability to remove excess fat from the body, and exerting beneficial effects of cardiovascular health. Improving lipid profiles generally refers to increasing HDL to LDL ratio. Increasing muscle mass or muscle strength or muscle function are all correlated with increased LBM, and the beneficial effects of muscle mass, muscle strength, and muscle function are explained above. Exercise promotes the burning of excess calories preventing hyperglycemia and hyperlipidemia, and overtime reduces FBM, as well as promotes increased LBM including increased muscle mass, muscle strength and muscle function. Stronger muscles require stronger bones to support the increased physical activity of exercise. Hence, exercise promotes increasing bone mass, bone mineral density (BMD), bone strength, and bone function. As a person ages, detrimental changes in all these criteria occur, and can be exasperated by the starvation diets to try to lose excess body weight. This can lead to sarcopenic obesity, where FBM is increased and LBM is decreased, and fat metabolism and distribution are maladaptive.

In particular, preserving or augmenting muscle mass is critical for healthy aging. Unfortunately, incretin agonist or antagonist containing drug (e.g., GLP-1 RA) or SGLT-2 monotherapy in overweight or obese elderly and/or overweight or obese pre-diabetics can lead to the same sarcopenic obesity as a result of losses in both FBM and LBM, but also up to 40% of the weight loss as LBM. New methods are needed to allow incretin agonist or antagonist containing drug or SGLT-2 agents to have beneficial effects (loss of FBM) without causing detrimental effects (loss of LBM and physical performance) in the chronic management of weight (weight loss) in overweight and obese people. Selective androgen receptor modulators (SARMs) are known to exert beneficial effects on FBM, fat distribution, LBM, lipid profiles, muscle mass, muscle strength, muscle function, bone mass, BMD, bone strength and bone function, as well as improve insulin resistance. Correspondingly, combining incretin agonist or antagonist containing drug or SGLT-2 therapy with SARM therapy would be beneficial in chronic weight management of obese and pre-diabetics and type 2 diabetics, and particularly in elderly populations most susceptible to sarcopenic obesity. These changes in the above criteria may be beneficial, additive or synergistic effect. If beneficial changes are seen with the combination, then this may result in an improvement in the quality of life with the combination as compared to incretin agonist or antagonist containing drug or SGLT-2 monotherapy.

In one embodiment, the use of a SARM compound (e.g., compound of Formula IX) in combination with an incretin agonist or antagonist containing drug or an SGLT-2 inhibitor would potentiate the loss of total body fat mass associated with incretin agonist or antagonist containing drug or SGLT-2 monotherapy.

In another embodiment, the use of a SARM compound (e.g. compound of Formula IX) in combination with an incretin agonist or antagonist containing drug or an SGLT-2 inhibitor would mitigate the loss of muscle mass associated with incretin agonist or antagonist containing drug or SGLT-2 monotherapy.

In another embodiment, the use of a SARM compound (e.g. compound of Formula IX) in combination with an incretin agonist or antagonist containing drug or an SGLT-2 inhibitor would mitigate the loss of bone and bone mineral density associated with incretin agonist or antagonist containing drug or SGLT-2 monotherapy.

In another embodiment, the use of a SARM compound (e.g. compound of Formula IX) in combination with an incretin agonist or antagonist containing drug or an SGLT-2 inhibitor would potentiate the benefits in HOMA-IR associated with incretin agonist or antagonist containing drug or SGLT-2 monotherapy.

In another embodiment, the use of a SARM compound (e.g. compound of Formula IX) in combination with an incretin agonist or antagonist containing drug or an SGLT-2 inhibitor would potentiate the benefits in HbA1c levels associated with incretin agonist or antagonist containing drug or SGLT-2 monotherapy.

In another embodiment, the use of a SARM compound (e.g. compound of Formula IX) in combination with an incretin agonist or antagonist containing drug or an SGLT-2 inhibitor would result in a physical function benefit compared to incretin agonist or antagonist containing drug or SGLT-2 monotherapy.

In another embodiment, the use of a SARM compound (e.g. compound of Formula IX) in combination with an incretin agonist or antagonist containing drug or an SGLT-2 inhibitor would result in an improvement in quality of life compared to incretin agonist or antagonist containing drug or SGLT-2 monotherapy.

In some embodiments, the SARM compound is administered intravenously, subcutaneously, orally, or topically. In some embodiments, the SARM compound is administered at a dose of from 0.1 mg to 50 mg per day. In some embodiments, the SARM compound is administered at a dose of 0.1 mg per day, 0.3 mg per day, 1 mg per day, 3 mg per day, 5 mg per day, 6 mg per day, 9 mg per day, or 18 mg per day.

In some embodiments, the SARM compound is administered to the subject concurrently with, or prior to, or after the treatment with the incretin agonist or antagonist containing drug. In some embodiments, the incretin agonist or antagonist containing drug and the SARM compound together exhibit a complementary or additive effect. In some embodiments, the incretin agonist or antagonist containing drug and the SARM compound together exhibit a synergistic effect, for example, the efficacy or potency of the incretin agonist or antagonist containing drug in the presence of the SARM compound is greater than that which is expected from the incretin agonist or antagonist containing drug used alone.

In some embodiments, the SARM compound is administered to the subject concurrently with, or prior to, or after the treatment with an SGLT-2 inhibitor. In some embodiments, the SGLT-2 inhibitor and the SARM compound together exhibit a complementary or additive effect. In some embodiments, the SGLT-2 inhibitor and the SARM compound together exhibit a synergistic effect, for example, the efficacy or potency of the SGLT-2 inhibitor in the presence of the SARM compound is greater than that which is expected from the SGLT-2 inhibitor used alone.

Compositions

In some embodiments, the present invention provides a composition comprising an incretin agonist or antagonist containing drug and a selective androgen receptor modulator (SARM) compound. In some embodiments, the present invention provides a composition comprising a pharmaceutical composition comprising an incretin agonist or antagonist containing drug and a pharmaceutical composition comprising a selective androgen receptor modulator (SARM) compound. In some embodiments, the present invention provides a composition comprising an incretin agonist or antagonist containing drug and a selective androgen receptor modulator (SARM) compound, wherein the weight ratio of the incretin agonist or antagonist containing drug and the SARM compound is from 1:50 to 50:1. In some embodiments, the incretin agonist or antagonist containing drug and the SARM compound together exhibit a complementary or additive effect. In some embodiments, the incretin agonist or antagonist containing drug and the SARM compound together exhibit a synergistic effect. In some other embodiments, the present invention provides a composition having a synergistic effect, comprising an incretin agonist or antagonist containing drug and a selective androgen receptor modulator (SARM) compound, wherein the weight ratio of the incretin agonist or antagonist containing drug and the SARM compound is from 1:50 to 50:1. Examples of incretin agonist or antagonist containing drugs have been described above. In one embodiment, the SARM compound is represented by the structure of Formula I described herein. In another embodiment, the SARM compound is represented by the structure of Formula II described herein. In another embodiment, the SARM compound is represented by one of the structures of Formulas VIII, IX, X, XI, XII, XIII, and XIV described herein.

In some embodiments, the weight ratio of the incretin agonist or antagonist containing drug and the SARM compound in the composition is from 1:20 to 20:1.

In some embodiments, the present invention provides a pharmaceutical composition comprising an incretin agonist or antagonist containing drug and a selective androgen receptor modulator (SARM) compound. In some embodiments, the present invention provides a pharmaceutical composition comprising an incretin agonist or antagonist containing drug and a selective androgen receptor modulator (SARM) compound, wherein the weight ratio of the incretin agonist or antagonist containing drug and the SARM compound is from 1:50 to 50:1. In some embodiments, the incretin agonist or antagonist containing drug and the SARM compound together exhibit a complementary or additive effect. In some embodiments, the incretin agonist or antagonist containing drug and the SARM compound together exhibit a synergistic effect. In some other embodiments, the present invention provides a pharmaceutical composition having a synergistic effect, comprising an incretin agonist or antagonist containing drug and a selective androgen receptor modulator (SARM) compound, wherein the weight ratio of the incretin agonist or antagonist containing drug and the SARM compound is from 1:50 to 50:1. Examples of incretin agonist or antagonist containing drugs have been described above. In one embodiment, the SARM compound is represented by the structure of Formula I described herein. In another embodiment, the SARM compound is represented by the structure of Formula II described herein. In another embodiment, the SARM compound is represented by one of the structures of Formulas VIII, IX, X, XI, XII, XIII, and XIV described herein.

In some embodiments, the weight ratio of the incretin agonist or antagonist containing drug and the SARM compound in the pharmaceutical composition is from 1:20 to 20:1.

In one embodiment, the compositions disclosed herein comprise any one of the SARM compounds disclosed herein and any one of the incretin agonist or antagonist containing drugs disclosed herein, or any incretin agonist or antagonist containing drugs to be developed in the future. In one embodiment, the compositions disclosed herein comprise any one of the SARM compounds represented by the structure of Formula I and any one of the incretin agonist or antagonist containing drugs disclosed herein. In another embodiment, the compositions disclosed herein comprise any one of the SARM compounds represented by the structure of Formula II and any one of the incretin agonist or antagonist containing drugs disclosed herein. In another embodiment, the compositions disclosed herein comprise the SARM compound represented by the structure of Formula VIII and any one of the incretin agonist or antagonist containing drugs disclosed herein. In another embodiment, the compositions disclosed herein comprise the SARM compound represented by the structure of Formula IX and any one of the incretin agonist or antagonist containing drugs disclosed herein. In another embodiment, the compositions disclosed herein comprise the SARM compound represented by the structure of Formula X and any one of the incretin agonist or antagonist containing drugs disclosed herein. In another embodiment, the compositions disclosed herein comprise the SARM compound represented by the structure of Formula XI and any one of the incretin agonist or antagonist containing drugs disclosed herein. In another embodiment, the compositions disclosed herein comprise the SARM compound represented by the structure of Formula XII and any one of the incretin agonist or antagonist containing drugs disclosed herein. In another embodiment, the compositions disclosed herein comprise the SARM compound represented by the structure of Formula XIII and any one of the incretin agonist or antagonist containing drugs disclosed herein. In another embodiment, the compositions disclosed herein comprise the SARM compound represented by the structure of Formula XIV and any one of the incretin agonist or antagonist containing drugs disclosed herein. In some embodiments, the incretin agonist or antagonist containing drug is a GLP-1 receptor agonist. In some embodiments, the incretin agonist or antagonist containing drug is a GLP-2 receptor agonist. In some embodiments, the GLP-1 receptor agonist is orforglipron. In some embodiments, the GLP-1 receptor agonist is exenatide. In some embodiments, the GLP-1 receptor agonist is exenatide LAR. In some embodiments, the GLP-1 receptor agonist is liraglutide. In some embodiments, the GLP-1 receptor agonist is taspoglutide. In some embodiments, the GLP-1 receptor agonist is semaglutide. In some embodiments, the GLP-1 receptor agonist is albiglutide. In some embodiments, the GLP-1 receptor agonist is lixisenatide. In some embodiments, the GLP-1 receptor agonist is tirzepatide. In some embodiments, the GLP-1 receptor agonist is aleniglipron. In some embodiments, the GLP-1 receptor agonist is efsubaglutide alfa. In some embodiments, the GLP-1 receptor agonist is utreglutide. In some embodiments, the GLP-1 receptor agonist is bofanglutide. In some embodiments, the GLP-1 receptor agonist is dapiglutide. In some embodiments, the GLP-2 receptor agonist is dapiglutide. In some embodiments, the GLP-2 receptor agonist is teduglutide. In some embodiments, the GLP-2 receptor agonist is glepaglutide. In some embodiments, the GLP-2 receptor agonist is apraglutide.

In some embodiments, the GLP-1 receptor agonist is MET-097i. In some embodiments, the GLP-1 receptor agonist is MET-224o. In some embodiments, the GLP-1 receptor agonist is MET-002o. In some embodiments, the GLP-1 receptor agonist is MET-815i. In some embodiments, the GLP-1 receptor agonist is ecnoglutide. In some embodiments, the GLP-1 receptor agonist is survodutide. In some embodiments, the GLP-1 receptor agonist is mazdutide (Innovent). In some embodiments, the GLP-1 receptor agonist is pemvidutide. In some embodiments, the GLP-1 receptor agonist is cotadutide. In some embodiments, the GLP-1 receptor agonist is retatrutide. In some embodiments, the GLP-1 receptor agonist is orforglipron. In some embodiments, the GLP-1 receptor agonist is maritide. In some embodiments, the GLP-1 receptor agonist is VK2735. In some embodiments, the GLP-1 receptor agonist is CT-388. In some embodiments, the GLP-1 receptor agonist is GL0034. In some embodiments, the GLP-1 receptor agonist is GMA 106. In some embodiments, the GLP-1 receptor agonist is danuglipron. In some embodiments, the GLP-1 receptor agonist is GSBR-1290. In some embodiments, the GLP-1 receptor agonist is ARD-101. In some embodiments, the GLP-1 receptor agonist is ECC5004. In some embodiments, the GLP-1 receptor agonist is MET-097i (MetSera). In some embodiments, the GLP-1 receptor agonist is ASC30 (Ascletis). In some embodiments, the GLP-1 receptor agonist is HRS9531 (Hengrui). In some embodiments, the GLP-1 receptor agonist is HDM1005 (Huandong Medicine). In some embodiments, the GLP-1 receptor agonist is DA-1726 (MetaVia Pharma). In some embodiments, the GLP-1 receptor agonist is MET-097o (MetSera). In some embodiments, the GLP-1 receptor agonist is MET-224o (MetSera). In some embodiments, the GLP-1 receptor agonist is NN-9662 (NovoNordisk). In some embodiments, the GLP-1 receptor agonist is PF-07976016 (Pfizer). In some embodiments, the GLP-1 receptor agonist is TERN-601 (Terns Pharmaceuticals). In some embodiments, the GLP-1 receptor agonist is CT-868 (Roche). In some embodiments, the GLP-1 receptor agonist is HS-10501 (Hansoh). In some embodiments, the GLP-1 receptor agonist is KAI-9531 (Kailera). In some embodiments, the GLP-1 receptor agonist is HS-10535 (Merck). In some embodiments, the GLP-1 receptor agonist is HRS-7535. In some embodiments, the GLP-1 receptor agonist is RGT-075. In some embodiments, the GLP-1 receptor agonist is MD001. In some embodiments, the GLP-1 receptor agonist is HDM1002. In some embodiments, the GLP-1 receptor agonist is BGM0504. In some embodiments, the GLP-1 receptor agonist is NA-931. In some embodiments, the GLP-1 receptor agonist is HM15275. In some embodiments, the GLP-1 receptor agonist is MWN109. In some embodiments, the GLP-1 receptor agonist is MET-002o. In some embodiments, the GLP-1 receptor agonist is MET-815i. In some embodiments, the GLP-1 receptor agonist is amycretin.

In another embodiment, the compositions disclosed herein comprise the SARM compound represented by the structure of Formula IX and the GLP-1 receptor agonist exenatide. In another embodiment, the compositions disclosed herein comprise the SARM compound represented by the structure of Formula IX and the GLP-1 receptor agonist exenatide LAR. In another embodiment, the compositions disclosed herein comprise the SARM compound represented by the structure of Formula IX and the GLP-1 receptor agonist liraglutide. In another embodiment, the compositions disclosed herein comprise the SARM compound represented by the structure of Formula IX and the GLP-1 receptor agonist taspoglutide. In another embodiment, the compositions disclosed herein comprise the SARM compound represented by the structure of Formula IX and the GLP-1 receptor agonist semaglutide. In another embodiment, the compositions disclosed herein comprise the SARM compound represented by the structure of Formula IX and the GLP-1 receptor agonist albiglutide. In another embodiment, the compositions disclosed herein comprise the SARM compound represented by the structure of Formula IX and the GLP-1 receptor agonist lixisenatide. In another embodiment, the compositions disclosed herein comprise the SARM compound represented by the structure of Formula IX and the GLP-1 receptor agonist tirzepatide. In another embodiment, the compositions disclosed herein comprise the SARM compound represented by the structure of Formula IX and the GLP-1 receptor agonist aleniglipron. In another embodiment, the compositions disclosed herein comprise the SARM compound represented by the structure of Formula IX and the GLP-1 receptor agonist efsubaglutide alfa. In another embodiment, the compositions disclosed herein comprise the SARM compound represented by the structure of Formula IX and the GLP-1 receptor agonist utreglutide. In another embodiment, the compositions disclosed herein comprise the SARM compound represented by the structure of Formula IX and the GLP-1 receptor agonist bofanglutide. In another embodiment, the compositions disclosed herein comprise the SARM compound represented by the structure of Formula IX and the GLP-1 receptor agonist dapiglutide. In another embodiment, the compositions disclosed herein comprise the SARM compound represented by the structure of Formula IX and the GLP-2 receptor agonist dapiglutide. In another embodiment, the compositions disclosed herein comprise the SARM compound represented by the structure of Formula IX and the GLP-2 receptor agonist teduglutide. In another embodiment, the compositions disclosed herein comprise the SARM compound represented by the structure of Formula IX and the GLP-2 receptor agonist glepaglutide. In another embodiment, the compositions disclosed herein comprise the SARM compound represented by the structure of Formula IX and the GLP-2 receptor agonist apraglutide. In another embodiment, the compositions disclosed herein comprise the SARM compound represented by the structure of Formula IX and the GLP-1 receptor agonist MET-097i. In another embodiment, the compositions disclosed herein comprise the SARM compound represented by the structure of Formula IX and the GLP-1 receptor agonist MET-224o. In another embodiment, the compositions disclosed herein comprise the SARM compound represented by the structure of Formula IX and the GLP-1 receptor agonist MET-002o. In another embodiment, the compositions disclosed herein comprise the SARM compound represented by the structure of Formula IX and the GLP-1 receptor agonist MET-815i. In another embodiment, the compositions disclosed herein comprise the SARM compound represented by the structure of Formula IX and the GLP-1 receptor agonist dulaglutide. In another embodiment, the compositions disclosed herein comprise the SARM compound represented by the structure of Formula IX and the GLP-1 receptor agonist ecnoglutide. In another embodiment, the compositions disclosed herein comprise the SARM compound represented by the structure of Formula IX and the GLP-1 receptor agonist survodutide. In another embodiment, the compositions disclosed herein comprise the SARM compound represented by the structure of Formula IX and the GLP-1 receptor agonist mazdutide. In another embodiment, the compositions disclosed herein comprise the SARM compound represented by the structure of Formula IX and the GLP-1 receptor agonist pemvidutide. In another embodiment, the compositions disclosed herein comprise the SARM compound represented by the structure of Formula IX and the GLP-1 receptor agonist cotadutide. In another embodiment, the compositions disclosed herein comprise the SARM compound represented by the structure of Formula IX and the GLP-1 receptor agonist retatrutide. In another embodiment, the compositions disclosed herein comprise the SARM compound represented by the structure of Formula IX and the GLP-1 receptor agonist orforglipron. In another embodiment, the compositions disclosed herein comprise the SARM compound represented by the structure of Formula IX and the GLP-1 receptor agonist maritide. In another embodiment, the compositions disclosed herein comprise the SARM compound represented by the structure of Formula IX and the GLP-1 receptor agonist VK2735. In another embodiment, the compositions disclosed herein comprise the SARM compound represented by the structure of Formula IX and the GLP-1 receptor agonist CT-388. In another embodiment, the compositions disclosed herein comprise the SARM compound represented by the structure of Formula IX and the GLP-1 receptor agonist GL0034. In another embodiment, the compositions disclosed herein comprise the SARM compound represented by the structure of Formula IX and the GLP-1 receptor agonist GMA 106. In another embodiment, the compositions disclosed herein comprise the SARM compound represented by the structure of Formula IX and the GLP-1 receptor agonist danuglipron. In another embodiment, the compositions disclosed herein comprise the SARM compound represented by the structure of Formula IX and the GLP-1 receptor agonist GSBR-1290. In another embodiment, the compositions disclosed herein comprise the SARM compound represented by the structure of Formula IX and the GLP-1 receptor agonist ARD-101. In another embodiment, the compositions disclosed herein comprise the SARM compound represented by the structure of Formula IX and the GLP-1 receptor agonist ECC5004. In another embodiment, the compositions disclosed herein comprise the SARM compound represented by the structure of Formula IX and the GLP-1 receptor agonist MET-097i (MetSera). In another embodiment, the compositions disclosed herein comprise the SARM compound represented by the structure of Formula IX and the GLP-1 receptor agonist ASC30 (Ascletis). In another embodiment, the compositions disclosed herein comprise the SARM compound represented by the structure of Formula IX and the GLP-1 receptor agonist HRS9531 (Hengrui). In another embodiment, the compositions disclosed herein comprise the SARM compound represented by the structure of Formula IX and the GLP-1 receptor agonist HDM1005 (Huandong Medicine). In another embodiment, the compositions disclosed herein comprise the SARM compound represented by the structure of Formula IX and the GLP-1 receptor agonist DA-1726 (MetaVia Pharma). In another embodiment, the compositions disclosed herein comprise the SARM compound represented by the structure of Formula IX and the GLP-1 receptor agonist MET-097o (MetSera). In another embodiment, the compositions disclosed herein comprise the SARM compound represented by the structure of Formula IX and the GLP-1 receptor agonist MET-224o (MetSera). In another embodiment, the compositions disclosed herein comprise the SARM compound represented by the structure of Formula IX and the GLP-1 receptor agonist NN-9662 (NovoNordisk). In another embodiment, the compositions disclosed herein comprise the SARM compound represented by the structure of Formula IX and the GLP-1 receptor agonist PF-07976016 (Pfizer). In another embodiment, the compositions disclosed herein comprise the SARM compound represented by the structure of Formula IX and the GLP-1 receptor agonist TERN-601 (Terns Pharmaceuticals). In another embodiment, the compositions disclosed herein comprise the SARM compound represented by the structure of Formula IX and the GLP-1 receptor agonist CT-868 (Roche). In another embodiment, the compositions disclosed herein comprise the SARM compound represented by the structure of Formula IX and the GLP-1 receptor agonist HS-10501 (Hansoh). In another embodiment, the compositions disclosed herein comprise the SARM compound represented by the structure of Formula IX and the GLP-1 receptor agonist KAI-9531 (Kailera). In another embodiment, the compositions disclosed herein comprise the SARM compound represented by the structure of Formula IX and the GLP-1 receptor agonist HS-10535 (Merck). In another embodiment, the compositions disclosed herein comprise the SARM compound represented by the structure of Formula IX and the GLP-1 receptor agonist HRS-7535. In another embodiment, the compositions disclosed herein comprise the SARM compound represented by the structure of Formula IX and the GLP-1 receptor agonist RGT-075. In another embodiment, the compositions disclosed herein comprise the SARM compound represented by the structure of Formula IX and the GLP-1 receptor agonist MD001. In another embodiment, the compositions disclosed herein comprise the SARM compound represented by the structure of Formula IX and the GLP-1 receptor agonist HDM1002. In another embodiment, the compositions disclosed herein comprise the SARM compound represented by the structure of Formula IX and the GLP-1 receptor agonist BGM0504. In another embodiment, the compositions disclosed herein comprise the SARM compound represented by the structure of Formula IX and the GLP-1 receptor agonist NA-931. In another embodiment, the compositions disclosed herein comprise the SARM compound represented by the structure of Formula IX and the GLP-1 receptor agonist HM15275. In another embodiment, the compositions disclosed herein comprise the SARM compound represented by the structure of Formula IX and the GLP-1 receptor agonist MWN109. In another embodiment, the compositions disclosed herein comprise the SARM compound represented by the structure of Formula IX and the GLP-1 receptor agonist MET-002o. In another embodiment, the compositions disclosed herein comprise the SARM compound represented by the structure of Formula IX and the GLP-1 receptor agonist MET-815i. In another embodiment, the compositions disclosed herein comprise the SARM compound represented by the structure of Formula IX and the GLP-1 receptor agonist amycretin.

In some other embodiments, the present invention provides a pharmaceutical composition comprising an SGLT-2 inhibitor and a selective androgen receptor modulator (SARM) compound. In some other embodiments, the present invention provides a pharmaceutical composition comprising an SGLT-2 inhibitor and a selective androgen receptor modulator (SARM) compound, wherein the weight ratio of the SGLT-2 inhibitor and the SARM compound is from 1:50 to 50:1. In some embodiments, the SGLT-2 inhibitor and the SARM compound together exhibit a complementary or additive effect. In some embodiments, the SGLT-2 inhibitor and the SARM compound together exhibit a synergistic effect. In some other embodiments, the present invention provides a pharmaceutical composition having a synergistic effect, comprising an SGLT-2 inhibitor and a selective androgen receptor modulator (SARM) compound, wherein the weight ratio of the SGLT-2 inhibitor and the SARM compound is from 1:50 to 50:1. Examples of SGLT-2 inhibitors have been described above. In one embodiment, the SARM compound is represented by the structure of Formula I described herein. In another embodiment, the SARM compound is represented by the structure of Formula II described herein. In another embodiment, the SARM compound is represented by one of the structures of Formulas VIII, IX, X, XI, XII, XIII, and XIV described herein.

In some embodiments, the weight ratio of the SGLT-2 inhibitor and the SARM compound in the pharmaceutical composition is from 1:20 to 20:1.

In one embodiment, the compositions disclosed herein comprise any one of the SARM compounds disclosed herein and any one of the SGLT-2 inhibitors disclosed herein, or any SGLT-2 inhibitors to be developed in the future. In one embodiment, the compositions disclosed herein comprise any one of the SARM compounds represented by the structure of Formula I and any one of the SGLT-2 inhibitors disclosed herein. In another embodiment, the compositions disclosed herein comprise any one of the SARM compounds represented by the structure of Formula II and any one of the SGLT-2 inhibitors disclosed herein. In another embodiment, the compositions disclosed herein comprise the SARM compound represented by the structure of Formula VIII and any one of the SGLT-2 inhibitors disclosed herein. In another embodiment, the compositions disclosed herein comprise the SARM compound represented by the structure of Formula IX and any one of the SGLT-2 inhibitors disclosed herein. In another embodiment, the compositions disclosed herein comprise the SARM compound represented by the structure of Formula X and any one of the SGLT-2 inhibitors disclosed herein. In another embodiment, the compositions disclosed herein comprise the SARM compound represented by the structure of Formula XI and any one of the SGLT-2 inhibitors disclosed herein. In another embodiment, the compositions disclosed herein comprise the SARM compound represented by the structure of Formula XII and any one of the SGLT-2 inhibitors disclosed herein. In another embodiment, the compositions disclosed herein comprise the SARM compound represented by the structure of Formula XIII and any one of the SGLT-2 inhibitors disclosed herein. In another embodiment, the compositions disclosed herein comprise the SARM compound represented by the structure of Formula XIV and any one of the SGLT-2 inhibitors disclosed herein. In some embodiments, the SGLT-2 inhibitor is canagliflozin. In some embodiments, the SGLT-2 inhibitor is dapagliflozin. In some embodiments, the SGLT-2 inhibitor is empagliflozin. In some embodiments, the SGLT-2 inhibitor is ertugliflozin. In some embodiments, the SGLT-2 inhibitor is bexagliflozin.

In another embodiment, the compositions disclosed herein comprise the SARM compound represented by the structure of Formula IX and the SGLT-2 inhibitor bexagliflozin. In another embodiment, the compositions disclosed herein comprise the SARM compound represented by the structure of Formula IX and the SGLT-2 inhibitor canagliflozin. In another embodiment, the compositions disclosed herein comprise the SARM compound represented by the structure of Formula IX and the SGLT-2 inhibitor dapagliflozin. In another embodiment, the compositions disclosed herein comprise the SARM compound represented by the structure of Formula IX and the SGLT-2 inhibitor empagliflozin. In another embodiment, the compositions disclosed herein comprise the SARM compound represented by the structure of Formula IX and the SGLT-2 inhibitor ertugliflozin.

In a further aspect, the present invention provides a method for preventing, reducing, or treating adverse effects e.g., body composition changes and/or physical function declines, caused by a weight loss drug in a subject who is under treatment or discontinues treatment with the weight loss drug, comprising administering to the subject a therapeutically effective amount of a selective androgen receptor modulator (SARM) compound represented by a structure of Formula I, or an optical isomer, a racemic mixture, a pharmaceutically acceptable salt, a pharmaceutical product, a hydrate, an N-oxide, or a crystal thereof, as disclosed herein. Commonly, discontinuation of a weight loss drug is associated with increased total body weight or total fat mass, limiting the benefit of the weight loss drug course of treatment. This is sometimes referred to as rebound weight gain or rebound fat mass gain. Similarly, lean mass loss or physical function declines can also be associated with use or discontinuation of weight loss drugs. In some aspects, administration of a structure of Formula I prevents, reduces, or treats adverse events of a weight loss drug in a subject who is under treatment or discontinues treatment with a weight loss drug, including, but is not limited to, maintenance of weight loss, maintenance of fat loss, preservation of lean mass, and/or preservation of physical function when a weight loss drug is discontinued or stopped. I.e., administration of a structure of Formula I prevents rebound in total body weight, metrics of body composition (fat mass and lean mass) and physical function when treatment with a weight loss drug is stopped or discontinued.

In some embodiments, the weight loss drug is an incretin agonist or antagonist containing drug, wherein the incretin agonist or antagonist containing drug is a glucagon-like peptide-1 (GLP-1) receptor agonist, a glucose-dependent insulinotropic polypeptide (GIP) antagonist, a GIP agonist, and/or a glucagon agonist, and/or an amylin agonist, and/or oxyntomodulin agonist, or any combination thereof. In some embodiments, the incretin agonist or antagonist containing drug is a GLP-1 receptor agonist. In some embodiments, the incretin agonist or antagonist containing drug is a GLP-1 RA and a GIP agonist. In some embodiments, the incretin agonist or antagonist containing drug is a GLP-1 RA and a GIP antagonist. In some embodiments, the incretin agonist or antagonist containing drug is a GLP-1 RA and a GIP agonist and a glucagon agonist. In some embodiments, the incretin agonist or antagonist containing drug is a GLP-1 RA and an amylin agonist. In some cases, a single molecule possesses more than one type of incretin activity. In some cases, multiple molecules are used to achieve multiple types of incretin activity including antagonism. In some cases, a single molecule possesses any of the types of activity listed above.

In another aspect, the present invention provides a method to prevent, reduce, or treat lean mass loss in a subject who is under treatment or stops treatment with the weight loss drug, comprising administering to the subject a therapeutically effective amount of a selective androgen receptor modulator (SARM) compound represented by a structure of Formula I as disclosed herein.

In another aspect, the present invention provides a method for decreasing fat mass while preserving or increasing lean mass in a subject who is under treatment or stops treatment with weight loss drug, comprising administering to the subject a therapeutically effective amount of a selective androgen receptor modulator (SARM) compound represented by a structure of Formula I as disclosed herein. In some embodiments, the weight loss drug is an incretin agonist or antagonist containing drug. In some embodiments, the incretin agonist or antagonist containing drug is a GLP-1 receptor agonist. In some embodiments, the GLP-1 receptor agonist is orforglipron, semaglutide, or tirzepatide.

In another aspect, the present invention provides a method for decreasing fat mass while preserving or increasing lean mass, and further increasing or preserving physical function in a subject who is under treatment or stops treatment with a weight loss drug, comprising administering to the subject a therapeutically effective amount of a selective androgen receptor modulator (SARM) compound represented by a structure of Formula I. In some embodiments, the weight loss drug is an incretin agonist or antagonist containing drug. In some embodiments, the weight loss drug is an incretin agonist or antagonist containing drug selected from any one of orforglipron, exenatide, exenatide LAR, liraglutide, taspoglutide, semaglutide, albiglutide, lixisenatide, tirzepatide, retatrutide, aleniglipron, efsubaglutide alfa, utreglutide, bofanglutide, dapiglutide, teduglutide, glepaglutide, apraglutide, MET-097i, MET-224o, MET-002o, MET-815i, or dulaglutide. In some embodiments, the incretin agonist or antagonist containing drug is a GLP-1 receptor agonist. In some embodiments, the GLP-1 receptor agonist is semaglutide. In some embodiments, the GLP-1 receptor agonist is tirzepatide. In some embodiments, the GLP-1 receptor agonist is orforglipron. In some embodiments, the present invention provides a method for further preventing, reducing, and treating muscle weakness, poor balance, decreased gait speed, mobility disability, loss of independence, increased risk of falls, bone fractures, loss of physical function, physical disability, poor quality of life, high hospitalization rates, and/or increased mortality in the subject. In some embodiments, the bone fractures are fractures of the hip or pelvis in the subject. In some embodiments, (1) the subject has sarcopenic obesity, and/or (2) the subject is 60 years old or older. In some embodiments, the subject has pre-diabetes, type 2 diabetes, or does not have diabetes.

In one aspect, the present invention provides a method for maintenance or improvement of body composition in a subject who is under treatment or stops treatment with a weight loss drug, comprising administering to the subject a therapeutically effective amount of a selective androgen receptor modulator (SARM) compound, wherein the selective androgen receptor modulator (SARM) compound is represented by a structure of Formula I as disclosed herein. In some embodiments, the present invention maintains or improves body composition by further decreasing fat mass while preserving or increasing lean mass in a subject who is under treatment with the co-administered weight loss drug and the SARM compound, relative to a subject who is under treatment with the weight loss drug alone. In some embodiments, the present invention maintains or improves body composition and further maintains or improves physical function or muscle strength in a subject who is under treatment with the co-administered weight loss drug and the SARM compound, relative to a subject who is under treatment with the weight loss drug alone.

In some of these embodiments, (1) the subject has sarcopenic obesity, and/or (2) the subject is 60 years old or older. In some of these embodiments, the weight loss drug is an incretin agonist or antagonist containing drug, wherein the incretin agonist or antagonist is a glucagon-like peptide-1 (GLP-1) receptor agonist, a glucagon-like peptide-2 (GLP-2) receptor agonist, a glucose-dependent insulinotropic polypeptide (GIP) antagonist, or a GIP agonist, and/or a glucagon agonist, and/or an amylin agonist, and/or an oxyntomodulin agonist or any combination thereof. In some of these embodiments, the incretin agonist or antagonist containing drug further contains an amylin mimetic. In some of these embodiments, the incretin agonist or antagonist containing drug is any one of orforglipron, exenatide, exenatide LAR, liraglutide, taspoglutide, semaglutide, albiglutide, lixisenatide, tirzepatide, retatrutide, maritide, aleniglipron, efsubaglutide alfa, utreglutide, bofanglutide, dapiglutide, teduglutide, glepaglutide, apraglutide, MET-097i, MET-224o, MET-002o, MET-815i, VK2735, or dulaglutide, or wherein the incretin agonist or antagonist containing drug is semaglutide. In some embodiments, the method prevents, reduces, or treats rebound of one or more of weight gain, fat mass gain, lean mass loss, and muscle strength or physical function loss when the weight loss drug is discontinued. In some embodiments, the method results in preservation or restoration of lean body mass (LBM) or muscle in the subject. In some embodiments, the method maintains fat loss or prevents fat regain. In some embodiments, the SARM compound is administered to the subject concurrently with, or prior to, or after the treatment with the weight loss drug. In some of these embodiments, the SARM compound is represented by a structure of Formula IX, as disclosed herein. In some of these embodiments, the incretin agonist or antagonist containing drug is semaglutide and the SARM is Formula IX. In some of these embodiments, the incretin agonist or antagonist containing drug is tirzepatide and the SARM is Formula IX. In some of these embodiments, the incretin agonist or antagonist containing drug is orforglipron and the SARM is Formula IX.

In one aspect, the present invention provides a method wherein the SARM compound is administered at a dose of from 0.1 mg to 50 mg per day, or wherein the SARM compound is administered at a dose of 0.1 mg per day, 0.3 mg per day, 1 mg per day, 3 mg per day, 6 mg per day, 9 mg per day, or 18 mg per day.

In a further aspect, the present invention provides a composition comprising a pharmaceutical composition of Formula IX, or an optical isomer, a racemic mixture, a pharmaceutically acceptable salt, a pharmaceutical product, a hydrate, an N-oxide, or a crystal thereof; and a pharmaceutical composition of semaglutide:

IX

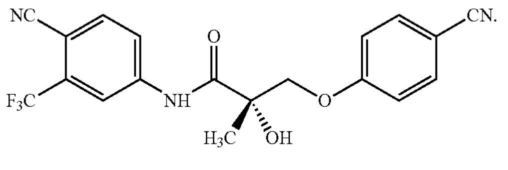

In another aspect, the present invention provides a method for reducing or treating adverse effects caused by semaglutide monotherapy, comprising co-administering to the subject the pharmaceutical composition of Formula IX and the pharmaceutical composition of semaglutide of a composition of the invention as described herein.

In some embodiments of the method of the invention, (i) the subject has obesity and (ii) the subject is 60 years old or older. In some cases, the subject has prediabetes, diabetes mellitus, or does not have diabetes.

In some embodiments, the adverse effects comprise one or more of loss in (i) lean body mass, fat-free mass, or muscle mass, (ii) muscle strength, and (iii) physical function. In certain embodiments, the loss in lean body mass is from about 3% to 20% of the total body weight in the subject.

In some embodiments, the method of the invention results in one or more of (i) reducing the loss of lean body mass, preserving lean body mass, or gaining lean body mass (muscle mass) in the subject, (ii) reversing bone loss or gaining bone in the subject, (iii) overcoming or improving insulin resistance in the subject, and (iv) improving HbA1c in the subject.

In some embodiments, the method of the invention results in one or more of reducing abdominal, subcutaneous, or intramuscular fat accumulation, improving body composition, lowering body fat content, lowering fat mass, or increasing or preserving muscle mass or muscle strength or muscle physical function in the subject.

In some embodiments, the method of the invention results in preservation or restoration of lean body mass (LBM) or muscle in the subject, or wherein the method enhances fat loss or prevents fat regain.

In some embodiments, the method of the invention reduces or treats muscle weakness, poor balance, decreased gait speed, mobility disability, loss of independence, increased risk of falls, bone fractures, loss of physical function, physical disability, poor quality of life, high hospitalization rates, and/or increased mortality in the subject. In some embodiments, the bone fractures are fractures of the hip or pelvis in the subject.

In some embodiments of the method of the invention, the Formula IX is administered to the subject concurrently with or after the treatment with the semaglutide.

In some embodiments, the method of the invention reduces or treats lean mass loss in a subject who is under treatment or stops treatment with the semaglutide.

In some embodiments, the method of the invention decreases fat mass while preserving or increasing lean mass in the subject.

In some embodiments, the method of the invention improves physical function.

In some embodiments, the method of the invention described herein reduces and treats muscle weakness, poor balance, decreased gait speed, mobility disability, loss of independence, increased risk of falls, bone fractures, loss of physical function, physical disability, poor quality of life, high hospitalization rates, and/or increased mortality in the subject. In some embodiments, the bone fractures are fractures of the hip or pelvis in the subject.

In some embodiments, the method of the invention described herein reduces or treats lean mass loss in a subject who is under treatment or stops treatment with the semaglutide, and further decreases fat mass.

In some embodiments, the method of the invention described herein reduces or treats lean mass loss in a subject who is under treatment or stops treatment with the semaglutide, and further improves physical function.

In some embodiments, the method of the invention described herein reduces or treats lean mass loss in a subject who is under treatment or stops treatment with the semaglutide, and further decreases fat mass and improves physical function.

In some embodiments, the method of the invention described herein reduces or treats lean mass loss in a subject who is under treatment or stops treatment with the semaglutide, and further reduces and treats muscle weakness, poor balance, decreased gait speed, mobility disability, loss of independence, increased risk of falls, bone fractures, loss of physical function, physical disability, poor quality of life, high hospitalization rates, and/or increased mortality in the subject. In some embodiments, the bone fractures are fractures of the hip or pelvis in the subject.

In a further aspect, the present invention provides a method for maintenance or improvement of body composition compared to semaglutide monotherapy, comprising co-administering to the subject the pharmaceutical composition of Formula IX and the pharmaceutical composition of semaglutide of a composition of the invention as described herein.

In some embodiments of the method for maintenance or improvement of body composition, the subject discontinues semaglutide, but continues treatment with Formula IX, or an optical isomer, a racemic mixture, a pharmaceutically acceptable salt, a pharmaceutical product, a hydrate, an N-oxide, or a crystal thereof, as monotherapy:

IX

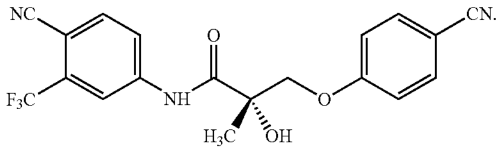

In some embodiments, the improved body composition is represented by further decreasing fat mass while preserving or increasing lean mass in a subject who is under treatment with the co-administered semaglutide and Formula IX or stops treatment with semaglutide, relative to a subject who is under treatment with the semaglutide alone.

In some embodiments, the improved body composition is represented by further decreasing fat mass while preserving or increasing lean mass in a subject who was co-administered the semaglutide and the Formula IX, and then the semaglutide is discontinued; relative to a subject who is under treatment with the semaglutide alone.

In some embodiments, the physical function or muscle strength is maintained or improved. In some embodiments, (i) the subject has obesity and/or (ii) the subject is 60 years old or older. In some embodiments, the method reduces or treats rebound of one or more of (i) weight gain, (ii) fat mass gain, and (iii) lean mass loss when the semaglutide is discontinued. In some embodiments, the method results in preservation or restoration of lean body mass (LBM) or muscle in the subject. In some embodiments, the method of the invention augments fat loss or prevents fat regain.

In some embodiments of a composition of the invention as described herein, the Formula IX is formulated for administration at a dose of from 0.1 mg to 50 mg per day, or wherein the Formula IX is formulated for administration at a dose of 3 mg per day or 6 mg per day, and wherein the semaglutide is formulated for administration at the dose of from 0.25 mg per week to 1.7 mg per week.

In a further aspect, the present invention provides a method of reducing or treating rebound in a subject, wherein the rebound is in one or more of (i) weight gain, (ii) fat mass gain, and (iii) lean mass loss when the semaglutide treatment is discontinued in said subject but Formula IX treatment continues as monotherapy:

IX

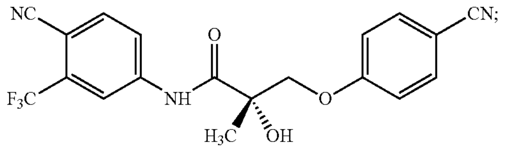

wherein the subject was previously co-administered the pharmaceutical composition of Formula IX and the pharmaceutical composition of semaglutide of a composition of the invention as described herein.

In some embodiments of the method of the invention described herein, the method results in preservation or restoration of lean body mass (LBM) or muscle in the subject, or wherein the method enhances fat loss or prevents fat regain. In some embodiments, the Formula IX is administered to the subject concurrently with or after the treatment with the semaglutide. In some embodiments, the method reduces or treats lean mass loss in a subject who is under treatment or stops treatment with the semaglutide.

Various embodiments and aspects of the present invention as delineated hereinabove and as claimed in the claims section below find experimental support in the following examples.

Example 1

Examining Uses of SARM Compounds in Chronic Weight Management

The present example describes experiments to examine the effects of using SARMs in chronic weight management and to mitigate adverse effects caused by incretin agonist or antagonist containing drugs, glucagon-like peptide-1 (GLP-1) receptor agonists or sodium-glucose transport protein 2 (SGLT-2) inhibitors. In one embodiment, Formula IX (enobosarm), a selective androgen receptor modulator (SARM), is examined in a Phase 2b clinical trial in combination with weight-loss GLP-1 receptor agonist drugs, Ozempic® (semaglutide), Wegovy® (semaglutide), orforglipron, or Mounjaro® (tirzepatide) or SGLT-2 inhibitor drugs Brenzavvy™ (bexagliflozin), Invokana® (canagliflozin), Farxiga® (dapagliflozin), Jardiance® (empagliflozin), or Steglatro® (ertugliflozin) to evaluate the efficacy and the safety of Formula IX to augment fat loss while preventing the significant loss of lean body mass (LBM) that occurs with the weight loss drugs such as incretin agonist or antagonist containing drugs, GLP-1 receptor agonists or SGLT-2 inhibitors. Detailed clinical protocol given in Example 6.

Weight loss from medications such as orforglipron, or Ozempic® (semaglutide), Wegovy® (semaglutide), or Mounjaro® (tirzepatide), or liraglutide, or Brenzavvy™ (bexagliflozin), Invokana® (canagliflozin), Farxiga® (dapagliflozin), Jardiance® (empagliflozin), or Steglatro® (ertugliflozin) results from the collective loss of fat mass and lean mass (muscle and bone). Muscle is critical for metabolism, muscle strength and physical function (mobility) and prevention of injury (falls) especially in an older population (>60 years of age). According to the CDC, 42% of older adults have obesity and could benefit from weight loss medication, but the high amount of loss of lean body mass (LBM) that occurs with these weight loss drugs reduces the muscle mass to sarcopenic, or critically low, amounts which may result in muscle weakness leading to poor balance, decreased gait speed, mobility disability, loss of independence, falls, bone fractures, higher hospitalizations and increase mortality. Obese patients that have sarcopenic obesity, a common subgroup, have both obesity and age-related low muscle mass at the same time and are potentially at the greatest risk for developing critically low muscle mass and muscle weakness when taking the GLP-1 drugs or SGLT-2 medications for weight loss.

In a study by Wilding et al. reported in The New England Journal of Medicine (N. Engl. J. Med. 2021, 384, 989-1002), a subgroup analysis was conducted in 140 subjects from the Obesity (STEP 1) Trial which evaluated semaglutide 2.4 mg a week treatment compared to placebo for 68 weeks. In this analysis, semaglutide treatment resulted in the average loss of 10.43 kg (22.9 lbs) of fat and 6.92 kg (15.2 lbs) of muscle mass which means that muscle loss made up 40% of the total weight lost. Similarly, Sargeant et al. observed that treatment with GLP-1 receptor agonists or sodium glucose cotransporter 2 inhibitors (SGLT2i; same as SGLT-2 inhibitors) resulted in a lean body mass loss (muscle) that made up 20-50% of the total weight loss.

Formula IX is an oral, new chemical entity, new class, selective androgen receptor targeting agent or modulator (SARM) that has demonstrated tissue-selective, dose-dependent increases in muscle mass (lean body mass), reduces fat mass, improves insulin resistance, while sparing other androgenic tissue with no masculinizing effects in women, prostate neutral effects in men. Increases in muscle mass have resulted in improvements in muscle strength and physical function. In preclinical studies in male and female mice, Formula IX demonstrated the ability to increase muscle mass, reduce lipogenesis and stimulate lipolysis, as well as prevent and treat bone loss. Formula IX has extensive nonclinical and clinical experience having been evaluated in at least 27 separate clinical studies in approximately 1,600 subjects dosed. Five clinical studies for a total of 968 patients (see Table 1 below) measured muscle mass endpoints which was included in two Phase 2 clinical studies in healthy older or sarcopenic subjects (168 subjects) and one Phase 2b and two Phase 3 studies in subjects with muscle wasting because of cancer (800 subjects). Muscle wasting caused by cancer creates a 'starvation state' by suppressing appetite resulting in significant loss of both lean body mass and fat mass which is similar to what has been observed with GLP-1 and SGLT-2 and other drugs for weight loss. Formula IX treatment in elderly men and postmenopausal women participants with and without active muscle wasting consistently resulted in the reduction in fat mass and significant increases in lean body mass (muscle) with improvements in muscle strength and physical function. Formula IX, which has a large safety database, was generally well tolerated in both men and women.

TABLE 1

| Subjects (n=) | Phase | Population | Purpose | Muscle (LBM) | Muscle strength/ function | Fat Mass | Duration | Source |
|---|---|---|---|---|---|---|---|---|
| 120 (24 received Formula IX 3 mg) | 2 | Males over 60 years of age and postmenopausal women (Study G200501) | Dose-finding (0.1 mg-3 mg) | 3 mg = 1.25 kg increase ($p < 0.001$ compared to placebo) | 3 mg 17% Increase SCP ($p = 0.049$ compared to placebo) | 3 mg = 0.32 kg decrease ($p = 0.049$ compared to placebo) Representing a 2-5% decrease of total fat mass | 12 weeks | Dalton JT J Cachexia Sarcopenia Muscle 2: 153, 2011 and clinical study report (CSR) |
| 48 (12 received Formula IX 3 mg) | 2 | Sarcopenic postmenopausal women (Study 003) | Double-blind placebo controlled (3 mg) | 3 mg = 1.54 kg increase ($p < 0.001$ compared to placebo) | Bilateral leg press at 3 mg produced a 21.96 lbs. increase from baseline vs placebo had 1.5 lbs. increase from baseline | Not collected | 12 weeks | Merck study CSR (on file) |
| 159 (41 received Formula IX 3 mg) | 2b | Muscle wasting cancer (Study G200502) | Double-blind placebo controlled (1 and 3 mg) | 3 mg = 1.3 kg increase ($p = 0.041$ compared to baseline) | 3 mg 16.8 watt increase SCP. ($p = 0.001$ compared to baseline) | 3 mg = 0.76 kg decrease in total fat mass ($p = 0.086$ compared to placebo) | 16 weeks | Dobs AS Lancet Oncology 14: 335, 2013 And CSR |
| 321 (160 received Formula IX 3 mg) | 3 | Lung cancer muscle wasting receiving cisplatin + taxane chemotherapy (Study G300504) | Double-blind placebo controlled (3 mg) | 0.8 kg Increase in LBM at Day 84 ($p < 0.001$ from baseline) Higher mean slope of the change from baseline than placebo ($p = 0.0002$ Day 84 and $p < 0.0001$ Day 147) | 5.17% Increased in SCP at Day 84 vs. −1.27% in the placebo Higher mean slope of the change from baseline ($p = 0.0147$ at Day 84, $p = 0.049$ at Day 147) | Not reported | 21 weeks | CSR (on file) |
| 320 (159 received Formula IX 3 mg) | 3 | Lung cancer muscle wasting receiving cisplatin + nontaxane chemotherapy (Study G300505) | Double-blind placebo controlled (3 mg) | 0.73 kg Increase in LBM Day 84 and 0.67 kg increase at Day 147 ($p = 0.013$) Higher mean slope of the change from baseline compared to placebo ($p = 0.0111$ at Day 84, and $p = 0.0028$ at Day 147) | SCP N.S. | Not reported | 21 weeks | CSR (on file) |

Sarcopenic = presence of severe muscle loss beyond 2 standard deviations of the age matched healthy
LBM = lean body mass
SCP = stair climb power (Watts), power exerted in a 12-step stair climb
CSR = clinical study report
N.S. = not significant Given the extensive clinical experience with Formula IX, in both older patients and in patients with muscle wasting caused by suppressed appetite (cancer induced muscle wasting), the combination of Formula IX and semaglutide or tirzepatide or orforglipron (or, alternatively, an SGLT-2 inhibitor) therapy for weight loss or diabetes is expected to provide additional clinical benefit and ameliorate adverse loss of lean body mass due to GLP-1 agents (e.g. semaglutide, tirzepatide, or orforglipron) or SGLT-2 agents (e.g. bexagliflozin, canagliflozin, dapagliflozin, empagliflozin or ertugliflozin). Specifically, Formula IX therapy could augment the fat mass loss while preventing the loss of or possibly increasing critical muscle mass and bone mineral density. Based on the Obesity (Step 1) Phase 3 substudy, GLP-1 semaglutide decreased lean body mass by 6.92 kg over 68 weeks, and Formula IX has demonstrated in clinical studies the ability to increase or maintain muscle mass. By maintaining or preserving muscle (LBM), weight loss plateau during GLP-1 RA therapy may be improved and the maintenance of weight loss following cessation of GLP-1 RA therapy is expected.

A Phase 2b, multicenter, double-blind, placebo-controlled, randomized, dose-finding clinical trial was conducted to evaluate the safety and efficacy of Formula IX 3 mg, Formula IX 6 mg, or placebo as a treatment to preserve muscle and augment fat loss in approximately 168 patients with sarcopenic obesity or overweight elderly (>60 years of age) patients receiving semaglutide (Wegovy®). The primary endpoint was total lean body mass, and the key secondary endpoints were total body fat mass and physical function as measured by stair climb test at 16 weeks.

After completing the efficacy dose-finding portion of the Phase 2b clinical trial, participants continued in blinded fashion into a Phase 2b extension clinical trial where all patients stopped receiving a GLP-1 RA, but continued taking placebo, Formula IX 3 mg, or Formula IX 6 mg for an additional 12 weeks. The Phase 2b extension clinical trial will evaluate whether Formula IX can maintain muscle and prevent the fat and weight gain that occurs after discontinuing a GLP-1 RA. This clinical trial was described in detail in Example 6.

This Phase 2b study addressed loss of lean body mass caused by GLP-1 agents (semaglutide or tirzepatide or orforglipron) or SGLT-2 agents (bexagliflozin, canagliflozin, dapagliflozin, empagliflozin or ertugliflozin) which reduce muscle mass in elderly patients to levels that may lead to higher risk for mobility disability and falls. To prevent muscle loss and bone loss during the GLP-1 agent induced starvation state, the goal was to maintain muscle and lose fat preferentially. Another potential future indication is to treat muscle loss in older patients that have stopped treatment with GLP-1 agents (semaglutide or tirzepatide or orforglipron) or SGLT-2 agents (bexagliflozin, canagliflozin, dapagliflozin, empagliflozin or ertugliflozin) as fat will return before muscle, leaving the at-risk elderly patients in a state of sarcopenia, or critically low muscle mass. Therapeutic objective for this additional indication is to reduce fat and to increase the amount of muscle mass above the critical threshold and to maintain a better long term body composition (muscle/fat ratio) after stopping GLP-1 agent or SGLT-2 agent treatment.

In summary, in 5 clinical studies involving 968 older men and postmenopausal women with and without muscle wasting, Formula IX has demonstrated the ability to decrease fat mass, increase muscle mass, and improve muscle strength and physical function. Weight-loss drugs like orforglipron, Ozempic®, Wegovy®, Mounjaro® and other GLP-1 drugs or SGLT-2 agents (bexagliflozin, canagliflozin, dapagliflozin, empagliflozin or ertugliflozin) cause significant loss of both fat and muscle. In older obese patients who may already have low muscle mass (sarcopenic obesity), the further drop in muscle mass of all-important muscles increases risk of muscle weakness, mobility disability, falls, higher hospitalizations, and greater mortality. A Phase 2b double-blind, placebo-controlled study was conducted to evaluate Formula IX and GLP-1 drug combination for weight loss that prevented muscle loss and increased fat loss and prevented physical function decline in overweight or obese subjects (Examples 6 and 7).

Example 2

Phase 1 Study of Formula IX in Healthy Young and Older Men

Formula IX is a novel oral selective androgen receptor modulator that has been shown to increase lean mass and decrease fat mass. There is a need for a therapy that can prevent the loss of muscle mass, while further increasing fat loss to improve adverse body composition changes in patients taking GLP-1 RA for weight loss, especially in older sarcopenic obese patients who are at-risk for developing muscle atrophy and muscle weakness leading to frailty.

Methods: A double-blind, randomized, placebo-controlled, single-center, multiple ascending dose Phase 1 study was conducted in normal-weight healthy young (18-45y; 27±7y) and older men (≥60y; 67±5y). The study was of sequential dose escalation design (young men 1, 3, 10 and 30 mg; older men 3 and 30 mg) with separate groups receiving oral dose of Formula IX vs matching placebo (n=72). The Phase 1 study assessed the safety and pharmacokinetics of a dose range that covers the projected clinical dose range of up to 3 mg per day. A DXA scan was obtained to assess early changes in body composition. A main objective of this study was to compare the effects of Formula IX in young healthy normal-weight men with that observed in older men.

TABLE 2

Total lean and fat mass changes from baseline in young and older men after 14 days of Formula IX or placebo treatment (mean ± SD).

| Young men | Placebo | Formula IX (3 mg) |
|---|---|---|
| N | 12 | 9 |
| Total lean mass | −0.70% (±2.53%) | 1.43% (±2.37%) |
| Total fat mass | 3.72% (±3.92%) | 0.69% (±3.02%) |
| Age (years) | 27.16 (±7.09) | 26 (±7.87) |
| BMI ($kg/m^2$) | 24.07 (±2.15) | 23.44 (±1.69) |
| **Older men** | **Placebo** | **Formula IX (3 mg)** |
| N | 5 | 9 |
| Total lean mass | −0.95% (±2.04%) | 3.03% (±2.75%) |
| Total fat mass | 2.33% (±4.47%) | −1.16% (±4.16%) |
| Age (years) | 68.4 (±5.45) | 67.77 (±5.24) |
| BMI ($kg/m^2$) | 26.7 (±1.63) | 27.92 (±3.18) |

Results: pharmacokinetic (PK) parameters were similar between young and older men. In the placebo groups, the changes in total lean mass and total fat mass were similar between the young and older men. There was a placebo corrected 2.13% and 3.98% increase in total lean mass from baseline with Formula IX 3 mg in the young and older men after 14 days of treatment, respectively. A placebo corrected 3.03% and 3.49% decrease in total fat mass with Formula IX 3 mg in young and older men, respectively (Table 2). Formula IX was generally safe and well tolerated.

Conclusion: With short term 14-day exposure of Formula IX treatment, similar increases in total lean mass and decreases in total fat mass were observed in young and older men compared to placebo. While Formula IX was associated with positive body composition changes in men regardless of age, older men with lower lean mass and higher fat mass at baseline appear more likely to have greater benefit from Formula IX therapy.

Example 3

Augment Reduction of Fat Mass while Preserving Muscle in Older Patients with Obesity Formula IX has been studied in 5 clinical muscle studies involving 968 older men, postmenopausal women, and older patients who have muscle loss due to advanced cancer. Advanced cancer suppresses appetite causing weight loss and muscle wasting. The totality of the clinical data demonstrates that Formula IX therapy results in dose-dependent reductions in fat mass and increases in muscle mass with improvement in physical function.

Methods: A placebo-controlled Phase 3 clinical trial was conducted evaluating oral daily 3 mg Formula IX dose for the treatment of muscle wasting in advanced lung cancer patients undergoing chemotherapy. A post-hoc analysis was performed to assess body composition by DXA scan in a subset of older (≥60 years) patients with obesity (BMI ≥30 kg/$m^2$) at 12 and 21 weeks. Loss of appetite occurs with advanced cancer inducing a hypocaloric state, similar to GLP-1 RA therapy.

Figure 1B:
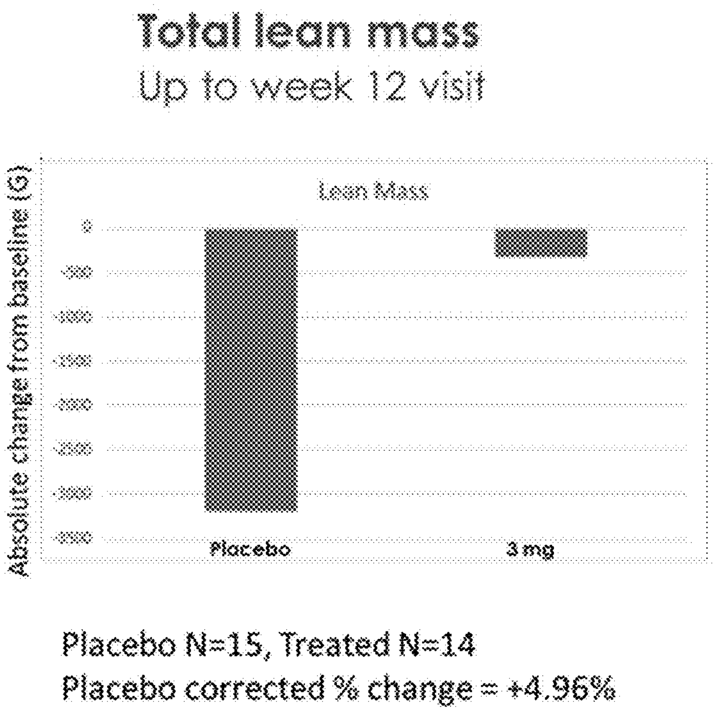
Figure 1C:
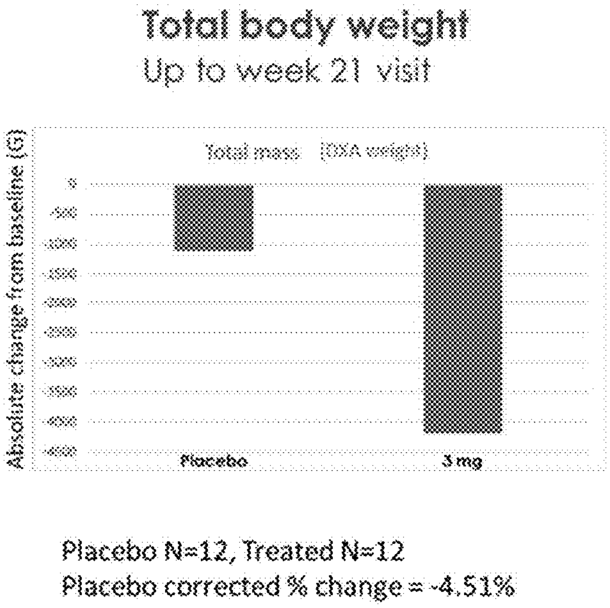

Results: At 12 weeks, Formula IX 3 mg treated subjects had maintained while placebo lost total lean body mass (n=29). Formula IX 3 mg treated subjects had a 5.77% reduction in fat mass compared to placebo (n=29). By 21 weeks, Formula IX 3 mg treatment resulted in a 14.4% total fat mass loss, a 0.35% increase in total lean mass, and a 4.5% loss of DXA body weight compared to placebo (n=24) (FIGS. 1A, 1B, and 1C). Formula IX was generally well tolerated with no increase in frequency of gastrointestinal side effects compared to placebo.

Conclusion: In a subset analysis of older patients who have obesity, Formula IX therapy resulted in reductions in fat mass while preserving lean body mass (muscle) leading to greater high quality weight loss. This supports the potential for Formula IX monotherapy to preferentially reduced fat mass while preserving lean mass in patients with obesity, including those that discontinued GLP-1 RA treatment due to toxicity or other reasons.

Example 4

Pooled Safety Analysis of Formula IX from Phase 2 and Phase 3 Placebo-Controlled Clinical Trials A pooled analysis was conducted from randomized clinical trials (RCT) to evaluate the safety profile of Formula IX.

Methods: The pooled safety analysis of Formula IX (3 mg) included: Phase 2 study in older males (≥60 years old) and postmenopausal women (n=48), two Phase 3 studies in patients with advanced lung cancer (n=651), and Phase 2 stress urinary incontinence (*SUI*) in women study (n=328).

Results: The pooled analysis of 4 RCT consisted of 515 placebo (PBO) and 512 Formula IX treated primarily non-obese subjects. Treatment emergent adverse events (TEAEs) observed with Formula IX were comparable to the placebo group. Most common adverse events (AEs) were nausea (26.6% in Formula IX vs 26.0% in placebo), anemia (25.6% in Formula IX vs 23.9% in placebo), and vomiting (14.8% in Formula IX vs 14.6% in placebo), which were similar to the placebo groups. Notably, there was no increase in gastrointestinal side effects and no evidence of drug induced liver injury with Formula IX compared to placebo treatment. The incidence of deep vein thrombosis was higher (3.3%) in the placebo group compared to the Formula IX group (1.0%) (Table 3—TEAEs in at least 2% of the patients in either PBO or 3 mg Formula IX and at least 1% higher in one of the two groups).

TABLE 3

| | Placebo N = 515 | Formula IX 3 mg N = 512 |
|---|---|---|
| Anaemia | 123 (23.9%) | 131 (25.6%) |
| Neutropenia | 86 (16.7%) | 71 (13.9%) |
| Diarrhoea | 49 (9.5%) | 38 (7.4%) |
| Asthenia | 47 (9.1%) | 58 (11.3%) |
| Chest pain | 24 (4.7%) | 14 (2.7%) |
| Condition aggravated | 12 (2.3%) | 7 (1.4%) |
| Disease progression | 63 (12.2%) | 51 (10.0%) |
| Bronchitis | 9 (1.7%) | 15 (2.9%) |
| Pneumonia | 27 (5.2%) | 19 (3.7%) |
| Urinary tract infection | 26 (5.0%) | 33 (6.4%) |
| Alanine aminotransferase (ALT) increased | 7 (1.4%) | 19 (3.7%) |
| Blood creatinine increased | 20 (3.9%) | 35 (6.8%) |
| Decreased appetite | 56 (10.9%) | 45 (8.8%) |
| Dehydration | 22 (4.3%) | 9 (1.8%) |
| Back pain | 28 (5.4%) | 15 (2.9%) |
| Hypokalaemia | 18 (3.5%) | 9 (1.8%) |
| Hypomagnesaemia | 5 (1.0%) | 10 (2.0%) |
| Hyponatraemia | 5 (1.0%) | 13 (2.5%) |
| Headache | 33 (6.4%) | 41 (8.0%) |
| Paraesthesia | 17 (3.3%) | 3 (0.6%) |
| Peripheral sensory neuropathy | 13 (2.5%) | 25 (4.9%) |
| Dyspnoea | 23 (4.5%) | 44 (8.6%) |
| Anxiety | 5 (1.0%) | 11 (2.1%) |
| Alopecia | 69 (13.4%) | 73 (14.3%) |
| Epistaxis | 14 (2.7%) | 5 (1.0%) |
| Haemoptysis | 25 (4.9%) | 13 (2.5%) |
| Hiccups | 2 (0.4%) | 10 (2.0%) |
| Rash | 4 (0.8%) | 12 (2.3%) |
| Deep vein thrombosis | 17 (3.3%) | 5 (1.0%) |

Conclusion: In a pooled analysis of 1027 older men, postmenopausal women, and older patients with advanced cancer or SUI, Formula IX was well tolerated with an AE profile comparable to the control patients. Notably, there was no increase in gastrointestinal side effects with Formula IX compared to placebo treatment. Despite a higher proportion of subjects having elevated alanine aminotransferase (ALT) levels, these elevations were mild (grade 1/2) and transient with no evidence of drug induced liver injury by Hy's Law observed. Cardiovascular adverse event rates were similar between the two groups (less than 2%). The incidence of deep vein thrombosis was higher (3.30%) in the placebo group compared to the Formula IX group (1.0% o).

Example 5

Potential to Optimize Weight Loss with Formula IX: Meta-Analysis of Body Composition from Three Randomized Clinical Trials Support the Ability of Formula IX to Preserve Muscle while Reducing Fat A meta-analysis was conducted of three randomized clinical studies of Formula IX involving older men, postmenopausal women, and older patients who have muscle loss due to advanced cancer, to evaluate the ability of Formula IX to preserve muscle while reducing fat.

Methods: Meta-analysis was conducted of 3 randomized clinical trials evaluating Formula IX 3 mg every day versus placebo and who had a Day 84 dual-energy X-ray absorptiometry (DXA) scan to assess body composition: Phase 2 '501 study in older males (≥60 year old) and postmenopausal women (n=24 placebo and n=24 Formula IX), Phase 2 '502 study in patients with muscle wasting because of advanced cancer (n=30 placebo and n=31 Formula IX), and Phase 3 '504 study in patients with advanced lung cancer (n=135 placebo and n=124 Formula IX).

Figure 2A:
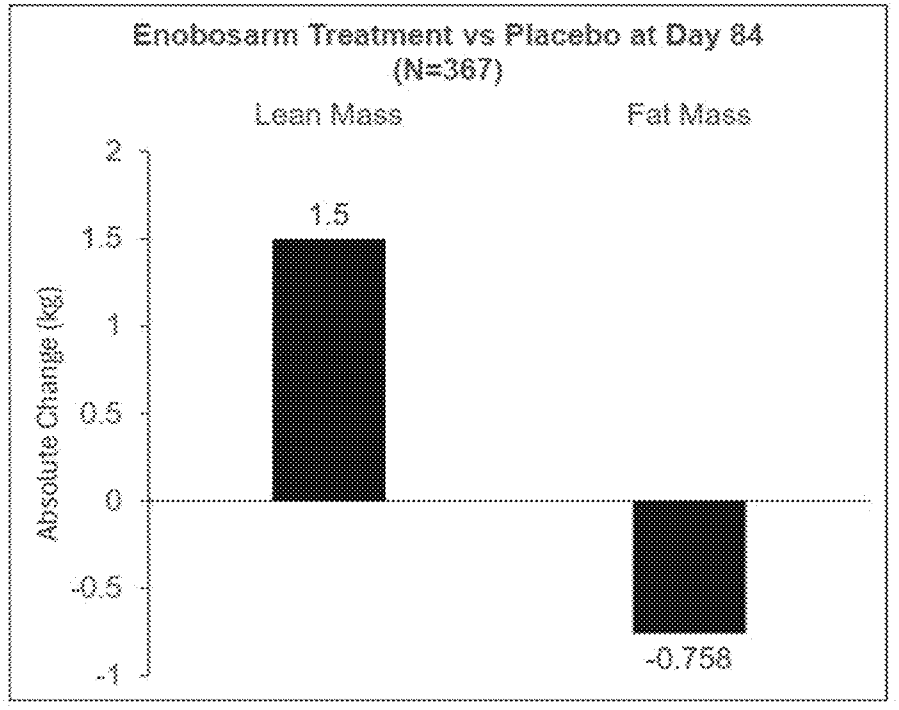
FIGS. 2A and 2B depict an absolute increase in lean mass of 1.5 kg in enobosarm (Formula IX) treated vs placebo (p=0.00004) (FIG. 2A) and a relative % change in lean mass of 4.04% in Formula IX vs placebo (p=0.00007) (FIG. 2B).
Figure 2B:
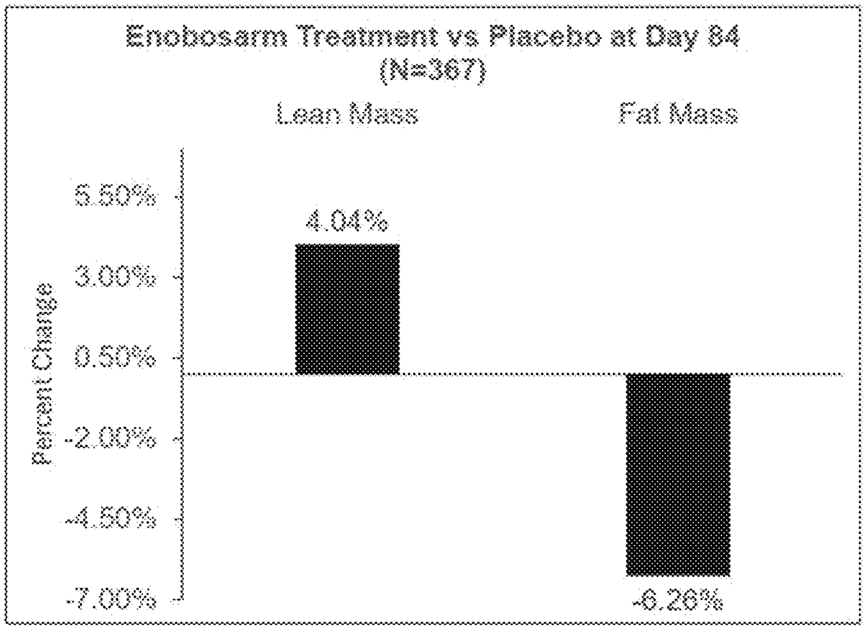

Results: At Day 84, DXA scans showed an absolute increase in lean mass of 1.5 kg in Formula IX treated vs placebo (p=0.00004), and a relative % change in lean mass of 4.04% in Formula IX vs placebo (p=0.00007) (FIGS. 2A and 2B). Absolute decrease in fat mass was 0.758 kg in Formula IX treated vs placebo (p=0.015), and % change in fat mass was −6.26% in Formula IX vs placebo (p=0.006), or a relative loss in fat mass with Formula IX. Formula IX was generally well tolerated with no increase in frequency of gastrointestinal side effects compared to placebo.

Conclusion: In meta-analysis of 367 older men, post-menopausal women, and older patients with muscle loss from advanced cancer, Formula IX therapy resulted in reductions in fat mass while preserving lean mass. This meta-analysis supports the potential of Formula IX when combined with a GLP-1 RA to preserve muscle, while preferentially reducing fat to potentially result in a higher quality weight loss in overweight and obese patients.

Example 6

Phase 2 Dose-Finding and Proof-of-Concept Study (QUALITY) to Evaluate the Effect on Body Composition & Safety of Formula IX in Patients Treated with GLP-1 RA for Quality Weight Loss The primary objective of this study was to assess the effect of Formula IX on total lean mass as measured by DXA in patients receiving GLP-1 receptor agonists. Secondary objectives/endpoints of this study were to assess the effect of Formula IX on: 1) total fat mass as measured by DXA; 2) total body weight as measured by scale and DXA; and 3) physical function (stair climb test). The tertiary/exploratory objective/endpoint of this study was to assess: 1) the correlation of change in total lean body mass and physical function at Day 112 and Day 196; and 2) the effect of Formula IX on waist circumference. The safety objective was to assess the safety and tolerability of Formula IX in patients maintained on GLP-1 receptor agonists.

This study was a multicenter, randomized, double-blind, placebo-controlled, dose-assessing study. Subjects were randomized to the three treatment arms in a 1:1:1 fashion. GLP-1 receptor agonist plus either: 1) Formula IX 3 mg dose group; 2) Formula IX 6 mg dose group; or 3) placebo group. All patients randomized into this study were medically indicated for use of GLP-1 receptor agonist for weight management. The first dose of GLP-1 receptor agonist was Day 1 of this study.

The primary efficacy endpoint of the study was the change from baseline in total lean mass at 4 months (112 days; topline discussed in Example 7). Subjects continued Formula IX (or matching placebo) monotherapy treatment from Day 112 to Day 196 (i.e., GLP-1 RA discontinued; discussed in Example 8) to assess the effect of Formula IX on total lean mass, total muscle mass, maintenance of weight loss, and rebound fat gain after discontinuation of GLP-1 receptor agonists. A safety follow-up visit occurred approximately 30 days after last dose of study drug. The safety of Formula IX compared to the placebo control was evaluated by an Independent Data Monitoring Committee (IDMC).

A total of approximately 168 subjects from fourteen clinical sites in the US were randomized in a 1:1:1 fashion to three treatment arms all receiving the GLP-1 receptor agonist, Wegovy® (semaglutide)] for weight reduction. Specifically, approximately 55 subjects were dosed for 112 days with GLP-1 receptor agonist plus Formula IX 6 mg once daily (Formula IX 6 mg Group or E6G), approximately 55 subjects were dosed with GLP-1 receptor agonist plus Formula IX 3 mg once daily (Formula IX 3 mg Group or E3G), and approximately 55 subjects were dosed with GLP-1 receptor agonist plus matching placebo once daily (Placebo Group or PG). The study population baseline characteristics included 31% males and 69% females; for age, 80% were between 60 and 70 years of age, 13% between 71-75 years of age, and 7% >75 years of age; and, for BMI, 14% were <30, 46% were between 30-34.9, and 40% were ≥35. The population consisted of 48% were non-whites and 52% whites. The dropout rate for the clinical study was 13%. After Day 112, the GLP-1 receptor agonist was stopped and the subjects continued to be dosed with Formula IX 3 mg, Formula IX 6 mg, or matching placebo monotherapy once daily from Day 112 to Day 196. The treatment randomization was maintained from Day 1 through Day 196. All subjects in the study received GLP-1 receptor agonist for 112 days per the approved prescribing information.

Randomization was stratified by gender such that each treatment group has approximately the same number of males and the same number of females. NOTE: There was no target number of males or females required in enrollment. However, the target for recruitment was that at least 30% of randomized subjects were of each gender.

Potential study participants underwent a series of screening evaluations including collection of demographic information, vital signs including weight, height, body mass index (BMI), blood pressure, pulse, temperature, medical history, physical exam, other concomitant medications, and 12-lead electrocardiogram (ECG) within 30 days prior to randomization, per FIG. 3 (see column labeled 'Screen'). Subjects who gave written informed consent and satisfied the selection criteria were enrolled into the study. Randomized subjects returned to the clinical study site every 28 days (FIG. 3). Dual-energy x-ray absorptiometry (DXA, total body composition, including lean mass, fat mass, and total mass) assessments were done at baseline (within 10 days prior to first dose of study drug), at Day 112 (for total lean mass and total fat mass assessments), and at Day 196 (for total lean mass, and total fat mass assessment), per FIG. 3. An assessment was performed at the end-of-study visit if the subject discontinued the study prior to Day 196. Physical function (performance) assessments (stair climb) were assessed at baseline (within 7 days prior to first dose of study drug), at Day 112, and at Day 196. An assessment was performed at the end-of-study visit if the subject discontinued the study prior to Day 196. Waist circumference was assessed at baseline (Day 1), at Day 112, and at Day 196. An assessment was performed at the end-of-study visit if the subject discontinued the study prior to Day 196.

Safety evaluations were the following: Vital signs (temperature/pulse/blood pressure [supine position, if possible]), body weight, and physical examination were assessed at baseline, and every 28 days while on study. An assessment was performed at the end-of-study visit if the subject discontinued the study prior to Day 196. Assessment of adverse events and a record of concomitant medications and non-medication therapies occurred at every study visit. A 12-lead electrocardiogram (single) occurred at baseline and end-of-study. If the subject completed the study through Day 196, additional required End-of-Study visit assessments might be completed on the same day.

Study Rationale: Formula IX has extensive clinical experience with at least 27 clinical trials conducted under sponsor-initiated INDs submitted to FDA with approximately 1,581 subjects being dosed with Formula IX. Among these studies, Formula IX has extensive clinical experience as a muscle targeting drug as it has shown benefit in five clinical studies in a total of 968 older subjects with and without muscle wasting. The results of these studies are summarized in Table 1 above (see Example 1). In these studies, Formula IX has been shown to increase total lean mass, decrease total fat mass, and increase physical function. Given the extensive clinical experience with Formula IX in both older patients and in patients with initial and ongoing muscle wasting caused by a starvation state (cancer induced muscle wasting), the combination of Formula IX with a GLP-1 receptor agonist for weight loss or diabetes may provide additional clinical benefit and ameliorate adverse muscle wasting effects of GLP-1 receptor agonist agents alone. Specifically, Formula IX therapy could augment the preferential loss of fat mass while preventing the loss of critical muscle mass. Formula IX treatment could also preserve or improve muscle strength and physical function in a subject that has prediabetes, diabetes mellitus, or does not have diabetes. Formula IX treatment could also preserve or improve muscle strength and physical function in older obese or overweight adults who dropped their muscle mass to critically low levels while being treated with a weight loss GLP-1 receptor agonist drug. It has become apparent that the total body weight loss caused by weight loss GLP-1 receptor agonist drugs is the result of not only the loss of fat, but also the loss of significant amounts of muscle. This muscle wasting adverse effect of GLP-1 drugs places elderly overweight or obese patients with sarcopenic obesity at risk as they already have low muscle mass and may develop muscle weakness, functional limitations, mobility disability, and be at higher risk for falls. The sponsor conducted this Phase 2 multicenter, double-blind, placebo-controlled, randomized (1:1:1), and dose-finding clinical study in approximately 150 obese or overweight patients who qualify for treatment with a GLP-1 receptor agonist, semaglutide injection, for subcutaneous use for chronic weight management and are at risk for loss of lean mass which leads to adverse body composition change.

The primary analyses on the primary, secondary, and exploratory endpoints were the change from baseline to Day 112 (FIG. 4). The comparisons were made between the randomized treatment groups. Additionally, to assess the effect of Formula IX monotherapy in patients that had discontinued GLP-1 RA treatment, patients continued Formula IX 3 mg, 6 mg, or matching placebo from Day 112 to Day 196 with discontinuation of the GLP-1 RA at Day 112. In this analysis, the primary, secondary, and exploratory endpoints from Day 112 to Day 196 and from Day 1 to Day 196 were assessed. The goal of these analyses was to assess the maintenance of body composition, body weight, and physical function when the GLP-1 RA was stopped and Formula IX was continued. These assessments were compared between the treatment groups. The overall goal of these assessments was to determine if Formula IX could maintain or improve body composition, overall body weight, and physical function in subjects that had discontinued GLP-1 RA. The flow diagram of the study design is as depicted in FIG. 4 where Formula IX is labeled Enobosarm.

Study Drug Administration: GLP-1 RA: The GLP-1 RA, semaglutide, was administered according to the approved prescribing information. The summary below is adapted from the approved prescribing information for Wegovy® (2022 Novo Nordisk). Initiated semaglutide with a dosage of 0.25 mg was injected subcutaneously once-weekly. Then the dose escalation schedule presented below was followed to minimize gastrointestinal adverse reactions.

Recommended Dosage Regimen for Adults

| Treatment | Weeks | Once weekly Subcutaneous Dosage |
|---|---|---|
| Initiation | 1 through 4 | 0.25 mg[a] |
| Escalation | 5 through 8 | 0.5 mg[a] |
| | 9 through 12 | 1 mg[a] |
| | 13 through 16 | 1.7 mg |

[a]Dosages not approved as maintenance for chronic weight management.

If patients did not tolerate a dose during dosage escalation, delaying dosage escalation for 4 weeks was considered. If the patient experienced intolerable gastrointestinal side effect associated with semaglutide treatment, the subject was advised to consider eating smaller meals and short-term use of over-the-counter antiemetic and/or antidiarrheal medications.

Doses and dose escalation of the GLP-1 receptor agonist were administered in compliance with approved label instructions for the product OR take as directed in the approved prescribing information. The first dose was administered under the supervision of the site staff. NOTE: In this study, based on the 16-week duration of the double blind portion of the study in which semaglutide was administered, the dose escalation was only up to 1.7 mg once-weekly dose of semaglutide.

Study Drug Administration: Formula IX or Matching Placebo: Formula IX 3 mg, 6 mg, and matching placebo were taken by mouth with 8 ounces of liquid (non-alcoholic) at approximately the same time every day. Since the effect of food on this formulation of Formula IX had not been assessed, the dose of Formula IX was taken at least 1 hour before or after a meal.

Study Duration: Subjects underwent screening for the study within 30 days prior to dosing with study drug with dosing starting on Day 1 of the study. Subjects received study drug for 196 days. A follow-up visit for safety assessment was conducted 30 days after the last dose of study drug. The total duration of the study for a subject in the study from screening to follow-up visit was up to 256 days (up to 30 prior to Day 1, 196 days of dosing, 30-day safety follow-up).

Efficacy Endpoints:

Primary Endpoint: The primary endpoint for the study was the percent change from baseline in total lean body mass at 112 days.

Secondary Endpoints: The secondary objectives or endpoints of this study were:

1. Percent change from baseline in total body fat to Day 112 (also at Day 196).
2. Percent change from baseline in stair climb to Day 112 (also to Day 196).
3. Percent change from baseline in total body weight to Day 112 (also to Day 196).
4. Proportion of patients that showed ≥0% increase in total lean mass, ≥10% increase in total lean mass, ≥15% increase in total lean mass, and ≥20% increase in total lean mass at Day 112 (also at Day 196).
5. Proportion of patients that showed ≥5% decrease in total body weight, ≥10% decrease in total body weight, and ≥15% decrease in total body weight at Day 112 (also at Day 196).
6. Proportion of patients that showed ≥10% decrease in total fat mass, ≥15% decrease in total fat mass, and ≥20% decrease in total fat mass at Day 112 (also at Day 196).

7. Proportion of patients that showed ≥10% increase in stair climb power, ≥15% increase in stair climb power, and ≥20% increase in stair climb power at Day 112 (also at Day 196).
8. Percent change from Day 112 in total body weight to Day 196.
9. Percent change from Day 112 in total body fat to Day 196.
10. Percent change from Day 112 in total lean body mass to Day 196.
11. Percent change from Day 112 in stair climb to Day 196.

Tertiary or Exploratory Endpoints:

12. Correlation of total lean body mass and physical function at Day 112 and Day 196.
13. Change in waist circumference at Day 112 and Day 196.

Selection Criteria:

Inclusion Criteria: Subjects that were accepted for this study must have:

1. Provided informed consent from the subject or the subject's legally authorized representative
2. Were to communicate effectively with the study personnel
3. Aged ≥60 years
4. For Female Subjects
   Menopausal status
   Were postmenopausal as defined by either:
   - one year or more of amenorrhea
   - surgical menopause with bilateral oophorectomy For Male Subjects
   - Subject must have agreed to use acceptable methods of contraception:
   - If the study subject's partner could have become pregnant, acceptable methods of contraception were used from the time of the first administration of study medication until 30 days following administration of the last dose of study medication. Acceptable methods of contraception were as follows: surgical sterilization (vasectomy with documentation of azoospermia) and a barrier method {condom used with spermicidal foam/gel/film/cream/suppository}, the female partner used oral contraceptives (combination estrogen/progesterone pills), injectable progesterone or subdermal implants and a barrier method (condom used with spermicidal foam/gel/film/cream/suppository).
   - If female partner of a study subject had undergone documented tubal ligation (female sterilization), a barrier method (condom used with spermicidal foam/gel/film/cream/suppository) was also used.
   - If female partner of a study subject had undergone documented placement of an intrauterine device (IUD) or intrauterine system (IUS), a barrier method (condom with spermicidal foam/gel/film/cream/suppository) was also used.
   - Female partner was menopausal as defined above.
5. Documented evidence of obesity (BMI ≥30 or ≥27 with the presence of at least one weight-related comorbid condition (e.g., hypertension or dyslipidemia). NOTE—monogenic or syndrome obesity, and endocrine causes of obesity (such as untreated hypothyroidism or Cushing's syndrome, and obesity caused by medications that cause weight gain were excluded from the study).
6. Medically indicated for use of GLP-1 receptor agonist for weight management.
7. Consents to be treated with GLP-1 receptor agonist for up to 112 days under this protocol.
8. Subject was willing to comply with the requirements of the protocol through the end of the study.
9. The patient was able to swallow oral medications.
10. The patient was able to complete the physical function (stair climb) assessment.
11. Maximum weight at screening of 300 lbs as per DXA requirements.
12. Completed a valid obstructive sleep apnea (OSA) assessment.

Exclusion Criteria: Any of the following conditions were cause for exclusion from the study:

1. Known hypersensitivity or allergy to Formula IX or a GLP-1 receptor agonist
2. Estimated glomerular filtration rate (eGFR)<30 mL/min/1.73 $m^2$ as measured using the chronic kidney disease-epidemiology collaboration (CKD-EPI) calculation (patients with mild and moderate renal failure were not excluded from participation in this study)
3. Treatment with any investigational product within <5 half-lives for each individual investigational product OR within 30 days prior to randomization
4. Major surgery within 30 days prior to randomization
5. Planned major surgery during the course of the study
6. Testosterone, methyltestosterone, oxandrolone (Oxandrin®), oxymetholone, danazol, fluoxymesterone (Halotestin®), testosterone-like agents (such as dehydroepiandrosterone, androstenedione, and other androgenic compounds, including herbals), myostatin inhibitors, apelin receptor agonists, or antiandrogens (flutamide, bicalutamide, abiraterone, enzalutamide, apalutamide, or darolutamide). Previous therapy with testosterone and testosterone-like agents was acceptable with a 30-day washout (if previous testosterone therapy was long term depot within the past 6 months, the site should contact the Medical Monitor) or any other androgenic agent.
7. An abnormal ECG result which, based on the investigator's clinical judgment, placed the subject at increased medical risk
8. Concurrently participating in any other interventional or treatment clinical trial.
9. Pre-existing liver disease (hepatitis B, uncontrolled hepatitis A, hepatitis C, autoimmune hepatitis, liver cancer, alcohol-associated cirrhosis, alcohol-associated hepatitis, alcohol-associated fatty liver).
10. Baseline ALT or AST >3× upper limit of normal.
11. Baseline total bilirubin levels >upper limit of normal.
12. History of acute pancreatitis within one year of screening or history of chronic pancreatitis.
13. Severe gastrointestinal disease, including gastroparesis.
14. Major depressive disorder diagnosed within 2 years prior to screening (NOTE: a diagnosis of major depressive disorder >2 years prior to screening that was stably managed [with or without pharmacological intervention] without additional exclusionary history were not excluded from the study), history of other severe psychiatric disorder, including schizophrenia and bipolar disorder, any lifetime history of suicide attempt, or with suicidal ideation or behavior within 1 month prior to screening.
15. Patient Health Questionnaire score >15 or any suicidal ideation of type 4 or type 5 on the Columbia-Suicide Severity Rating Scale.

16. Monogenic or syndrome obesity, and endocrine causes of obesity (such as untreated hypothyroidism or Cushing's syndrome), and obesity caused by medications that cause weight gain.
17. Prior bariatric surgery or weight loss devices unless removed for ≥1 year prior to screening for this study.
18. Patients that were currently taking a GLP-1 receptor agonist or have taken a GLP-1 receptor agonist within one year prior to screening for this study. Patients were not allowed to resume treatment with GLP-1 receptor agonists until after the 30-day follow-up visit.
19. Diagnosis of diabetes that required current use of any antidiabetic drug or HbA1c >
6.5% Note: Metabolic syndrome was not an exclusion, even if managed with an antidiabetic drug such as metformin or an SGLT2 inhibitor. A diagnosis of prediabetes or impaired glucose tolerance managed with antidiabetic medication or non-pharmacologic approaches (e.g., diet and exercise) was not an exclusion as long as other study criteria were met and the patient had not progressed to a diagnosis of diabetes.
20. Creatine kinase >ULN (upper limits of normal).
21. Any condition that was exclusionary for use of semaglutide (generally WEGOVY) in the patient. See the WEGOVY Prescribing Information. The following contraindications were listed in the WEGOVY prescribing information:
    a. Personal or family history of medullary thyroid carcinoma or in patients with Multiple Endocrine Neoplasia syndrome type 2.
    b. Known hypersensitivity to semaglutide or any of the excipients in WEGOVY.
22. Subjects with active or untreated malignancy within 5 years of screening (NOTE: treated non-melanoma skin cancers were allowable).
23. Male subjects with a lifetime history of malignant prostate disease, such as prostate cancer.
24. Male subjects with a PSA ≥4 ng/mL.
25. Patients with prior tendon rupture or those taking concomitant medications that increased the risk of tendon rupture (e.g., fluoroquinoline antibiotics, bempedoic acid, or corticosteroids).
26. Uncontrolled hypertension (systolic blood pressure ≥160 mmHg and/or diastolic blood pressure ≥100 mmHg).
27. Patients with a resting heart rate ≥100 beats per minute.

Assessment Description: Obstructive Sleep Apnea (OSA) Assessment: Obesity is a major risk factor for Obstructive Sleep Apnea (OSA). A sleep study was conducted at screening to determine whether patients had OSA. For those patients that were determined to have sleep apnea at screening either by study testing or prior diagnosis no matter the current treatment, additional sleep studies was performed at Screening (considered as baseline for this assessment), Day 112, and Day 196/End of Study. If patients had been diagnosed with sleep apnea, the OSA assessment was done while using the current treatment as prescribed for sleep apnea. A new diagnosis after Baseline or worsening of OSA was reported as an Adverse Event of Special Interest (AESI).

OSA was evaluated using an at Home Sleep Apnea Test (HSAT) that measured Apnea-Hypopnea Index (AHI) and Respiratory Disturbance Index (RDI). AHI was the number of apneas and hypopneas that occur per hour of sleep. RDI was the number of apneas and hypopneas plus Respiratory effort-related arrousals (RERAs) that occurred per hour of sleep. Diagnosis of OSA was based on the following parameters: AHI of <5/hour was normal, whereas AHI of 5-14.9/hour, 15-29.9/hour, or ≥30/hour was mild, moderate or severe OSA; or RDI ≥10 when AHI was normal. Moderate or Severe OSA should always be treated due to increased risk of other comorbidities. Patients diagnosed with OSA at Screening were referred to their physician for evaluation and follow-up.

Questionnaire Response Reporting (C-SSRS and PHQ-9): Columbia Suicidality Severity Rating Scale (C-SSRS): A suicide risk assessment was performed using the C-SSRS. This scale was administered by the Investigator or designee, completed on-site, and was on paper. The "Screening/Baseline" version of the C-SSRS questionnaire was used at the Screening Visit to assess any lifetime suicidal ideation and to assess for any suicidal ideation for one month prior to screening. The "since last visit" C-SSRS questionnaire was used for Baseline/Day 0 through End of Study. For any type 4 or 5 ideation or suicidal behavior or if the Investigator determines that a participant was at risk of suicide or self-harm, he/she was immediately discontinued from the study and appropriate measures to ensure the participant's safety and mental health evaluation were implemented. The event was recorded as either an AE or a SAE, as determined by the Investigator, and reported to the Sponsor within 24 hours.

Patient Health Questionnaire (PHQ-9): A depression assessment was performed using the PHQ-9. The questionnaire was completed independently by the participant at each visit, Screening through End of Study. A participant should be referred to a mental health professional (MHP) if they had the below scores at screening or any time through the end of the study: 1) A PHQ-9 score ≥15; 2) Any suicidal behavior; 3) Any suicidal ideation of type 4 or 5 on the C-SSRS; or 4) If in the opinion of the Investigator it was necessary for the safety of the participant. The event should be recorded as either an AE or a SAE, as determined by the Investigator, and reported to the Sponsor within 24 hours. For PHQ-9, if a participant's psychiatric disorder was adequately treated with psychotherapy and/or pharmacotherapy, then the patient, at the discretion of the MHP, remained in the study.

Physical Performance (physical function): Physical function was assessed at baseline, Day 112, Day 196, and end of study visit (if subject discontinued prior to Day 196).

Physical function test: Stair climb test:

BASELINE: The subject was weighed at baseline. 10% of the body weight was calculated. This weight (10% of the total scale body weight rounded to the nearest multiple of 5) was added in a backpack or through ankle weights. This weight (10% of total body scale weight at Baseline rounded to the nearest multiple of 5) was added to the patient load at each assessment day (Baseline, Day 112, Day 196, and end of study visit [if subject discontinued prior to Day 196]).

The subject was asked to climb 8 steps, one step at a time as quickly as possible without running. The subject was asked to only use the handrail in the event that the subject felt like they were losing their balance. Study personnel was NOT to give the subject any encouragement during the test. For the safety of the subject, a single individual or multiple individuals were assigned by the site to follow the subject up the stairs to assure that the subject did not lose their balance and fell backward down the steps. This study assigned person (s) were sufficient in strength, size and agility to protect the subject and themselves from falling. The study assigned person were not to push the subject up the stairs by following too close, but were to be close enough to maintain the balance in the event it was needed.

The height of the stairs from the surface of the base of the first step to the surface of the eighth step was recorded.

The scale weight of the subject at the time of the stair climb assessment+the load added (10% of total body scale weight at Baseline rounded to the nearest multiple of 5) was taken. This weight included the shoes and clothes that the subject was wearing at the time of the stair climb assessment and the additional weight added.

The time from the first foot to contact the base below the first step (timer started) to the first foot contact the surface of the eighth step (timer stopped) was measured.

NOTE: If a subject was unable to climb all eight steps or if a subject was unable to climb the eight steps in less than 60 seconds, then the time for this subject was assigned as 60 seconds.

Adverse Events: An adverse event (AE) was any unfavorable or unintended change in body structure (signs) or body function (symptoms), abnormal laboratory result that was associated with symptoms or requires treatment or worsening of a pre-existing condition. This included all such events regardless of the presumed relationship between the event and the study medication(s). Any AE that occurred after the informed consent was signed but prior to dosing on Day 1 was captured and was documented on the AE eCRF. This included AEs resulting from concurrent illnesses, reactions to concomitant medications or progressive disease states. These AEs were also captured as part of the medical history. Each subject was assessed for the development of any adverse events. Adverse events were to be assessed at each visit to the clinic. This information was obtained in the form of non-leading questions (e.g., "How are you feeling?") and from signs and symptoms detected during each examination, observations of the study personnel or spontaneous reports from the subjects. Any AEs such as complaints, signs, or symptoms that occurred during the course of the study or designated follow-up periods were recorded on the subject's case report form (eCRF). This included AEs resulting from concurrent illnesses, reactions to concomitant medications, or progressive disease states. Whenever possible, the AE was described on the case report form using standard medical terminology consistent with the Medical Dictionary for Regulatory Activities (MedDRA) in order to avoid the use of vague, ambiguous or colloquial expressions. The investigator evaluated all adverse events as to their intensity, relation to test medication, outcome and action taken. Each AE was evaluated for duration, intensity, and relationship to (or association with) the study treatment (or other causes). Additionally, the actions taken (e.g., reduction of dosage, discontinuation of study medication, administration of treatment, etc.) and the resulting outcome of the AE were indicated on the case report form. Any subject who was withdrawn from the study due to an adverse event was followed until the outcome of the event was determined, and the investigator prepared a written summary of the event and documented the available follow-up information on the case report form.

Adverse Events of Special Interest: An Adverse Event of Special Interest (AESI) was an event of scientific and medical concern specific to the study drug(s), for which rapid communication and ongoing monitoring were warranted. The AESIs in this protocol, regardless of attribution, expectedness, or severity were: 1) ALT increased; 2) AST increased; 3) Total bilirubin increased; 4) New diagnosis or worsening of obstructive sleep apnea; 5) Prostate related events; or 6) Testicular related events. AESIs were collected from the time of first study drug administration through 30 days after last dose of study drug. AESIs of clinical interest must have been reported to Worldwide Clinical Trials Drug Safety within 24 hours of the knowledge of the occurrence. Any AESI which occurred during the study or within 30 days following last dose of study medication, whether or not related to the study medication, must have been reported immediately via eCRF (within 24 hours) to Worldwide Clinical Trials Drug Safety (see contact information below). If the eCRF was unavailable, a paper form should have been submitted via fax or email. As applicable, and per IRB guidelines, the investigator would promptly notify the Institutional Review Board (IRB).

Summary of Safety of semaglutide injection, for subcutaneous use: The summary of safety of semaglutide injection SQ was available in the WEGOVY® prescribing information.

Intensity of Adverse Events: The intensity of the AEs was graded on a scale of 1 to 5, with 1 being mild and 5 being death, according to MedDRA. If the intensity (Grade) changed within a day, the maximum intensity (Grade) was recorded. If the intensity (Grade) changed over a longer period of time, the changes were recorded as separate events (having separate onset and stop dates for each grade).

Test Medication Causality: The relationship (or association) of each AE to the test medication was assessed by the investigator according to the following definitions:

Unrelated: There was no chance that the study medication caused the AE; other conditions, including concurrent illnesses, progression or expression of the disease state, or a reaction to a concomitant medication best explained the event.

Unlikely: There was little chance that the study medication caused the AE; other conditions, including concurrent illnesses, progression or expression of the disease state, or a reaction to a concomitant medication best explain the event.

Possible: The association of the AE with the study medication was unknown; however, the AE was not clearly due to another condition.

Probable: A reasonable temporal association existed between the AE and treatment administration and, based on the investigator's clinical experience, the association of the AE with the study treatment seemed likely.

Definite: The association of the AE with the study medication had a direct relationship. For the purpose of safety analyses, all AEs which were classified as "Possible," "Probable" or "Definite" were considered treatment-related events.

Serious Adverse Events: A serious adverse event (SAE) was defined as any experience that suggested a significant clinical hazard, contraindication, side effect, or precaution. This included any event which: 1) Resulted in death; 2) Was life-threatening; 3) Required inpatient hospitalization or caused prolongation of existing hospitalization; 4) Resulted in persistent or significant disability/incapacity; 5) Resulted in congenital abnormality/birth defect; or 6) Required intervention to prevent permanent impairment or damage.

An SAE also might include other events, based on medical judgment, which jeopardized the subject and required medical or surgical intervention to prevent one of the outcomes listed above. Any SAE, including death due to any cause, which occurred during the study or within 30 days following last dose of study medication, whether or not related to the study medication, must have been reported immediately via eCRF (within 24 hours) to Worldwide Clinical Trials Drug Safety (see contact information below). If the eCRF was unavailable, a paper form should have been submitted via fax or email.

STATISTICAL ANALYSIS: Sample Size Calculation: The following parameters were used to determine the sample size of this study: 1) $\alpha=0.05$ (two-sided); 2) Power=90%; 3) Subjects in the placebo group were expected to lose 1.6 kg of total lean mass over a 112 days or 3.4 kg of total lean mass over a 112 days (depending on the assumptions and calculation used based on available data with semaglutide monotherapy); 4) Subjects in the Formula IX 6 mg dose group were expected to lose 0.3 kg of total lean mass over a 112 day treatment period (maintenance of lean mass); 5) Assumed a standard deviation of the outcome in the population of 2.0 kg if you assumed the 1.6 kg loss of total lean mass in the control group and 4.8 kg if you assumed the 3.4 kg loss in lean mass in the control group. Based on the parameters outlined above, a sample size of 50 subjects per treatment arm were required. Therefore, sponsor planned to enroll approximately 50 subjects in each of the three treatment arms of this study to account for variability and to generate hypotheses to design additional clinical studies.

Justification of Expected Lean Mass Changes: A subgroup analysis of the STEP 1 study of semaglutide showed a 6.92 kg reduction in lean mass over a 68 week treatment period (Wilding J P H et al. Once-weekly semaglutide in adults with overweight or obesity. NEJM 384: 989-1002, 2021.). In this study, approximately 50% of the total body weight loss occurred up to approximately 16 weeks of treatment. 1) If it is assumed that the lean mass loss is a linear function of time (which is a conservative estimate since body weight loss is greater in the first 6 months and it is likely that muscle loss tracks body weight loss), these patients are expected to lose 0.102 kg per week. The V2000101 study has a 16-week follow up period. Therefore, based on this calculation it is expected that the control group will lose approximately 1.63 kg of lean mass during the course of this study. 2) If it is assumed that the timeline and amount of lean mass loss corresponds to total body weight loss, then approximately 50% of the lean mass loss is expected to be experienced in the 16 weeks after initiation of treatment with semaglutide. Therefore, based on this calculation, it is expected that the control group will lose approximately 3.4 kg of total body lean mass during the course of this study.

In obese patients ≥60 years of age with non-small cell lung cancer, without changes in exercise or diet, Formula IX 3 mg treatment for 84 days showed a 0.3 kg decrease in total lean mass from baseline (Study G300504, data on file). In this study, the placebo control group showed a decrease of over 3 kg in total lean mass. This indicates that Formula IX can maintain total lean mass in patients that are experiencing reduction in total body weight and the accompanying loss of lean mass.

Populations: The Intent-to-Treat (ITT) population was all randomized subjects; the Modified Intent-to-treat (MITT) population was all randomized subjects who had taken at least one dose of study drug; and the Safety Population (SAF) was all randomized subjects who had taken at least one dose of study drug.

Efficacy Analyses: Primary Endpoint: The primary endpoint was the percent change from baseline in total lean body mass from baseline to Day 112. The primary endpoint was analyzed for the ITT population. The changes from baseline to Day 112 were summarized for the total lean body mass. The analysis to statistically compare the treatment groups for the percent changes from baseline to Day 112 (and also baseline to Day 196, and Day 112 to Day 196) was done using a repeated measures analysis with treatment as a factor and covariates of study site and baseline total lean body mass. This analysis compared percent change from baseline to Day 112 in the following observational and statistical comparisons: 1) E6G vs. PG; 2) E3G vs. PG; and 3) E6G vs. E3G. The analysis was conducted after the last patient completed Day 112 DXA assessment (or had discontinued from the study prior to Day 112). A similar analysis of absolute change from baseline was also conducted.

Secondary Analyses: Secondary Endpoints: All secondary endpoints were analyzed comparing the following groups: 1) E6G vs. PG; 2) E3G vs. PG; and 3) E6G vs. E3G. The primary analyses for all of these endpoints were change from baseline to Day 112. Additionally, information gathering analyses were conducted on these endpoints from Day 112 to Day 196 and from Day 1 to Day 196. The goal of these analyses was to assess the maintenance of body composition, body weight, and physical function when the GLP-1 RA was stopped and Formula IX was continued. These assessments were baseline controlled.

Change (% change) from Baseline in Total Body Fat Mass: This analysis was conducted in same manner as the primary endpoint. The comparisons were done for baseline to Day 112, baseline to Day 196, and Day 112 to Day 196. The primary analysis was from baseline to Day 112 for total body fat mass.

Change (% change) from Baseline in physical function: Physical function was assessed by stair climb. This analysis was conducted in the same manner as the primary endpoint. The comparisons were done for baseline to Day 112, baseline to Day 196, and Day 112 to Day 196. The primary analysis was at Day 112 for physical function.

Change (% change) from Baseline in Total Body Weight: This analysis was conducted in the same manner as the primary endpoint. Total body weight was analyzed on scale weight collected at baseline, Day 112, and Day 196, and DXA total body weight at baseline, Day 112, and Day 196. The comparisons were done for baseline to Day 112, baseline to Day 196, and Day 112 to Day 196. The primary analysis was from baseline to Day 112 for total body weight.

Responder Analysis: The proportion of patients that showed: 1) ≥0%, ≥10%, ≥15%, and ≥20% increase in total lean mass in each treatment group were assessed; 2) The proportion of patients that showed ≥10%, ≥15%, and ≥20% decrease in total fat mass in each group were assessed; 3) The proportion of patients that showed ≥5%, ≥10%, and ≥15% decrease in total body weight in each group were assessed; 4) The proportion of patients that showed a ≥10%, ≥15%, and ≥20% increase in stair climb power in each group were assessed; and 5) The proportion of patients that showed a ≥10%, ≥15%, and ≥20% decrease in stair climb time in each group were assessed. The percentage of subjects that met these criteria in the treatment groups was summarized and compared observationally and statistically. The number and percentage of responders were summarized by treatment group. Responders were analyzed using a logistic regression model. This model included treatment as a factor and study site as a covariate. Odds ratios, standard errors, 95% confidence intervals and p-values for the treatment difference were presented. The analysis was performed on the ITT population.

Correlation of total lean mass to physical function (exploratory endpoint): The change from baseline to Day 112 and change from baseline to end of study in total lean mass as measured by DXA total body composition scan and physical function (stair climb power) were correlated. The goal of this analysis was to assess if increases in DXA total lean mass resulted in an increase in physical function. The physical function data from the Formula IX treated groups was analyzed by quartiles and median of total lean mass change from baseline. Additionally, the physical function data from all evaluable patients (Formula IX groups and placebo group) was analyzed by quartiles and median of total lean mass change from baseline.

Change (% change) from Baseline in Waist Circumference (exploratory endpoint): This analysis was conducted in same manner as the primary endpoint. Waist circumference was collected at baseline, Day 112, and Day 196. The comparisons were done for baseline to Day 112, baseline to Day 196, and Day 112 to Day 196. The primary analysis was from baseline to Day 112 for waist circumference.

Safety Analysis: The frequency of adverse events (AEs) was tabulated by MedDRA term and system organ class. The incidence of AEs and the maximum intensity and frequency of AEs were summarized. A new onset AE was defined as an AE that was not present prior to treatment with study medication but appeared following treatment or was present at treatment initiation and worsened during treatment. An AE that was present at treatment initiation but resolved and then reappeared while the subject was on treatment was a new-onset AE (regardless of the intensity of the AE when the treatment was initiated). All laboratory results, vital sign measurements, and other safety variables were summarized using appropriate descriptive statistics. Changes from baseline were computed and were summarized using appropriate descriptive statistics. An IDMC was established for this protocol and met to review unblinded safety data periodically throughout the conduct of the study. The timing and the content of this review were documented in the IDMC charter for this study.

Example 7

Preliminary (Topline) Efficacy Data Through Day 112 of the QUALITY Clinical Study The clinical trial protocol for the QUALITY Study was described in detail in Example 6 above. The primary endpoint of this study was to assess the effect at Day 112 of Formula IX on total lean mass (same as lean body mass or LBM herein throughout) as measured by DXA in patients receiving the GLP-1 receptor agonist (GLP-1 RA) semaglutide (WEGOVY) for weight reduction and additionally either 3 mg or 6 mg of Formula IX, or a placebo (randomized in a 1:1:1 ratio), as described in Example 6. Secondary objectives/endpoints of this study were to assess the effect of Formula IX on: 1) total fat mass (same as fat body mass or FBM herein throughout) as measured by DXA; 2) total body weight as measured by DXA; and 3) physical function (stair climb power test or SCP test). The purpose of the Phase 2b clinical trial was to select the optimal oral dose of Formula IX in combination with GLP-1 RA that best preserves lean body mass and augments the reduction in adiposity (fat body mass) to improve body composition at Day 112 (16 weeks) of treatment. The data tables below indicated that the primary endpoint and several of the secondary endpoints were met.

Baseline characteristics: Fourteen clinical sites in the United States participated in the study. 168 patients were randomized to oral daily doses of Formula IX 3 mg, Formula IX 6 mg, or placebo at the time they initiated WEGOVY (semaglutide) for weight reduction. The study population baseline characteristics included 31% males and 69% females; for age, 80% were between 60 and 70 years of age, 13% were between 71-75 years of age, and 7% were ≥75 years of age; and, for BMI, 14% were <30, 46% were between 30-34.9, and 40% were ≥35. Population included 48% non-whites and 52% whites. The dropout rate for the clinical study was 13%.

Primary endpoint of total lean mass measured by DXA was met: Preliminary (topline) data for the total lean mass demonstrated that the QUALITY study met its primary endpoint of decreasing the loss of lean mass for Formula IX groups with a statistically significant benefit in total lean mass compared to placebo. That is to say, Formula IX prevented the loss of lean mass due to semaglutide treatment. As expected, lean mass was reduced in the placebo (only received semaglutide) by a meaningful amount of −4.1% (mean) as shown in Table 4 below. This loss of lean mass due to semaglutide is a clinical representation of the component of total body weight loss that is from a loss of muscle. This obese (≥27 BMI with co-morbidities; or ≥30 BMI) and elderly (≥60 years old) population treated in the QUALITY study, as described in Example 6, were already predisposed to sarcopenia and weakness/frailty, a problem that is exasperated by further loss of muscle due to semaglutide treatment. In contrast, based on actual measured values ('measurable values' portion of Table 4), the patients receiving Formula IX together with semaglutide retained lean mass [0% lean mass loss for Formula IX 3 mg group; the p-value for this reduction is $p<0.001$ compared to placebo according to the least square (LS) mean measurements analysis ('statistical analysis' portion of Table 4)] or experienced less loss of lean mass [−2.6% for Formula IX 6 mg group or −1.2% for Formula IX all (pooled) group] than the aforementioned −4.1% for semaglutide only. This represents on average a 71% reduction of lean mass loss in all patients receiving Formula IX+semaglutide (−1.2±5.15%; N=100) versus placebo+semaglutide (−4.1±4.80%; N=47) at Day 112. The p-value for this reduction is $p=0.002$ according to the least square means analysis (Table 4). To put these changes in context, the median percentage of total body weight loss that is due to lean mass is 32% in the placebo+semaglutide group, 9.4% in the all Formula IX+semaglutide group, and 0.9% in the Formula IX 3 mg+semaglutide group. This clinical benefit from Formula IX represents a 97% reduction in the contribution of lean mass loss to the amount of total body weight loss in the Formula IX 3 mg+semaglutide group compared to placebo+semaglutide.

The muscle mass component of lean mass exerts healthy influence on glucose and fat metabolism. Lean mass also exerts healthy influence on tissues required for physical performance such as muscle and bone. The maintenance of lean mass with Formula IX was a beneficial change in body composition compared to placebo. Accordingly, Formula IX and SARMs of this invention may prevent the development of osteopenia or osteoporosis that leads to bone fractures, or sarcopenia due to reductions in skeletal muscle mass or bone mass or density that is associated with the use incretin agonists or antagonists, and other weight loss drugs.

TABLE 4

| Total Lean Mass (Primary Endpoint) | | | | |
|---|---|---|---|---|
| | Formula IX 3 mg | Formula IX 6 mg | Formula IX All | Placebo |
| N | 51 | 49 | 100 | 47 |
| (a) Measurable values: Mean % Change from Baseline Total Lean Mass | | | | |
| Total Lean Mass %, (mean ± SD), median | 0.0 ± 4.34% 0.1% | −2.6 ± 5.60% −1.5% | −1.2 ± 5.15% −0.8% | −4.1 ± 4.80% −5.2% |
| (b) Statistical Analysis | | | | |
| Total Lean Mass %, (LS mean ± SE), p-value | 0.21 ± 0.72% <0.001 | −2.65 ± 0.73% 0.190 | −1.22 ± 0.52% 0.002 | −3.99 ± 0.74% |

Observations:

The Quality study met the primary endpoint with a statistically significant benefit in total lean mass compared to placebo.

The placebo group showed a meaningful reduction in lean mass from baseline.

Topline Secondary Endpoints

Total Fat Mass: One of three secondary objectives was to retain or enhance total fat mass loss (as measured by DXA) achieved by semaglutide alone when semaglutide is co-administered with Formula IX. Formula IX+semaglutide treatment produced a dose dependent reduction in total fat mass at Day 112 compared to placebo+semaglutide. There was 27% greater fat mass loss in all Formula IX+semaglutide treated patients compared to placebo+semaglutide (mean total fat mass percent change from baseline for all Formula IX treated, −10.9±8.07%; n=99 versus placebo semaglutide treated subjects −8.6±6.26%; n=48, p=0.096 (Table 5)). The Formula IX 6 mg treated group had a statistically significant 48% greater fat mass loss compared to placebo or semaglutide alone (mean total fat mass percent change from baseline for 6 mg Formula IX+semaglutide treated subjects, −12.7±9.80%; n=49, versus placebo+semaglutide subjects, −8.6±6.26%; n=48, p=0.014 (Table 5)). There was a general observational trend of greater reduction of fat for Formula IX groups compared to the placebo in all the analyses, though the difference did not achieve statistical significance in all cases. Accordingly, the secondary endpoint of retaining fat reduction due to semaglutide was achieved in all cases; and, at least for the Formula IX 6 mg group, a statistically significant enhancement of fat reduction over semaglutide was achieved.

Individuals with a high body fat percentage are at a greater risk of cardiovascular diseases, type 2 diabetes, several types of cancer, and early mortality. The reduced adiposity of groups treated with Formula IX indicated the possibility of improving insulin resistance and/or heart disease, e.g., in cardiometabolic syndrome or diabetic patients needing to lose weight. Based on fat mass data alone, Formula IX allows the use of semaglutide without compromising, and possibly even enhancing, these health benefits. Further, coupled to the maintenance of lean mass discussed above, it appears that Formula IX and SARMs of this invention may prevent the development of sarcopenic obesity in patients taking incretin agonists or antagonists, or other weight loss drugs.

TABLE 5

| Total Fat Mass (Secondary Endpoint) | | | | |
|---|---|---|---|---|
| | Formula IX 3 mg | Formula IX 6 mg | Formula IX All | Placebo |
| N | 50 | 49 | 99 | 48 |
| (a) Measurable values: Mean % change from baseline-Total Fat Mass | | | | |
| Total Fat Mass, (mean ± SD), median | −9.1 ± 5.47% −9.6% | −12.7 ± 9.80% −12.3% | −10.9 ± 8.07% −10.8% | −8.6 ± 6.26% −8.4% |
| (b) Statistical Analysis: Mean % change from baseline-Total Fat Mass | | | | |
| Total Fat Mass, (LS mean ± SE), p-value | −8.96 ± 1.09% 0.687 | −12.10 ± 1.09% 0.014 | −10.53 ± 0.78% 0.096 | −8.36 ± 1.08% |

Observations:

Dose dependent reduction in fat mass was observed (Formula IX 6 mg had p=0.014).

Additional fat mass loss was observed in the Formula IX groups compared to placebo.

Total Weight Loss: Although Formula IX+semaglutide treatment compared to placebo+semaglutide alone improved changes in body composition by preservation of lean mass and greater fat mass loss, there were minor changes in total body weight between the Formula IX group and placebo group at Day 112 (16 weeks). Using DXA weights, the following changes were observed: Formula IX 3 mg treated (−4.2±3.30%; n=51), Formula IX 6 mg treated (−5.2±4.49%; n=49), all Formula IX treated (−4.6±3.94%; n=100), and placebo semaglutide alone (−4.9±4.67%; n=48) (Table 6). To provide context, the difference in absolute weight between all Formula IX treated subjects of −4.4 kg versus semaglutide alone −4.7 kg was just 0.3 kg in total body weight loss, corresponding to no meaningful difference in observed total body weight changes between the Formula IX groups and placebo group.

TABLE 6

| Total Body Weight (Secondary Endpoint) | | | | |
|---|---|---|---|---|
| | Formula IX 3 mg | Formula IX 6 mg | Formula IX All | Placebo |
| N | 51 | 49 | 100 | 48 |
| (a) Measurable values: Mean % Change from Baseline-Total Body Weight (DXA weight) | | | | |
| Total Body Weight (DEXA), mean ± SD, median | −4.2 ± 3.30%<br>−4.1% | −5.2 ± 4.49%<br>−4.5% | −4.63 ± 94%<br>−4.3% | −4.9 ± 4.67%<br>−4.6% |

Higher Quality Weight Loss: The composition of the weight loss is clearly different between the Formula IX group(s) and the placebo group. Although the total weight loss was not clinically meaningfully different, the composition of the total weight lost was improved. In the placebo group, 32% of the weight loss was lean mass loss (Table 7). In contrast, the Formula IX pooled group had only 9% of the weight loss was attributed to lean mass loss, and only 1% of the total body weight loss in the Formula IX 3 mg (Table 7). In overview, the mean total body weight loss was comparable across all groups, but Formula IX groups lost more fat mass and less lean mass, indicating a favorable overall effect on body composition.

In greater specifics, of the total weight lost at Day 112, the median loss of lean mass versus fat mass loss was 31.9% vs. 68.1% in the placebo semaglutide group, 9.4% vs. 90.6% in the all Formula IX treated group, and 0.9% vs. 99.1% in the Formula IX 3 mg group (Table 7). Formula IX improved changes in body composition and resulted in more selective and greater loss of adiposity than observed in subjects receiving placebo+semaglutide alone. Because of the selective loss of adiposity with Formula IX treatment, the expectation is that when patients are treated for a longer duration, there could be a greater reduction in fat mass than with placebo+semaglutide treatment alone.

TABLE 7

| Composition of Weight Loss | | | | |
|---|---|---|---|---|
| | Formula IX 3 mg | Formula IX 6 mg | Formula IX All | Placebo |
| (a) Percentage of Body Weight Loss due to Lean Mass and Fat Mass (estimated) | | | | |
| Median Lean Mass (calculated from measured values) | 0.9% | 16.6% | 9.4% | 31.9% |
| Fat mass (estimated) | 99.1% | 83.4% | 90.6% | 68.1% |

Physical Function Endpoint—Stair Climb Power (SCP): The last of the three secondary objectives was to prevent the loss of physical function associated with loss of lean mass in patients treated with incretin agonist and antagonist containing drugs such as semaglutide. Stair climb power (SCP) test, as described in Example 6, was used to assess the difference in physical function in patients receiving semaglutide compared to patients receiving both semaglutide and Formula IX. A decrease in physical function of a patient would be reflected as a decrease in SCP. The SCP test was a loaded 8 step stair climb test that was conducted at baseline and at Day 112. Climbing stairs is an activity of daily living, and the SCP test measures functional muscle strength, balance and agility. The improvement in body composition by preservation of lean mass is captured by measuring changes in physical function using the stair climb test.

More than half (51.1%) of the population in the placebo group lost at least 5% SCP during the study with a median value of −5.1%. In a responder analysis, the proportion of subjects that lost at least 5% and at least 10% SCP in the placebo group was statistically significantly higher than in the Formula IX groups (3 mg and all) (Table 8):

Stair Climb Test Power (Responder Analysis for the Proportion of Subjects that Lost at Least 10% of Stair Climb Power at 16 Weeks):

In the placebo+semaglutide group, 42.6% of the patients experienced at least a 10% reduction in stair climb power from baseline. Representing the first time a loss of physical function has been tested and observed with GLP-1 RA treatment.

In the all Formula IX+semaglutide group, a 54.4% reduction in proportion of patients with at least a 10% loss in stair climb power from baseline vs. placebo+semaglutide group (19.4% in the all Formula IX+semaglutide group vs. 42.6% in the placebo+semaglutide, p=0.0049).

In the Formula IX 3 mg+semaglutide group, there was a 62.4% reduction in proportion of patients that experience at least a 10% loss in SCP compared to placebo+semaglutide group (16.0% in the Formula IX 3 mg+semaglutide group vs. 42.6% in the placebo+semaglutide, p=0.0066).

In the Formula IX 6 mg+semaglutide group, there was a 46.2% reduction in the proportion of patients that experience at least a 10% reduction in stair climb power compared to placebo+semaglutide (22.9% in the Formula IX 6 mg+semaglutide group vs. 42.6% in the placebo+semaglutide group, p=0.0505).

In summary by Day 112, placebo+semaglutide treatment resulted in a significant decline in stair climb power and that Formula IX+semaglutide treatment resulted in a statistically significant and clinically meaningful reduction the number of subjects who experienced a decline in physical function measured by the stair climb test.

TABLE 8

| Stair Climb Power (Secondary Endpoint) | | | | |
|---|---|---|---|---|
| | Formula IX 3 mg | Formula IX 6 mg | Formula IX All | Placebo |
| (a) Responder Analysis: Stair Climb Power | | | | |
| Lost ≥5% Stair Climb Power | 26.0% (13/50) | 37.5% (18/48) | 31.6% (31/98) | 51.1% (24/47) |
| p-value | 0.0130 | 0.2180 | 0.0289 | |
| Lost ≥10% Stair Climb Power | 16.0% (8/50) | 22.9% (11/48) | 19.4% (19/98) | 42.6% (20/47) |
| p-value | 0.0066 | 0.0505 | 0.0049 | |

p-values are from Fisher's Exact Test

In summary, the QUALITY study achieved the primary endpoint of preventing lean mass loss, and secondary endpoints of maintaining/increasing fat loss and maintaining/increasing physical function (SCP) as compared to placebo group. These three endpoints were attained without preventing clinically significant loss in mean total body weight. Taken together, these data indicated multiple benefits to taking semaglutide together with Formula IX (and suggests the benefits of taking Formula IX before or after semaglutide). The preservation of lean mass and enhancement of fat mass loss indicated that the total body weight loss under the influence of Formula IX produced an improved body composition compared to semaglutide alone (placebo). For example, in Table 7 above, the median percentage of body weight loss due to lean mass loss in placebo was 31.9% compared to 0.9% and 16.6% in the Formula IX 3 mg and 6 mg groups. When put in the context of relative changes in body composition (using median lean mass values and assuming that the remaining weight loss would be due to fat), 99.1% and 83.4% of weight loss in the Formula IX 3 mg and 6 mg groups was estimated to be loss of fat mass compared to only 68.1% in the placebo group (Table 7). The improved body composition associated with improved physical function that was observed indicates that the quality of the weight loss under the influence of Formula IX plus semaglutide was superior to that of semaglutide alone, even though the total weight loss itself was not quantitatively greater. This high-quality weight loss that improves body composition (and physical function) would be expected to have a myriad of further health benefits.

Such data suggest that Formula IX and other SARMs of the invention exert beneficial effects on body composition in patients taking incretin agonist or antagonist containing drugs including GLP-1 or GIP receptor agonists or antagonists, or other classes of weight loss drugs, or drugs that affect body composition.

Improved body composition as a result of healthy weight loss as described above can lead to many health benefits, including a lower risk of disease, better sleep, and increased energy. Reduced risk of disease includes, inter alia, less heart disease by improving: blood circulation (e.g., normal blood pressure, improved blood lipid profile, less atherosclerosis, etc.), type 2 diabetes due to reduced body fat to increase insulin sensitivity (or decrease insulin resistance) and decrease hyperglycemia and HbA1c levels, and osteoporosis by maintaining healthy bone density which is associated with high lean mass. Favorable body composition changes can also improve quality of life, for example, by improving sleep quality including reducing risk of obstructive sleep apnea (OSA); increasing physical function such that the individual has more energy, endurance, and ability to move; decreased pain due decreased fat mass that reduces pain in joints, hips, and lower back; improved mood and self-confidence, and improved ability to perform daily activities. Improved body composition and physical function lead to improvements in muscle weakness, balance, gait speed, mobility disability, loss of independence, fall risk, bone fracture incidence, physical disability, quality of life, hospitalization rates, and/or mortality. Improved body composition is also associated with improved maintenance of cognitive function and bone health. In summary, older patients who have obesity or are overweight and already may have low muscle reserves who are receiving a GLP-1 RA for weight loss would benefit from a drug to improve body composition by preserving muscle and physical function while enhancing the loss of adiposity or body fat, such as was achieved for Formula IX in the QUALITY study.

Example 8

Phase 2b QUALITY and Maintenance Extension Clinical Study Results

This study provided positive topline efficacy and safety results from the maintenance extension portion of the Phase 2b QUALITY clinical study.

After completing the efficacy dose-finding portion of the Phase 2b QUALITY clinical trial (weeks 1-16, discussed in Examples 6 and 7), 148 participants continued to the Phase 2b Maintenance Extension study. This Phase 2b Maintenance Extension study was a double-blind study, where all patients discontinued semaglutide treatment, but continued receiving placebo, Formula IX 3 mg, or Formula IX 6 mg as monotherapy for 12 weeks. The Phase 2b Maintenance Extension clinical trial addressed the role of Formula IX in preserving lean mass and augmenting fat loss and answered two important questions: (1) whether Formula IX monotherapy, by preserving muscle mass, can also prevent the weight regain and fat regain that generally occurs after stopping semaglutide (Day 112-Day 196) or other weight loss drugs such as liraglutide, tirzepatide or orforglipron; and (2) whether Formula IX plus semaglutide followed by Formula IX monotherapy regimen compared to placebo plus semaglutide followed by placebo monotherapy regimen can maintain both the preserved lean mass and fat loss during Day 1-112 (see Example 7) for a higher quality weight reduction at end of study (Day 1-Day 196; Example 8). Based on the study results, the answers to both important questions are yes.

Phase 2b Maintenance Extension Clinical Trial Results

Formula IX Reduced the Weight Regained after Discontinuation of Semaglutide (Table 9)

At the end of the Phase 2b QUALITY study active weight loss period of 16 weeks (Day 1 to Day 112), body weight loss was similar across treatment groups with the semaglutide plus placebo group losing an average of 11.88 lbs. After the 12-week Maintenance and Extension study period (Day 112 to Day 196) where all treatment groups discontinued semaglutide, the placebo monotherapy group regained 43% of body weight that was previously lost during the Phase 2b QUALITY for a mean percent change of 2.57% (5.06 lbs) in body weight, compared to 1.41% (2.73 lbs) for the 3 mg Formula IX group (p=0.038) and 2.87% (5.29 lbs) for the 6 mg Formula IX group. The 3 mg Formula IX monotherapy significantly reduced the body weight regained by 46%. On average, the placebo monotherapy group regained 2.27% in fat mass, while the Formula IX monotherapy cohorts had a loss of fat mass of −0.27% for the 3 mg and −0.50% for the 6 mg doses. The mean tissue composition of body weight regained was 28% fat and 72% lean mass in the placebo group, versus 0% fat and 100% lean mass in both the 3 mg and the 6 mg Formula IX groups.

The Formula IX Plus Semaglutide Followed by Formula IX Monotherapy Regimen was More Effective in Preserving Lean Mass and Causing and Maintaining Greater Loss of Fat by the End of the Study (Table 10)

By the end of the study at 28 weeks (Day 1 to Day 196), the placebo plus semaglutide followed by placebo monotherapy group experienced a loss of lean mass, while both Formula IX plus semaglutide followed by Formula IX monotherapy groups (3 mg and 6 mg doses) significantly preserved more than 100% of lean mass (Formula IX 3 mg $p<0.001$ and Formula IX 6 mg $p=0.004$). The Formula IX plus semaglutide followed by Formula IX monotherapy patients had a 58% greater loss of fat with Formula IX 3 mg (p=0.085) and a 93% greater loss of fat with Formula IX 6 mg (p=0.008) compared to placebo plus semaglutide followed by placebo monotherapy.

The Phase 2b QUALITY and Maintenance Extension clinical trial confirms that preserving lean mass with Formula IX plus semaglutide led to greater fat loss during the active weight loss period, and after semaglutide was discontinued, Formula IX monotherapy significantly prevented the regain of both weight and fat mass during the maintenance period such that by end of study there was greater loss of fat mass while preserving lean mass for a higher quality weight reduction compared to the placebo group. The details of these topline efficacy results are provided in Table 9 and Table 10 below.

TABLE 9

Phase 2b Maintenance Extension clinical trial efficacy results after discontinuation of semaglutide in all groups (Day 112 to Day 196, ITT population)

| Weight regained (scale weight) | Placebo | Formula IX 3 mg | Formula IX 6 mg |
|---|---|---|---|
| LS Mean % change in body weight (SE) | +2.57% (0.40)<br>n = 48 | +1.41% (0.40)<br>n = 50 | +2.87% (0.41)<br>n = 47 |
| Mean body weight regained (SE) in lbs | +5.06 (0.68) | +2.73 (0.74)<br>p = 0.038* | +5.29 (0.87) |
| % reduction of body weight regained compared to placebo | | −46% | +5% |
| **Fat regained** | **Placebo** | **Formula IX 3 mg** | **Formula IX 6 mg** |
| LS Mean % change in fat mass (SE) | +2.27% (1.19)<br>n = 47 | −0.27% (1.21)<br>n = 47 | −0.50% (1.23)<br>n = 45 |
| Mean fat regained (SE) in lbs | +1.22 (1.08) | −0.43 (0.69) | −0.20 (0.76) |
| % of total body weight regained that is fat mass*** | 28% | 0% | 0% |
| **Lean mass regained** | **Placebo** | **Formula IX 3 mg** | **Formula IX 6 mg** |
| LS Mean % change in lean mass (SE) | +3.18% (0.74)<br>n = 47 | +2.68% (0.75)<br>n = 47 | +5.18% (0.76)<br>n = 45 |
| Mean lean mass regained (SE) in lbs | +3.16 (0.93) | +2.75 (0.60) | +4.98 (0.68) |
| % of total body weight regained that is lean mass*** | 72% | 100% | 100% |

*Analysis of Covariance (ANCOVA)

**Mixed Model for Repeated Measures (MMRM)

***Total weight (mass) regain that is due to lean mass (change in kg) or fat mass (change in kg)

TABLE 10

Phase 2b QUALITY and Maintenance Extension clinical trial efficacy results (Day 1 to Day 196, ITT population)

| Fat mass loss | Placebo + semaglutide followed by placebo | Formula IX 3 mg + semaglutide followed by Formula IX 3 mg alone | Formula IX 6 mg + semaglutide followed by Formula IX 6 mg alone |
|---|---|---|---|
| LS Mean % change in fat mass (SE) (% relative change in fat mass compared to placebo) | −6.00% (1.53) n = 47 | −9.50% (1.52) n = 47 (58% greater fat loss) | −11.60% (1.55) n = 45 (93% greater fat loss) |
| Mean change in fat mass (SE) in lbs | −6.28 (1.19) | −8.80 (1.12)<br>p = 0.085** | −10.03 (1.46)<br>p-0.008** |
| **Lean mass preserved** | **Placebo + semaglutide followed by placebo** | **Formula IX 3 mg + semaglutide followed by Formula IX 3 mg** | **Formula IX 6 mg + semaglutide followed by Formula IX 6 mg** |
| LS Mean % change in lean mass (SE) (% relative change in lean mass compared to placebo) | −0.94% (0.84) n = 47 | +2.70% (0.83) n = 47 (>100% of lean mass preserved) | +2.36% (0.85) n = 45 (>100% of lean mass preserved) |
| Mean change in lean mass (SE) in lbs | −1.23 (0.97) | +2.77 (0.69)<br>P = 0.001** | +2.54 (0.83)<br>p = 0.004** |

**Mixed Model for Repeated Measures (MMRM)

The Phase 2b Maintenance Extension clinical trial demonstrated that in 12 weeks after stopping semaglutide, the placebo monotherapy group regained 43% of body weight that was previously lost during the Phase 2b QUALITY study, while Formula IX monotherapy reduced weight regain by 46% in the Formula IX 3 mg group and completely prevented fat regain and preserved lean mass in both Formula IX dose groups compared to placebo after semaglutide discontinuation. Formula IX treatment also led to up to 93% greater loss of fat mass and 100% preservation of lean mass compared to the placebo group at the end of the study. Formula IX monotherapy maintained a positive safety profile, with essentially no gastrointestinal side effects observed during the maintenance period.

Based on the Phase 2b QUALITY active weight loss portion of the study, Formula IX 3 mg preserved 100% of lean mass, 99% of body weight loss was from fat, and preserved physical function as measured by stair climb test, when combined with a GLP-1 drug compared to placebo. The Maintenance Extension portion of the study shows that if patients stop a GLP-1 drug such as orforglipron, tirzepatide or semaglutide, they can preserve lean mass, blunt the regain of fat and weight, and keep off the fat they lost when they remain on Formula IX monotherapy. Formula IX provides a compelling option for patients that would like to maintain their weight loss and fat loss after discontinuing semaglutide, regardless of whether such discontinuation was by choice or by necessity.

Both muscle preservation and improvement in physical function were observed with Formula IX when given with semaglutide, a GLP-1 medication. One advantage of Formula IX is that it's an oral agent and with encouraging safety and tolerability profiles.

The concern about older people with obesity losing weight using a GLP-1 receptor agonist has been related to a substantial amount of muscle mass loss. The use of Formula IX with semaglutide preserved lean mass while increasing fat loss. By preserving lean mass, a higher energy expenditure produces greater fat loss. Formula IX has been shown to help not only with active weight loss, but also to maintain fat loss. Preservation of lean mass by Formula IX with semaglutide treatment was associated with remarkable positive differences in physical function as evidenced by stair climb power, which is critical for the preservation of mobility for an aging population. These results may allow clinicians to prescribe a GLP-1 RA in combination with Formula IX for weight loss with confidence that their patients will lose fat and preserve functional status.

Phase 2b QUALITY and maintenance extension clinical study showing Formula IX significantly reduced body weight regain, prevented fat regain, and preserved lean mass after semaglutide discontinuation.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A method for reducing or treating adverse effects caused by semaglutide monotherapy in a subject, comprising co-administering to the subject a composition comprising a pharmaceutical composition of Formula IX or an optical isomer, a racemic mixture, a pharmaceutically acceptable salt, a pharmaceutical product, a hydrate, an N-oxide, or a crystal thereof; and a pharmaceutical composition of semaglutide

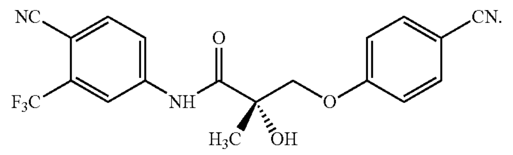

IX

2. The method according to claim 1, wherein (i) the subject has obesity and (ii) the subject is 60 years old or older.

3. The method according to claim 1, wherein the adverse effects comprise one or more of loss in (i) lean body mass, fat-free mass, or muscle mass, (ii) muscle strength, and (iii) physical function.

4. The method according to claim 3, wherein the loss in lean body mass is from about 3% to 20% of the total body weight in the subject.

5. The method according to claim 1, wherein the method results in one or more of (i) reducing the loss of lean body mass, preserving lean body mass, or gaining lean body mass (muscle mass) in the subject, (ii) reversing bone loss or gaining bone in the subject, (iii) overcoming or improving insulin resistance in the subject, and (iv) improving HbA1c in the subject.

6. The method according to claim 1, wherein the method results in one or more of reducing abdominal, subcutaneous, or intramuscular fat accumulation, improving body composition, lowering body fat content, lowering fat mass, or increasing or preserving muscle mass or muscle strength or muscle physical function in the subject.

7. The method according to claim 1, wherein the method results in preservation or restoration of lean body mass (LBM) or muscle in the subject, or wherein the method enhances fat loss or prevents fat regain.

8. The method according to claim 1, wherein the method reduces or treats muscle weakness, poor balance, decreased gait speed, mobility disability, loss of independence, increased risk of falls, bone fractures, loss of physical function, physical disability, poor quality of life, high hospitalization rates, and/or increased mortality in the subject.

9. The method according to claim 8, wherein the bone fractures are fractures of the hip or pelvis in the subject.

10. The method according to claim 1, wherein the Formula IX is administered to the subject concurrently with or after the treatment with the semaglutide.

11. The method according to claim 1, wherein said method reduces or treats lean mass loss in a subject who is under treatment or stops treatment with the semaglutide.

12. The method according to claim 11, wherein the method decreases fat mass while preserving or increasing lean mass in the subject.

13. The method according to claim 11, wherein the method improves physical function.

14. The method according to claim 11, further reducing and treating muscle weakness, poor balance, decreased gait speed, mobility disability, loss of independence, increased risk of falls, bone fractures, loss of physical function, physical disability, poor quality of life, high hospitalization rates, and/or increased mortality in the subject.

15. The method according to claim 14, wherein the bone fractures are fractures of the hip or pelvis in the subject.

16. The method according to claim 1, wherein the Formula IX is formulated for administration at a dose of from 0.1 mg to 50 mg per day, or wherein the Formula IX is formulated for administration at a dose of 3 mg per day or 6 mg per day, and wherein the semaglutide is formulated for administration at the dose of from 0.25 mg per week to 1.7 mg per week.

17. A method for maintenance or improvement of body composition compared to semaglutide monotherapy in a subject, comprising co-administering to the subject a composition comprising a pharmaceutical composition of Formula IX or an optical isomer, a racemic mixture, a pharmaceutically acceptable salt, a pharmaceutical product, a hydrate, an N-oxide, or a crystal thereof; and a pharmaceutical composition of semaglutide

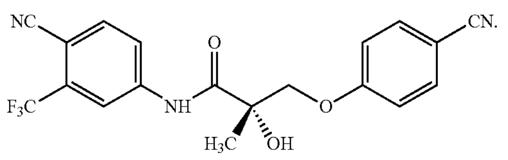

IX

18. The method for maintenance or improvement of body composition according to claim 17, wherein the subject discontinues semaglutide, but continues treatment with Formula IX as monotherapy.

19. The method according to claim 17, wherein said improved body composition is represented by further decreasing fat mass while preserving or increasing lean mass in a subject who is under treatment with said co-administered semaglutide and Formula IX or stops treatment with semaglutide, relative to a subject who is under treatment with the semaglutide alone.

20. The method according to claim 17, wherein said improved body composition is represented by further decreasing fat mass while preserving or increasing lean mass in a subject who was co-administered the semaglutide and the Formula IX, and then said semaglutide is discontinued; relative to a subject who is under treatment with the semaglutide alone.

21. The method according to claim 17, wherein the physical function or muscle strength is maintained or improved.

22. The method according to claim 17, wherein (i) the subject has obesity and (ii) the subject is 60 years old or older.

23. The method according to claim 17, wherein the method reduces or treats rebound of one or more of (i) weight gain, (ii) fat mass gain, and (iii) lean mass loss when the semaglutide is discontinued.

24. The method according to claim 17, wherein the method results in preservation or restoration of lean body mass (LBM) or muscle in the subject.

25. The method according to claim 17, wherein said method augments fat loss or prevents fat regain.

26. The method according to claim 17, wherein the Formula IX is formulated for administration at a dose of from 0.1 mg to 50 mg per day, or wherein the Formula IX is formulated for administration at a dose of 3 mg per day or 6 mg per day, and wherein the semaglutide is formulated for administration at the dose of from 0.25 mg per week to 1.7 mg per week.

27. A method for reducing or treating rebound in a subject in need thereof, wherein the rebound is in one or more of (i) weight gain, (ii) fat mass gain, and (iii) lean mass loss when the semaglutide is discontinued in said subject but Formula IX or an optical isomer, a racemic mixture, a pharmaceutically acceptable salt, a pharmaceutical product, a hydrate, an N-oxide, or a crystal thereof; treatment continues as monotherapy:

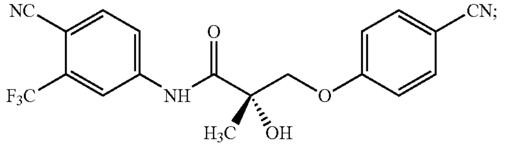

IX wherein the subject was previously administered a composition comprising a pharmaceutical composition of Formula IX and a pharmaceutical composition of semaglutide.

28. The method according to claim 27, wherein the method results in preservation or restoration of lean body mass (LBM) or muscle in the subject, or wherein the method enhances fat loss or prevents fat regain.

29. The method according to claim 27, wherein the Formula IX is administered to the subject concurrently with or after the treatment with the semaglutide.

30. The method according to claim 27, wherein said method reduces or treats lean mass loss in a subject who is under treatment or stops treatment with the semaglutide.

* * * * *